(12) United States Patent
Sun

(10) Patent No.: US 9,937,259 B2
(45) Date of Patent: Apr. 10, 2018

(54) ABIRATERONE DERIVATIVES AND NON-COVALENT COMPLEXES WITH ALBUMIN

(71) Applicant: Zhuhai Beihai Biotech Co., Ltd., Zhuhai (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 0 days.

(21) Appl. No.: 15/320,353

(22) PCT Filed: Jun. 26, 2015

(86) PCT No.: PCT/US2015/038077
§ 371 (c)(1),
(2) Date: Dec. 20, 2016

(87) PCT Pub. No.: WO2015/200837
PCT Pub. Date: Dec. 30, 2015

(65) Prior Publication Data
US 2017/0216443 A1 Aug. 3, 2017

Related U.S. Application Data

(60) Provisional application No. 62/046,616, filed on Sep. 5, 2014, provisional application No. 62/018,236, filed on Jun. 27, 2014.

(51) Int. Cl.
*C07D 213/02* (2006.01)
*C07J 43/00* (2006.01)
*A61K 31/44* (2006.01)
*A61K 31/58* (2006.01)
*A61K 47/42* (2017.01)

(52) U.S. Cl.
CPC .............. *A61K 47/42* (2013.01); *A61K 31/58* (2013.01); *C07J 43/003* (2013.01)

(58) Field of Classification Search
None
See application file for complete search history.

(56) References Cited

U.S. PATENT DOCUMENTS

| 5,604,213 | A | 2/1997 | Barrie et al. |
|---|---|---|---|
| 5,635,517 | A | 6/1997 | Muller et al. |
| 7,445,764 | B1 | 11/2008 | Kratz |
| 7,452,900 | B2 | 11/2008 | Marzi |
| 7,498,340 | B2 | 3/2009 | Marzi |
| 7,576,104 | B2 | 8/2009 | Robarge et al. |
| 7,772,254 | B2 | 8/2010 | Sun |
| 7,820,788 | B2 | 10/2010 | Desai et al. |
| 7,923,536 | B2 | 4/2011 | Desai et al. |
| 8,076,474 | B2 | 12/2011 | Hunt |
| 8,138,229 | B2 | 3/2012 | Desai et al. |
| 8,338,588 | B2 | 12/2012 | Hunt |
| 8,748,610 | B2 | 6/2014 | Sun |
| 8,853,260 | B2 | 10/2014 | Desai et al. |
| 8,911,775 | B2 | 12/2014 | Lee et al. |
| 8,927,694 | B2 | 1/2015 | McDonagh et al. |
| 8,927,725 | B2 | 1/2015 | Greig et al. |
| 9,150,585 | B2 | 10/2015 | Sun |
| 2009/0253651 | A1 | 10/2009 | Norbedo et al. |
| 2011/0021567 | A1 | 1/2011 | Devarakonda et al. |
| 2012/0177743 | A1 | 7/2012 | Desai et al. |
| 2012/0283292 | A1 | 11/2012 | Milne et al. |
| 2014/0024807 | A1 | 1/2014 | Salamone et al. |
| 2014/0135356 | A1 | 5/2014 | Sun |
| 2015/0290332 | A1 | 10/2015 | Kim et al. |
| 2015/0291562 | A1 | 10/2015 | Crew et al. |
| 2015/0366984 | A1 | 12/2015 | Sun |
| 2016/0145314 | A1 | 5/2016 | Li et al. |

FOREIGN PATENT DOCUMENTS

| CN | 1863790 | 11/2006 |
|---|---|---|
| EP | 2007386 | 8/2012 |
| WO | WO2003066595 | 8/2003 |
| WO | WO2005030753 | 4/2005 |
| WO | WO2008133973 | 11/2008 |
| WO | WO2009023539 | 2/2009 |
| WO | WO2009074678 | 6/2009 |
| WO | WO2009126920 | 10/2009 |
| WO | WO2010092342 | 8/2010 |
| WO | WO2011085000 | 7/2011 |
| WO | WO2014121033 | 8/2014 |

OTHER PUBLICATIONS

Marbury et al, Chemical Abstract 162:265369, Abstract of Journal of Clinical Pharmacology, 53(7), pp. 732-741 (Year: 2013).*
International Preliminary Report on Patentability for PCT/US2015/056900, dated May 4, 2017, 6 pages.
International Search Report and Written Opinion for PCT/US2015/056900, dated Dec. 29, 2015, 13 pages.
"Multiple Myeloma: Treatment Options," Cancer.Net [online] Sep. 2014 [retrieved on Sep. 23, 2014]. Relieved from the Internet: <URL: http://www.cancer.net/cancer-types/multiple-myeloma/treatment-options>, 7 pages.
"Myelodysplastic Syndromes Treatment (PDQ®)," Cancer.gov [online] Jun. 11, 2014 [retrieved on Sep. 24, 2014]. Retrieved from the Internet: <URL: http://www.cancer.gov/cancertopics/pdq/treatment/myelodysplastic/page1/AllPages/Print>, 17 pages.
"POMALYST® (pomalidomide) capsules, for oral use," [prescribing informations], Feb. 2013, 13 pages.
"REVLIMID [lenalidomide] capsules, for oral use," [prescribing information], Jun. 2013, 33 pages.
"Revlimid® (lenalidomide) capsules Data sheet," 22 pages, Apr. 2013.
"ZYTIGA® (abiraterone acetate) Tablets," [prescribing information], Dec. 2012, 9 pages.
Accession No. 158:253017 CA, 1 page, 2012.
Accession No. 158:662530 CA, 1 page, 2012.
Akhtar et al., "Cytochrome b(5) modulation of 17 {alpha} hydroxylase and 17-20 lyase (CYP17) activities in steroidogenesis," *J Endocrinol.*, 187(2):267-274, Nov. 2005.
Birder et al., "Altered urinary bladder function in mice lacking the vanilloid receptor TRPV1," *Nat. Neurosci.*, 5(9):856-360, Sep. 2002.

(Continued)

*Primary Examiner* — Zinna Northington Davis
(74) *Attorney, Agent, or Firm* — Fish & Richardson P.C.

(57) ABSTRACT

The present disclosure provides derivatives of abiraterone, non-covalently bound complexes of the abiraterone derivatives with serum albumin, pharmaceutical compositions of the same, and methods of use thereof. The non-covalently bound complexes are significantly more water-soluble than abiraterone and are useful for the treatment of a disease or condition that can benefit from CYP17 inhibition, such as prostate cancer.

19 Claims, 4 Drawing Sheets

(56) References Cited

OTHER PUBLICATIONS

Bley, "Recent developments in transient receptor potential vanilloid receptor 1 agonist-based therapies," Exp. Opin Investig Drugs., 13(11):1445-1456, Nov. 2004.
Bosse et al., "Phase I comparability of recombinant human albumin and human serum albumin," *J Clin Pharmacol.*, 45(1):57-67, Jan. 2005.
Briggs et al., "An adverse reaction to the administration of disoprofol (Diprivan)," *Anaesthesia*, 37(11):1099-1101, Nov. 1982.
Bruno et al., "Population pharmacokinetics/pharmacodynamics of docetaxel in phase II studies in patients with cancer," *J Clin Oncol.*, 16(1):187-196, Jan. 1998.
Carter and Ho, "Structure of serum albumin," *Adv Protein Chem.*, 45:153-203, 1994.
Caterina et al., "Impaired nociception and pain sensation in mice lacking the capsaicin receptor," *Science*, 288(5464):306-313, Apr. 2000.
Caterina et al., "The capsaicin receptor: a heat-activated ion channel in the pain pathway," *Nature*, 389(6653):816-824, Oct. 23, 1997.
Chen et al., "Human serum albumin from recombinant DNA technology: challenges and strategies," *Biochim Biophys Acta.*, 1830(12):5515-1525, Epub May 3, 2013.
Chen et al., "Removal of fatty acids from serum albumin by charcoal treatment," *J Biol Chem.*, 242(2):173-181, Jan. 25, 1967.
Chen et al., "Results of molecular docking as descriptors to predict human serum albumin binding affinity," *J Mol Graph Model.*, 33:35-43, Epub Nov. 23, 2011.
ClinicalTrials.gov Identifier: NCT00783367, "Combination Therapy Using Lenalidomide (Revlimid)-Low Dose Dexamethasone and Rituximab for Treatment of Rituximab-Resistant, Non-Aggressive B-Cell Lymphomas," ClinicalTrials.gov [online] xx [retrieved on Sep. 24, 2014]. Retrieved from the Internet: <URL: https://clinicaltials.gov/ct2/show/NCT00783367?term=lenalidomide&rank=4>, 5 pages.
ClinicalTrials.gov Identifier: NCT01183663, "Lenalidomide in Combination with Bevacizumab, Sorafenib, Temsirolimus, or 5-Fluorouracil, Leucovorin, Oxaliplatin (FOLFOX)," ClinicalTrials.gov [online] Aug. 11, 2014 [retrieved on Sep. 24, 2014]. Retrieved from the Internet: <URL: https://clinicaltrials.gov/ct2/show/NCT01183663?term=lenalidomide&rank=9>, 5 pages.
ClinicalTrials.gov Identifier: NCT01358734, "A Study Being Conducted at Multiple Locations to Compare the Safety and Effectiveness of Three Different Treatment Regimens; 1) Lenalidomide, 2) Lenalidomide + Azacitidine, or 3) Azacitidine Alone in Newly Diagnosed Acute Myeloid Leukemia in Elderly Subjects ≥ 65 Years of Age," ClinicalTrials.gov [online] Jun. 30, 2014 [retrieved on Sep. 24, 2014]. Retrieved from the Internet: <URL: https://clinicaltrials.gov/ct2/show/NCT01358734?term=lenalidomide&rank=15>, 4 pages.
ClinicalTrials.gov Identifier: NCT01460940, "A Phase II Trial of Panobinostat and Lenalidomide in Patients with Relapsed or Refractory Hodgkin's Lymphoma," ClinicalTrials.gov [online] Jul. 15, 2013 [retrieved on Sep. 24, 2014]. Retrieved from the Internet: <URL: https://clinicaltrials.gov/ct2/show/NCT01460940?term=lenalidomide&rank=13>, 5 pages.
ClinicalTrials.gov Identifier: NCT01704781, "Vacc-4x ÷ Lenalidomide vs. Vacc-4x +Placebo in HIV-1-infected Subjects on Antiretroviral Therapy (ART) (IMID)," ClinicalTrials.gov [online] Jul. 30, 2014[retrieved on Sep. 24, 2014]. Retrieved from the Internet: <URL: https://clinicaltrials.gov/ct2/show/NCT01704781?term=lenalidomide&rank=1>, 4 pages.
Cohn and Strong, "Preparation and properties of serum and plasma proteins: a system for the separation into fractions of the protein and lipoprotein components of biological tissues and fluids," *J Am Chem Soc.*, 68:459-475, Mar. 1946.
Curry et al., "Crystal structure of human serum albumin complexed with fatty acid reveals an asymmetric distribution of binding sites," *Nat Struct Biol.*, 5(9):827-835, Sep. 1998.
Davis et al., "Vanilloid receptor-1 is essential for inflammatory thermal hyperalgesia," *Nature*, 405(6783): 183-187, May 11, 2000.

Di Marzo et al., "Endovanilloid signaling in pain," *Curr. Opin. Neurobiol.*, 12(4):372-379, Aug. 2002.
EMEA, "Scientific Discussion," 42 pages, 2007.
Fehske et al., "The location of drug binding sites in human serum albumin," *Biochem Pharmacol.*, 30(7):687-692, Apr. 1, 1981.
Ferrajoli et al., "Combination therapy with lenalidomide and rituximab in patients with relapsed chronic lymphocytic leukemia (CCL)," Blood, (ASH Annual Meeting Abstracts) 114: Abstract 206, 2 pages, 2009.
Finlayson, "Albumin Products." *Seminars in Thrombosis and Hemostasis*, 6(2):85-120, 1980.
Ge et al., "Protein-polymer hybrid nanoparticles for drug delivery," *Small.*, 8(23):3573-3578, Epub Aug. 9, 2012 (Abstract only).
He et al., "Atomic structure and chemistry of human serum albumin," *Nature*, 358(6383):209-215, Jul. 16, 1992.
Hideshima et al., "A review of lenalidomide in combination with dexamethasone for the treatment of multiple myeloma," *Ther Clin Risk Manag.*, 4(1):129-136, Feb. 2008.
International Preliminary Report on Patentability for PCT /US2014/014079, dated Aug. 13, 2015, 7 pages.
International Search Report and Written Opinion for PCT/US2014/14079 dated May 13, 2014, 8 pages.
International Preliminary Report on Patentability of the International Application No. PCT/US2015/38077, dated Jan. 5, 2017, 7 pages.
International Search Report and Written Opinion of the International Application No. PCT/US2015/38077, dated Sep. 24, 2015, 15 pages.
Janssen, "ZYTIGA® abiraterone acetate product information," Mar. 1, 2012, 12 pages.
Kasim et al., "Molecular properties of WHO essential drugs and provisional biopharmaceutical classification," *Mol Pharm.*, 1(1):85-96, Jan. 12, 2004.
Kotla et al., "Mechanism of action of lenalidomide in hematological malignancies," *J Hematol Oncol.*, 2:36, Aug. 12, 2009.
Kragh-Hansen, "Structure and ligand binding properties of human serum albumin," *Dan Med Bull.*, 37(1):57-84, Feb. 1990.
Kratz, "Albumin as a drug carrier: design of prodrogs, drug conjugates and nanoparticles," *J Control Release.*, 132(3):171-183, Epub May 17, 2008.
Kularatne et al., "Synthesis and biological analysis of prostate-specific membrane antigen-targeted anticancer prodrugs," *J Med Chem.*, 53(21):7767-7777, Nov. 11, 2010.
Li et al., "Preparation, characterization and targeting of micronized 10-hydroxycamptothecin-loaded folate-conjugated human serum albumin nanoparticles to cancer cells," *Int J Nanomedicine.*, 6:397-405, Epub Feb. 20, 2011.
Lin et al., "Stability of human serum albumin during bioprocessing: denaturation and aggregation during processing of albumin paste," *Pharm Res.*, 17(4):391-396, Apr. 2000.
Lipinski, "Drug-like properties and the causes of poor solubility and poor permeability," *J Pharmacol Toxicol Methods*, 44(1):235-249, Jul.-Aug. 2000.
Lopez-Gomez, "Management of colorectal cancer patients after resection of liver metastases: can we offer a tailored treatment?" *Clin Transl Oncol.*, 14(9):641-658, Epub Aug. 22, 2012.
Mezey et al., "Distribution of mRNA for vanilloid receptor subtype 1 (VR1), and VR1-like immunoreactivity, in the central nervous system of the rat and human," *Proc Natl Acad Sci U S A.*, 97(7):3655-3660, Mar. 28, 2000.
Piccart et al., "Docetaxel: an active new drug for treatment of advanced epithelial ovarian cancer," *J Natl Cancer Inst.*, 87(9):676-681, May 3, 1995.
Pomonis et al., "N-(4-Tertiarybutylphenyl)-4-(3-cholorphyridin-2-yl) tetrahydropyrazine-1(- 2H)-carbox-amide (BCTC), a novel, orally effective vanilloid receptor 1 antagonist with analgesic properties: II. in vivo characterization in rat models of inflammatory and neuropathic pain," J Pharmacol Exp Ther., 306(1):387-393, Epub. Apr. 29, 2003.
Prijovich et al., "Stability of the new prodrug 9-aminocamptothecin glucuronide (9ACG) in the presence of human serum albumin." Biochem Pharmacol., 66(7):1181-1187, Oct. 1, 2003.

(56) References Cited

OTHER PUBLICATIONS

Rajkumar et al., "Combination therapy with lenalidomide plus dexamethasone (Rev/Dex) for newly diagnosed myeloma," *Blood*, 106(13):4050-4053, Epub Aug. 23, 2005.

Ratain, "Flushing oral oncology drugs down the toilet," *J Clin Oncol.*, 29(30):3958-3959, Epub Sep. 19, 2011.

Ryan et al., "Structural basis of binding of fluorescent, site-specific dansylated amino acids to human serum albumin," *Journal of Structural Biology.*, 174:84-91, 2011.

Samor et al., "The role of polyamine architecture on the pharmacological activity of open lactone camptothecin-polyamine conjugates," *Bioconjug Chem.*, 19(11):2270-2279, Nov. 19, 2008.

Sartor et al., "Novel therapeutic strategies for metastatic prostate cancer in the post-docetaxel setting," *Oncologist.*, 16(11):1487-1497, Epub Nov. 2, 2011.

Schmid et al., "Development of albumin-binding camptothecin prodrugs using a Peptide positional scanning library," *Bioconjug Chem.*, 18(6):1786-1799, Epub Oct. 5, 2007.

Semeraro et al., "Trial Watch: Lenalidomide-based immunochemotherapy," 2(11):e26494. Epub Oct. 21, 2013.

Silverman and Holladay, *The Organic Chemistry of Drug Design and Drug Action*, Elsevier, pp. 29-32, 2004.

Sugio et al., "Crystal structure of human serum albumin at 2.5 A resolution," *Protein Eng.*, 12(6):439-446, Jun. 1999.

Todd et al., "Fast and flawed or scientifically sound: the argument for administering oral oncology drugs during fasting," *J Clin Oncol.*, 30(8):888-889, Epub Feb. 13, 2012.

Trudeau et al., "Docetaxel in patients with metastatic breast cancer: a phase II study of the National Cancer Institute of Canada-Clinical Trials Group," *J Clin Oncol.*, 14(2):422-428, Feb. 1996.

Trynda-Lemiesz, "Effect of cis-, trans-diamminedichloroplatinum(II) and DBP on human serum albumin," *J Inorg Biochem.*, 77(3-4):141-146, Nov.-Dec. 1999.

Tullis, "Albumin. 1. Background and use," *JAMA.*, 237(4):355-360, Jan. 24, 1977.

Vannucchi, "Management of myelofibrosis," Hematology Am Soc Hematol Educ Program., 2011:222-230, 2011.

Vorum, "Reversible ligand binding to human serum albumin. Theoretical and clinical aspects," *Dan Med Bull.*, 46(5):379-399, Nov. 1999.

Walker et al., "The VR1 antagonist capsazepine reverses mechanical hyperalgesia in models of inflammatory and neuropathic pain," *J. Pharm. Exp. Ther.*, 304(1): 56-62, Jan. 2003.

Yu et al., "Spectroscopic investigation of the interaction between camptothecin and bovine serum albumin," Fenxi Shiyanshi, 31(1): 42-46, 2012 [English abstract].

Zhang, "Methoxy poly(ethylene glycol) conjugated denatured bovine serum albumin micelles for effective delivery of camptothecin," Polym Chem, 3(8):1958-1961, Aug. 2012.

Zsila, "Evaluation of drug-human serum albumin binding interactions with support vector machine aided online automated docking," *Bioinformatics*, 27(13):1806-1813, Epub May 18, 2011.

Zu et al., "Preparation of 10-hydroxycamptothecin-loaded glycyrrhizic acid-conjugated bovine serum albumin nanoparticles for hepatocellular carcinoma-targeted drug delivery," *Int J Nanomedicine.*, 8:1207-1222, Epub Mar. 27, 2013.

\* cited by examiner

ABIRATERONE DERIVATIVES AND NON-COVALENT COMPLEXES WITH ALBUMIN

CROSS REFERENCE TO RELATED APPLICATIONS

This application is a national stage application under 35 U.S.C. § 371 of International Application No. PCT/US2015/038077, filed on Jun. 26, 2015, which claims the benefit of U.S. Provisional Ser. No. 62/018,236 filed Jun. 27, 2014 and U.S. Provisional Ser. No. 62/046,616 filed Sep. 5, 2014. The entire contents of the above applications, including drawings, are incorporated by reference.

TECHNICAL FIELD

This disclosure relates to abiraterone derivatives, non-covalent complexes of the derivatives with albumin, for example, human serum albumin, methods of preparation and pharmaceutical uses thereof.

BACKGROUND

About 30% of drugs that appear on the World Health Organization (WHO) Essential Drug List were reported to be poorly water-soluble, based on the Biopharmaceutics Classification System (BCS). See, for example, Kasim, N. A., et al., Molecular properties of WHO essential drugs and provisional biopharmaceutical classification, *Molecular Pharmaceutics* 2004, 1(1): p. 85-96. Over 40% of newly developed pharmaceutically active substances have solubility issues. See Lipinski, C. A., Drug-like properties and the causes of poor solubility and poor permeability, *Journal of Pharmacological and Toxicological Methods* 2000, 44(1): p. 235-249. The poor dissolution and/or permeability of these drugs often results in low, but highly variable, bioavailability. Further, a major obstacle of successfully commercializing these compounds is the difficulty of enhancing their dissolution rate and extent of dissolution.

For example, abiraterone acetate is approved in the United States as an oral treatment for metastatic castration-resistant prostate cancer. The product insert describes abiraterone acetate as a lipophilic compound that is practically insoluble in water. See Zytiga™ Full Prescribing Information, 2012, Janssen Biotech Inc., Section 11. While the insolubility of abiraterone acetate allows for its preparation in capsule form for oral dosing, it precludes intravenous (IV) administration which is used for other treatments of prostate cancer, such as cabazitaxel. See Sartor, O. et al. *The Oncologist* 2011, 16: 1487-1497.

Due to its insolubility, abiraterone acetate suffers from low bioavailability that arises from poor absorption, as 77% of the administered drug is excreted. See Ratain, M. J. *Journal of Clinical Oncology* 2011, 29(30): 3958-3959). Thus, most of the administered drug is not used for its intended treatment.

The low water solubility of abiraterone acetate has led to a food-effect that is greater than any other marketed drug (five- to ten-fold, depending on fat content of the meal), and significant interindividual pharmacokinetic variability. This food-effect can also afford a large intraindividual variability, resulting in underdosing or overdosing. Thus, strict patient compliance is required to achieve the dosing under labeled conditions.

Further, abiraterone acetate is a substrate of the CYP3A4 liver enzyme, which can lead to potential drug-drug interactions with other administered drugs that inhibit or induce CYP3A4. See Zytiga™ Full Prescribing Information, 2012, Janssen Biotech Inc., Section 7.2.

The development of soluble abiraterone derivatives would allow for IV dosing, which bypasses the liver, and could alleviate some of the aforementioned problems.

Accordingly, there is a clear and continuing need to create more soluble forms of abiraterone.

SUMMARY

An aspect of the current disclosure provides a non-covalently bound complex of an abiraterone derivative and human serum albumin in a molar ratio from about 1:1 to about 10:1, wherein the non-covalently bound complex has a solubility in aqueous solution of at least 5 mg/mL, and the abiraterone derivative comprises a compound of Formula (I):

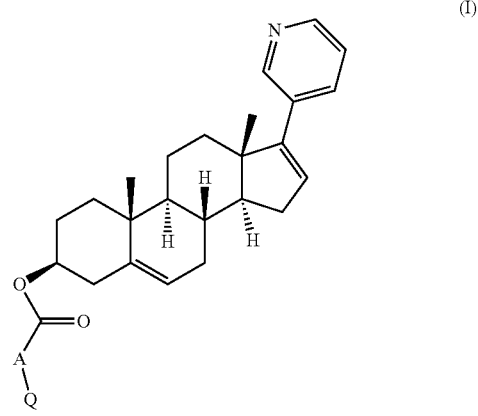

wherein
A is a covalent bond, O, or $NR^1$;
$R^1$ is H, lower alkyl, or alkaryl, wherein the alkyl or alkaryl is optionally substituted with 1-3 substituents independently selected from the group consisting of: halo, nitro, amine, amide, hydroxyl, O-lower alkyl, and carboxy; and
Q is a group that selectively binds to human serum albumin.

The present disclosure further provides a compound, or a pharmaceutically acceptable salt thereof, according to Formula (II):

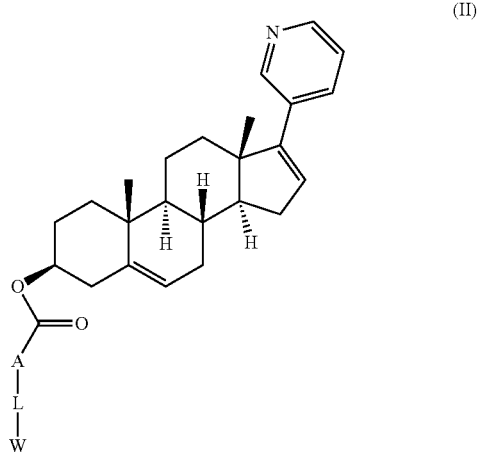

wherein

A is a covalent bond, O, or NR$^1$;

L is alkyl, alkenyl, alkynyl, carbocyclyl, carbocyclylalkyl, aryl, alkaryl, or

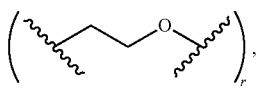

each of which is optionally substituted with 1-3 substituents independently selected from the group consisting of halo, —NO$_2$, amine, amide, hydroxyl, O-lower alkyl, and —COOH, provided that there be no covalent bonds between oxygen atoms;

W is

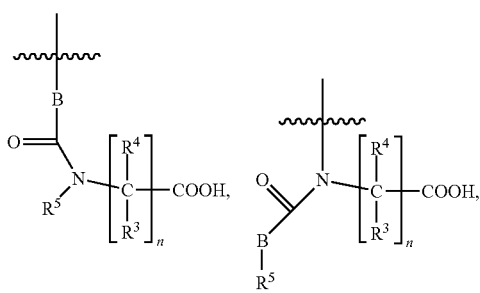

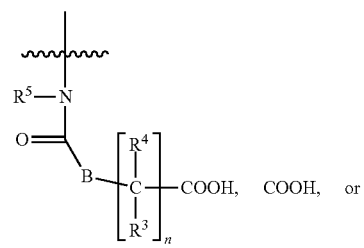

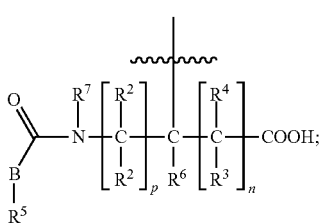

R$^1$ is H, lower alkyl, or alkaryl, wherein the alkyl or alkaryl is optionally substituted with 1-3 substituents independently selected from the group consisting of: halo, NO$_2$, amine, amide, hydroxyl, O-lower alkyl, and —COOH;

R$^2$ is independently in each instance H, OH, NO$_2$, NH$_2$, NH$_3^+$, SH, or a branched or unbranched C$_{1-8}$ alkyl, C$_{2-8}$ alkenyl, or C$_{2-8}$ alkynyl, wherein the C$_{1-8}$ alkyl, C$_{2-8}$ alkenyl, or C$_{2-8}$ alkynyl is optionally substituted with 1-2 substituents independently selected from the group consisting of halo, OH, NO$_2$, NH$_2$, NH$_3^+$, SH and =O, and wherein the C$_{1-8}$ alkyl, C$_{2-8}$ alkenyl or C$_{2-8}$ alkynyl optionally has 1-2 heteroatoms independently selected from O, S, and NH wherein each heteroatom replaces a CH$_2$, with the proviso that no O, S, or N atom in the C$_{1-8}$ alkyl, C$_{2-8}$ alkenyl or C$_{2-8}$ alkynyl is covalently bonded to another O, S, or N atom;

R$^3$ is independently in each instance H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^4$ is independently in each instance H, OH, NO$_2$, NH$_2$, NH$_3^+$, SH, or a branched or unbranched C$_{1-10}$ alkyl, C$_{2-10}$ alkenyl or C$_{2-10}$ alkynyl, wherein the C$_{1-10}$ alkyl, C$_{2-10}$ alkenyl or C$_{2-10}$ alkynyl is optionally substituted with 1-2 substituents independently selected from the group consisting of halo, OH, NO$_2$, NH$_2$, NH$_3^+$, SH, and =O, and wherein the C$_{1-10}$ alkyl, C$_{2-10}$ alkenyl or C$_{2-10}$ alkynyl optionally has 1-2 heteroatoms independently selected from O, S and NH wherein each heteroatom replaces a CH$_2$, with the proviso that no O, S, or N atom in the C$_{1-10}$ alkyl, C$_{2-10}$ alkenyl, or C$_{2-10}$ alkenyl is covalently bonded to another O, S, or N atom;

R$^5$ is H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^6$ and R$^7$ are each independently H or lower alkyl, optionally substituted with 1-3 substituents independently selected from the group consisting of halo, nitro, amine, amide, hydroxyl, O-lower alkyl and carboxy;

B is a covalent bond, O or NR$_1$;

p is 1, 2, 3, 4, 5, or 6;

n is 1, 2, 3, 4, 5, or 6; and r is 1, 2, 3, 4, 5, 6, 7, 8, 9, or 10.

The disclosure further provides a compound, or pharmaceutically acceptable salt thereof, according to Formula (III):

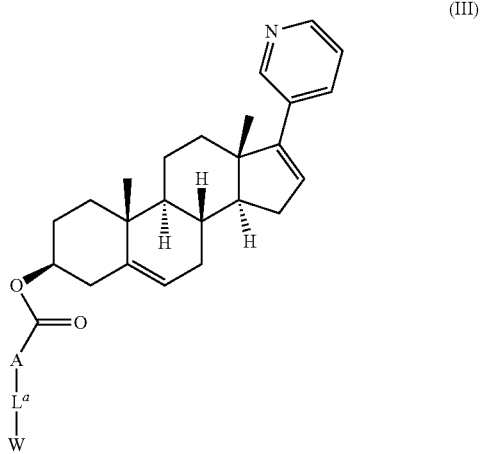

wherein
A is a covalent bond, O, or NR$^1$;
L$^a$ is a linker including a —S—S— moiety;
W is

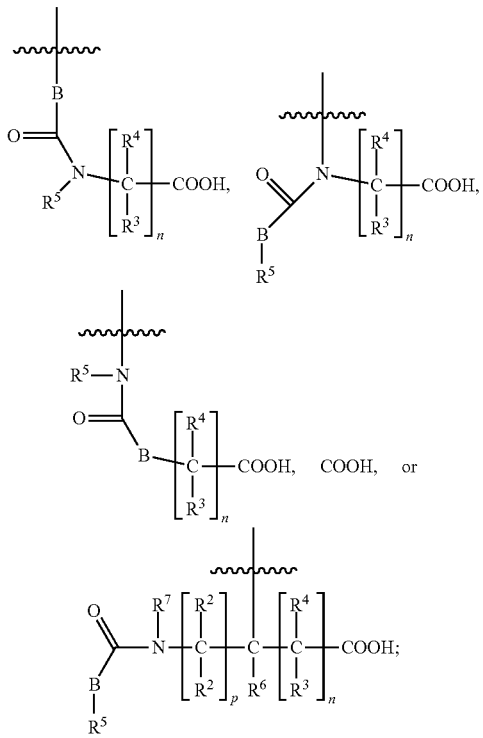

R$^1$ is H, lower alkyl, or alkaryl, wherein the alkyl or alkaryl is optionally substituted with 1-3 substituents independently selected from the group consisting of: halo, NO$_2$, amine, amide, hydroxyl, O-lower alkyl, and —COOH;

R$^2$ is independently in each instance H, OH, NO$_2$, NH$_2$, NH$_3^+$, SH, or a branched or unbranched C$_{1-8}$ alkyl, C$_{2-8}$ alkenyl, or C$_{2-8}$ alkynyl, wherein the C$_{1-8}$ alkyl, C$_{2-8}$ alkenyl or C$_{2-8}$ alkynyl is optionally substituted with 1-2 substituents independently selected from the group consisting of halo, OH, NO$_2$, NH$_2$, NH$_3^+$, SH and =O, and wherein the C$_{1-8}$ alkyl, C$_{2-8}$ alkenyl or C$_{2-8}$ alkynyl optionally has 1-2 heteroatoms independently selected from O, S and NH wherein each heteroatom replaces a CH$_2$, with the proviso that no O, S or N atom in the C$_{1-8}$ alkyl, C$_{2-8}$ alkenyl, or C$_{2-8}$ alkynyl is covalently bonded to another O, S or N atom;

R$^3$ is independently in each instance H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^4$ is independently in each instance H, OH, NO$_2$, NH$_2$, NH$_3^+$, SH, or a branched or unbranched C$_{1-10}$ alkyl, C$_{2-10}$ alkenyl, or C$_{2-10}$ alkynyl, wherein the C$_{1-10}$ alkyl, C$_{2-10}$ alkenyl or C$_{2-10}$ alkynyl is optionally substituted with 1-2 substituents independently selected from the group consisting of halo, OH, NO$_2$, NH$_2$, NH$_3^+$, SH, and =O, and wherein the C$_{1-10}$ alkyl, C$_{2-10}$ alkenyl, or C$_{2-10}$ alkynyl optionally has 1-2 heteroatoms independently selected from O, S and NH wherein each heteroatom replaces a CH$_2$, with the proviso that no O, S or N atom in the C$_{1-10}$ alkyl, C$_{2-10}$ alkenyl or C$_{2-10}$ alkynyl is covalently bonded to another O, S or N atom;

R$^5$ is H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^6$ and R$^7$ are each independently H or lower alkyl, optionally substituted with 1-3 substituents independently selected from the group consisting of halo, nitro, amine, amide, hydroxyl, O-lower alkyl and carboxy;

B is a covalent bond, O or NR$_1$;

p is 1, 2, 3, 4, 5, or 6; and n is 1, 2, 3, 4, 5, or 6.

The application also describes a non-covalently bound complex of the compound of Formula (I), Formula (II), and/or Formula (III), or pharmaceutically acceptable salt thereof, and human serum albumin in a molar ratio from about 1:1 to about 10:1, wherein the non-covalently bound complex has solubility in aqueous solution of at least 5 mg/mL.

Additionally provided is a pharmaceutical composition including a non-covalently bound complex as described herein, and a pharmaceutically acceptable carrier.

An aspect of the application is a method of treating prostate cancer, the method including the step of administering to the subject in need thereof a therapeutically effective amount of a pharmaceutical composition as described herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the disclosure will be apparent from the following detailed description, and from the claims.

DETAILED DESCRIPTION

Definitions

Figure 1:
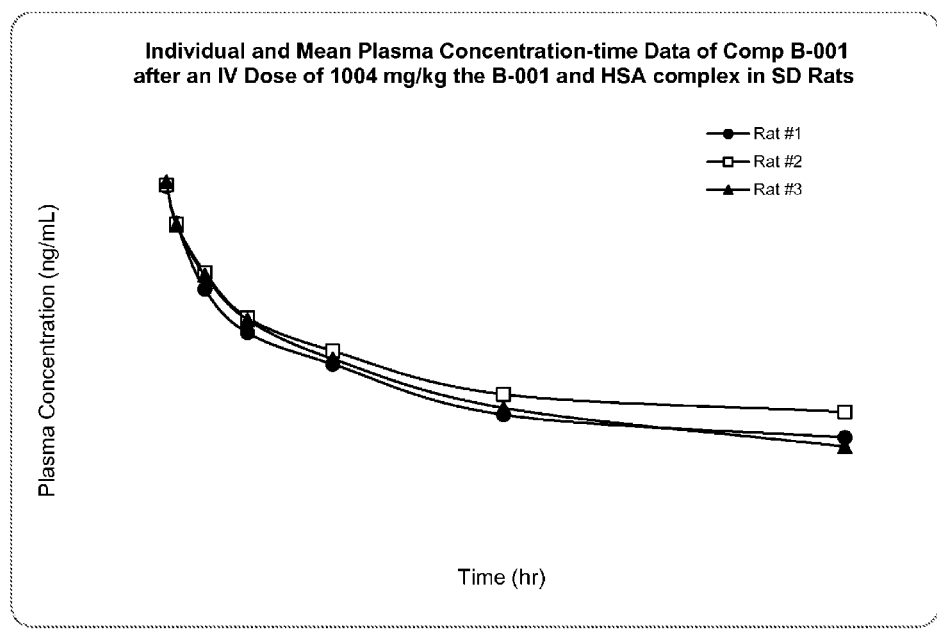
FIG. 1 shows individual and mean plasma concentration-time data for Compound B-001 after an IV dose of 1004 mg/kg of the Compound B-001-Human Serum Albumin (HSA) complex in Sprague Dawley® (SD) rats.

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

As used herein, chemical structures which contain one or more stereocenters depicted with dashed and bold bonds (i.e.,  and ) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "halo" refers to fluoro, chloro, bromo or iodo.

The term "alkyl" refers to a straight or branched chain alkyl group, having from 1-20 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "$C_{x-y}$ alkyl" refers to an alkyl group between x and y carbon atoms in size. For example, $C_{1-8}$ alkyl refers to an alkyl of 1 to 8 carbon atoms.

The term "alkaryl" represents an alkyl group substituted with an aryl group. Examples of alkaryl groups include benzyl, phenethyl, and 2-(naphthalen-1-yl)ethyl.

The term "($C_{x-y}$ alkyl)aryl" is an alkaryl group containing an alkyl group between x and y carbon atoms in size. For example, ($C_{1-3}$ alkyl)aryl refers to an alkyl of 1 to 3 carbon atoms attached to an aryl group.

The term "alkenyl" represents a straight or branched chain alkenyl group, having from 2 to 20 carbon atoms. It may have 1 or more double bonds. In some embodiments, the alkenyl group may have 2-6 double bonds. Examples of such groups include the vinyl, alkyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11, 14-nonadecatetraenyl, nonadecapentaenyl, henecosatetraenyl, henecosapentaenyl, henecosahexaenyl, myristyl, and eicosyl groups.

The term "$C_{x-y}$ alkenyl" refers to an alkenyl group between x and y carbon atoms in size. For example, $C_{2-8}$ alkenyl refers to an alkenyl of 2 to 8 carbon atoms.

The term "alkynyl" represents an alkynyl group having from 2 to 20 carbon atoms, and may be a straight or branched chain group. In addition to one or more triple bonds, the alkynyl group may have one or more double bonds.

The term "$C_{x-y}$ alkynyl" refers to an alkynyl group between x and y carbon atoms in size. For example, $C_{2-8}$ alkynyl refers to an alkynyl of 2 to 8 carbon atoms.

When specifically stated, alkyl, alkenyl, or alkynyl groups may include ring structures of 3 to 8 carbon atoms.

When an alkyl, alkenyl or alkynyl group is described as a "lower" alkyl, alkenyl or alkynyl group, it has a maximum of 6 carbon atoms.

When specifically stated, alkyl, alkenyl or alkynyl groups may include heteroatoms of oxygen, sulfur, nitrogen and/or silicon. Where specifically stated, alkyl, alkenyl or alkynyl groups may be substituted with halo, hydroxyl, nitro ($NO_2$), amine, amide, sulfhydryl (SH), O-lower alkyl and carboxy (COOH) groups. Illustrative examples of the alkyl group substituted with oxygen or including a heteroatom of oxygen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Illustrative examples of the alkyl group substituted with sulfur are methylthiomethyl, ethylthiomethyl, propylthiomethyl, n-butylthiomethyl, 2-methylthiolethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Illustrative examples of the alkyl group substituted with nitrogen are aminomethyl, dimethylaminomethyl, (N-acetyl)methylaminomethyl, diethylaminomethyl, dipropylaminomethyl, dibutylaminomethyl, dimethylaminoethyl, diethylaminoethyl, dipropylaminoethyl, and dibutylaminoethyl groups. Illustrative examples of the alkyl group substituted with silicon are trimethylsilyl, triethylsilyl, tributylsilyl, t-butyldimethylsilyl, t-butyldiethylsilyl and t-butyldiphenylsilyl.

The terms "amine" and "amino" are art-recognized and refer to both unsubstituted and substituted amines and salts thereof, e.g., a moiety that can be represented by the general formulae:

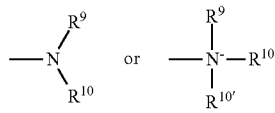

where $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In some embodiments, only one of $R^9$ or $R^{10}$ is a carbonyl, e.g., $R^9$, $R^{10}$, and the nitrogen together do not form an imide. In some embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning its protonated form has a $pK_a$ above 7.00.

The terms "amide" and "amido" are art-recognized as an amino-substituted carbonyl and include a moiety that can be represented by the general formula:

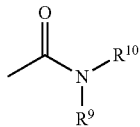

wherein $R^9$ and $R^{10}$ are as defined above. In some embodiments, the amide will not include imides, which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenol, aniline, and the like.

The terms "carbocycle" and "carbocyclyl" as used herein refer to a 3- to 6-membered non-aromatic substituted or unsubstituted ring in which each atom of the ring is carbon. The ring may be completely saturated or may have one or more unsaturated bonds such that the ring remains non-aromatic. Examples of carbocyclyls include cyclopropyl, cyclopentyl, cyclopentenyl, cyclohexyl, cyclohexenyl, cyclohexylmethyl, and 4-methylcyclohexyl.

The term "carbocyclylalkyl" refers to a carbocyclyl group substituted with an alkyl group.

The terms "sulfonamide" and "sulfonamido" are art-recognized as an amino-substituted sulfonyl and include a moiety that can be represented by the general formula:

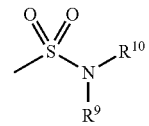

wherein $R^9$ and $R^{10}$ are as defined above.

The term "linker" as used herein refers to a group of atoms, e.g., 0-500 atoms, and may be comprised of the atoms or groups such as, but not limited to, carbon, amino, alkylamino, oxygen, sulfur, sulfoxide, sulfonyl, carbonyl, and imine. The linker chain may also include part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers. The linker must not interfere with binding of the ligand to the target.

In its simplest form, a linker can be a covalent chemical bond. In other embodiments, the linker can be a chemical group. Since the function of the linking group is merely to provide a physical connection, a wide variety of chemical groups can serve as linking groups. A linker is typically a divalent organic linking group where one valency represents the point of attachment to ligand or payload molecule and one valency represents the attachment to the compound. The only requirement for the linker is to provide a stable physical linkage that is compatible with maintaining the function of the ligand or payload molecule and is compatible with the chemistry. In some embodiments, the linking group includes a —S—S— moiety.

Examples of suitable linking groups include, e.g.: —O—, —S—, —S(O)—, —S(O)$_2$—, —S—S—, —C(O)—, —NH—, —N(C$_1$-C$_6$)alkyl, —NHC(O)—, —C(O)NH—, —O(CO)—, —C(O)O—, —O(CO)NH—, —NHC(O)O—, —O(CO)O—, —NHC(O)NH—, —O(C$_1$-C$_6$)alkylene-, —S(C$_1$-C$_6$)alkylene-, —S(O)(C$_1$-C$_6$)alkylene-, —S(O)$_2$(C$_1$-C$_6$)alkylene-, —C(O)(C$_1$-C$_6$)alkylene-, —NH((C$_1$-C$_6$)alkylene)C(O)—, —C(O)((C$_1$-C$_6$)alkylene)C(O)—, —C(O)((C$_1$-C$_6$)alkylene)NH—, —O(CO)—, —C(O)O—, —O(CO)NH—, —NHC(O)O—, —O(CO)O—, —NHC(O)NH—, unsubstituted-(C$_1$-C$_{10}$)alkylene-, unsubstituted-(C$_1$-C$_{10}$)heteroalkylene, or —(C$_1$-C$_{10}$)alkylene or —(C$_1$-C$_{10}$)heteroalkylene substituted with one or more (e.g., 1, 2, 3, 4 or 5 substituents) independently selected from the group consisting of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_1$-C$_6$)alkylene)Ar, —O((C$_1$-C$_6$)alkylene)Ar, —OC(=O)(C$_1$-C$_6$)alkyl, —OC(=O)O(C$_1$-C$_6$)alkyl, —OC(=O)NR$_2$, —NR$_2$, —NRAr, —NR((C$_1$-C$_6$)alkylene)Ar, —NRC(=O)R, —NRC(=O)Ar, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$, oxo and sulfido, wherein each R group is hydrogen or (C$_1$-C$_6$ alkyl), e.g., methyl and wherein each Ar is independently unsubstituted aryl or heteroaryl or aryl or heteroaryl substituted with one or more of $(C_1-C_6)$ alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —OR, —OC(=O)($C_1-C_6$) alkyl, —OC(=O)O($C_1-C_6$)alkyl, —OC(=O)NR$_2$, —NR$_2$, —NRC(=O)R, —NRC(=O)O($C_1-C_6$)alkyl, —NRC(=O)NR$_2$, —NRSO$_2$R, —SR, —S(O)R, —SO$_2$R, —OSO$_2$($C_1-C_6$)alkyl, —SO$_2$NR$_2$, $(C_1-C_8)$perfluoroalkyl, —$(C_2-C_6)$alkylene-OR, —O$(C_2-C_6)$alkylene-N($(C_1-C_6)$alkyl)$_2$, —P(=O)(OR)$_2$, —OP(=O)(OR)$_2$ wherein each R group is hydrogen or $(C_1-C_6$ alkyl). In addition, —$(C_1-C_{10})$alkylene- and —$(C_1-C_{10})$heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$O—, where n is an integer, e.g., 1, 2, 3, 4 or 5). The —$(C_1-C_{10})$alkylene- and —$(C_1-C_{10})$heteroalkylene also include —$(C_1-C_6)$alkylene- and $(C_1-C_6)$heteroalkylene; and —$(C_1-C_3)$alkylene- and —$(C_1-C_3)$heteroalkylene.

The term "group of natural amino acid side chains" represents the set of chemical groups attached to the alpha carbon for each of the twenty naturally-occurring amino acids: Cysteine, Histidine, Isoleucine, Methionine, Serine, Valine, Alanine, Glycine, Leucine, Proline, Threonine, Phenylalanine, Arginine, Tyrosine, Tryptophan, Aspartic Acid, Asparagine, Glutamic Acid, Glutamine and Lysine.

As used herein, "solubility in aqueous solution of at least X mg/mL" refers to a composition that forms an optically clear solution at room temperature in water, without additional, non-water, solvents.

As used herein, "substantially free of solvent", in reference to an aqueous solution, refers to an aqueous solution that contains less than 0.5%, by weight, of any non-water solvent.

As used herein, "a group that selectively binds to serum albumin" refers to a chemical group suitable for administration to a mammal, for example, a human, which exhibits binding affinity for serum albumin. Examples of such groups that selectively bind to serum albumin include, but are not limited to, long chain fatty acids ($C_{16}-C_{20}$; including oleic, palmitic, linoleic, stearic, arachidonic, and palmitoleic); medium chain fatty acids ($C_6-C_{14}$; including caprylate or octanoate); phospholipids (lysolecithins, oleoyllysophosphatidic acid, phosphatidylcholine, phosphatidylethanolamine); eicosanoid derivatives (leukotrienes, thromboxanes, prostaglandins A, E, F, and I); steroid hormones (cholesterol, testosterone, pregnenolone, cortisol, androsterone, indol, progesterone, estrogen); vitamin D (both monohydroxyvitamin D and dihydroxyvitamin D); bile salts (lithocholate, chenodeoxycholate, deoxycholate, ursodeoxycholate, cholate, glycolitocholate, glycochenodeoxycholate, taurochenodoxycholate, glycodeoxycholate, glycocholate, taurocholate); bilirubins (bilirubin, biliverdin, xanthobilirubin, EZ-cyclobilirubin, δ-bilirubin); porphyrins (hematin, protoporphyrin); warfarin; salicylates, ibuprofen; prednisone; iophenoxate; sulfisoxazole; phenylbutazone; oxphenylbutazone; digitoxin; indomethacin; tolbutamide; furosemide; phenyloin; chlorpropamide; chlorthiazide; the penicillins (including oxacillin, benzylpenicillin); acetotrizoate; isulfobromophthalein; deacetylcolchicine; dansylamide; dansylglutamine; dansylsarcosine; indomethacin; phenylpropazone; azobenzene derivatives; sulfobromophthalein; triiodobenzoate; benzodiazepine (including diazepam); flufenamate; iopanoate; ethacrynate; panproxen; clofibrate; L-tryptophan; N-acetyl-L-tryptophan; 6-methyl-tryptophan; thyroxine; 3,5,3'-L-triiodothyronine; indole propionate; kynurenine; ethacrynate; panproxen; chlorophenoxyisobutyrate; 3' azido-3'-deoxythymidine; non-steroidal anti-inflammatory agents containing ionized carboxyl groups; gossypol; meso-2,3-dimercaptosuccinic acid; captopril; N2-mercaptoethyl-1,2-diaminopropane; disulfuramacetaminophen, dis-dichlorodiamineplatinum 9II; pyridoxal 5'-phosphate; aquocobalamin form of vitamin B12; folate; ascorbate (and its oxidation product dehydroascorbate); melatonin; α-melanotropin; gastrin; corticotropin and methotrexate. The group that selectively binds to serum albumin may bind to serum albumin at specific, defined sites, as detailed by crystallographic and displacement studies, and may also bind serum albumin at non-specific sites that have yet to be clearly defined. Binding between the group that selectively binds serum albumin and serum albumin occurs by non-covalent mechanisms. These groups selectively bind serum albumin in that when added to mammalian blood, they bind in greatest quantity to serum albumin over other blood proteins. One of skill in the art of pharmacology is well able to envision and use a wide variety of groups that selectively bind serum albumin due to their familiarity with the literature showing many pharmaceutical compounds which preferentially bind serum albumin in mammals. See, for example, F. Kratz, et al, *Journal of Controlled Release* 2008, 132:171-183.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient.

As used herein, the term "cancer" refers to all known forms of cancer including, solid forms of cancer (e.g., tumors), lymphomas, and leukemias.

As used herein, an "effective amount" or a "pharmaceutically-effective amount" in reference to the compounds or compositions of the present disclosure refers to the amount sufficient to induce a desired biological, pharmacological, or therapeutic outcome in a subject. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, prevention, mitigation, limitation, and/or, delay of the deleterious physiological manifestations, growth or metastases of neoplasms.

Compounds

Provided herein are compounds having a structure of Formula (I):

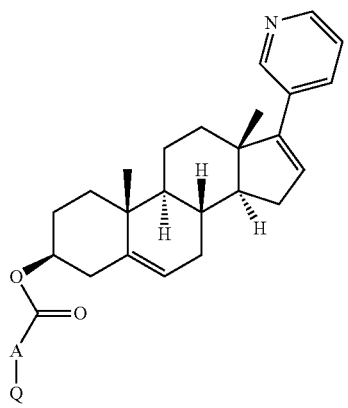

(I)

wherein

A is a covalent bond, O, or $NR^1$;

$R^1$ is H, lower alkyl, or alkaryl, wherein the alkyl or alkaryl is optionally substituted with 1-3 substituents independently selected from the group consisting of: halo, nitro, amine, amide, hydroxyl, O-lower alkyl, and carboxy; and Q is a group that selectively binds to human serum albumin.

In some embodiments, $R^1$ is H or lower alkyl. For example, $R^1$ can be H.

In some embodiments, Q includes —COOH.

In some embodiments, Q includes a —S—S— moiety.

In some embodiments, the compound of Formula (I) has the structure of Formula (II):

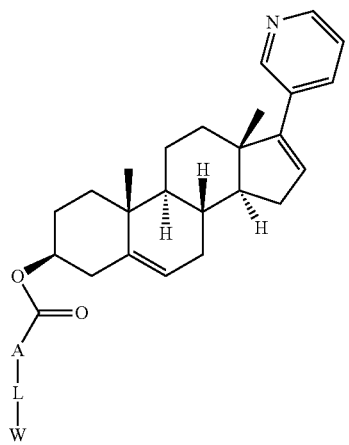

(II)

wherein

A is a covalent bond, O or $NR^1$;

L is alkyl, alkyl-O-alkyl, alkenyl, alkynyl, carbocyclyl, carbocyclylalkyl, aryl, alkaryl, or

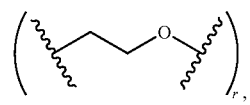

each of which is optionally substituted with 1-3 substituents independently selected from the group consisting of halo, —$NO_2$, amine, amide, hydroxyl, O-lower alkyl, and —COOH, provided that there be no covalent bonds between oxygen atoms;

W is

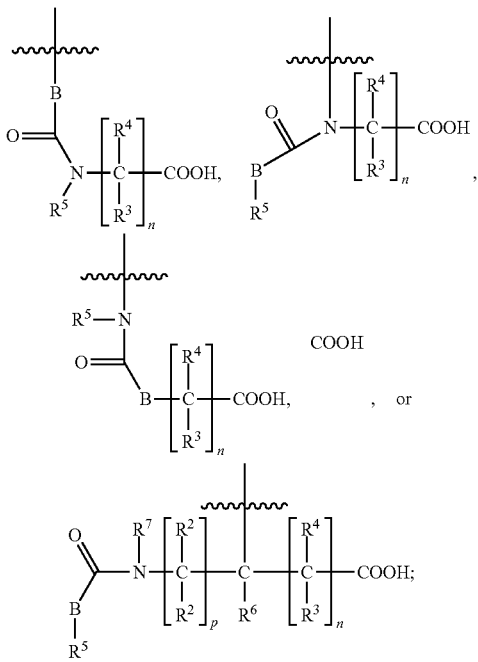

$R^1$ is H, lower alkyl, or alkaryl, wherein the alkyl or alkaryl is optionally substituted with 1-3 substituents independently selected from the group consisting of: halo, NO$_2$, amine, amide, hydroxyl, O-lower alkyl and —COOH;

R$^2$ is independently in each instance H, OH, NO$_2$, NH$_2$, NH$_3^+$, SH, or a branched or unbranched C$_{1-8}$ alkyl, C$_{2-8}$ alkenyl or C$_{2-8}$ alkynyl, wherein the C$_{1-8}$ alkyl, C$_{2-8}$ alkenyl or C$_{2-8}$ alkynyl is optionally substituted with 1-2 substituents independently selected from the group consisting of halo, OH, NO$_2$, NH$_2$, NH$_3^|$, SH, and =O, and wherein the C$_{1-8}$ alkyl, C$_{2-8}$ alkenyl or C$_{2-8}$ alkynyl optionally has 1-2 heteroatoms independently selected from O, S and NH wherein each heteroatom replaces a CH$_2$, with the proviso that no O, S or N atom in the C$_{1-8}$ alkyl, C$_{2-8}$ alkenyl or C$_{2-8}$ alkynyl is covalently bonded to another O, S or N atom;

R$^3$ is independently in each instance H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^4$ is independently in each instance H, OH, NO$_2$, NH$_2$, NH$_3^+$, SH, or a branched or unbranched C$_{1-10}$ alkyl, C$_{2-10}$ alkenyl, or C$_{2-10}$ alkynyl, wherein the C$_{1-10}$ alkyl, C$_{2-10}$ alkenyl or C$_{2-10}$ alkynyl is optionally substituted with 1-2 substituents independently selected from the group consisting of halo, OH, NO$_2$, NH$_2$, NH$_3^+$, SH, and =O, and wherein the C$_{1-10}$ alkyl, C$_{2-10}$ alkenyl or C$_{2-10}$ alkynyl optionally has 1-2 heteroatoms independently selected from O, S, and NH wherein each heteroatom replaces a CH$_2$, with the proviso that no O, S, or N atom in the C$_{1-10}$ alkyl, C$_{2-10}$ alkenyl or C$_{2-10}$ alkynyl is covalently bonded to another O, S, or N atom;

R$^5$ is H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

R$^6$ and R$^7$ are each independently H or lower alkyl, optionally substituted with 1-3 substituents independently selected from the group consisting of halo, nitro, amine, amide, hydroxyl, O-lower alkyl, and carboxy;

B is a covalent bond, O or NR$^1$;

the wavy line indicates the point of W to L;

p is 1, 2, 3, 4, 5, or 6;

n is 1, 2, 3, 4, 5, or 6; and r is 1, 2, 3, 4, 5, 6, 7, 8, 9, or 10.

In some embodiments, a compound of Formula (I) has the structure of Formula (III):

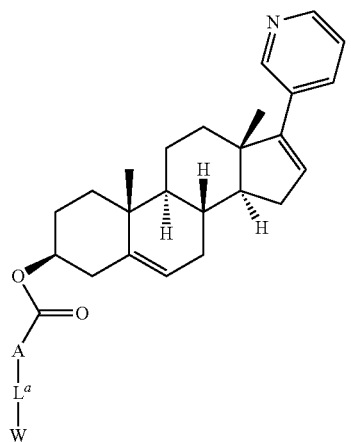

(III)

wherein

A is a covalent bond, O or NR$^1$;

L$^a$ is a linker including a —S—S— moiety;

W is

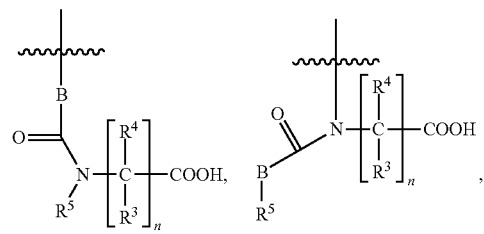

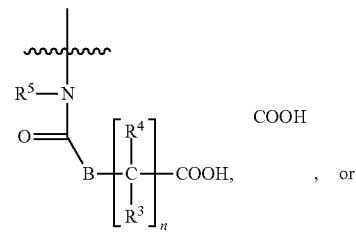

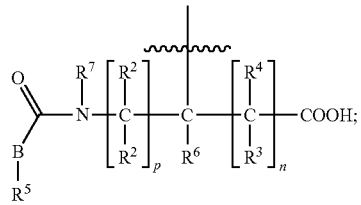

R$^1$ is H, lower alkyl, or alkaryl, wherein the alkyl or alkaryl is optionally substituted with 1-3 substituents independently selected from the group consisting of: halo, NO$_2$, amine, amide, hydroxyl, O-lower alkyl, and —COOH;

R$^2$ is independently in each instance H, OH, NO$_2$, NH$_2$, NH$_3^+$, SH, or a branched or unbranched C$_{1-8}$ alkyl, C$_{2-8}$ alkenyl or C$_{2-8}$ alkynyl, wherein the C$_{1-8}$ alkyl, C$_{2-8}$ alkenyl or C$_{2-8}$ alkynyl is optionally substituted with 1-2 substituents independently selected from the group consisting of halo, OH, NO$_2$, NH$_2$, NH$_3^+$, SH, and =O, and wherein the C$_{1-8}$ alkyl, C$_{2-8}$ alkenyl, or C$_{2-8}$ alkynyl optionally has 1-2 heteroatoms independently selected from O, S, and NH wherein each heteroatom replaces a CH$_2$, with the proviso that no O, S, or N atom in the C$_{1-8}$ alkyl, C$_{2-8}$ alkenyl, or C$_{2-8}$ alkynyl is covalently bonded to another O, S, or N atom;

R$^3$ is independently in each instance H, alkyl, phenyl, or alkaryl, wherein the alkyl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

$R^4$ is independently in each instance H, OH, $NO_2$, $NH_2$, $NH_3^+$, SH or a branched or unbranched $C_{1-10}$ alkyl, $C_{2-10}$ alkenyl, or $C_{2-10}$ alkynyl, wherein the $C_{1-10}$ alkyl, $C_{2-10}$ alkenyl or $C_{2-10}$ alkynyl is optionally substituted with 1-2 substituents independently selected from the group consisting of halo, OH, $NO_2$, $NH_2$, $NH_3^+$, SH, and =O, and wherein the $C_{1-10}$ alkyl, $C_{2-10}$ alkenyl or $C_{2-10}$ alkynyl optionally has 1-2 heteroatoms independently selected from O, S, and NH wherein each heteroatom replaces a $CH_2$, with the proviso that no O, S, or N atom in the $C_{1-10}$ alkyl, $C_{2-10}$ alkenyl, or $C_{2-10}$ alkynyl is covalently bonded to another O, S, or N atom;

$R^5$ is H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl;

$R^6$ and $R^7$ is each independently H or lower alkyl, optionally substituted with 1-3 substituents independently selected from the group consisting of halo, nitro, amine, amide, hydroxyl, O-lower alkyl, and carboxy;

B is a covalent bond, O or $NR_1$;

the wavy line indicates the point of W to $L^a$;

p is 1, 2, 3, 4, 5, or 6; and n is 1, 2, 3, 4, 5, or 6.

In some embodiments, A is a covalent bond. In some embodiments, A is O. In some embodiments, A is $NR^1$.

In some embodiments, L is alkyl, alkenyl, alkynyl, carbocyclyl, carbocyclylalkyl, aryl, alkaryl, or

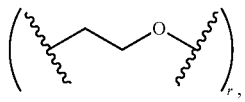

each of which is optionally substituted with 1-3 substituents independently selected from the group consisting of halo, —$NO_2$, amine, amide, hydroxyl, O-lower alkyl and —COOH, provided that there be no covalent bonds between oxygen atoms. In some embodiments, L is an alkyl, an alkenyl, or alkynyl, wherein the alkyl, alkenyl, or alkynyl is optionally substituted with 1-3 substituents independently selected from the group consisting of halo, —$NO_2$, amine, amide, hydroxyl, O-lower alkyl, and —COOH. In some embodiments, L is an alkyl, optionally substituted with 1-3 substituents independently selected from the group consisting of halo, —$NO_2$, amine, amide, hydroxyl, O-lower alkyl and —COOH. In some embodiments, L is an alkyl, optionally substituted with 1-3 substituents independently selected from the group consisting of halo, amine, amide, hydroxyl, O-lower alkyl and —COOH.

In some embodiments, $L^a$ is

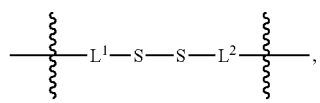

wherein $L^1$ is alkyl, alkyl-O-alkyl, alkenyl, alkynyl, carbocyclyl, carbocyclylalkyl, aryl, alkaryl, or

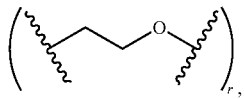

each of which is optionally substituted with 1-3 substituents independently selected from the group consisting of halo, —$NO_2$, amine, amide, hydroxyl, O-lower alkyl, and —COOH, provided that there be no covalent bonds between oxygen atoms; and $L^2$ is alkyl, alkyl-O-alkyl, alkenyl, alkynyl, carbocyclyl, carbocyclylalkyl, aryl, alkaryl, or

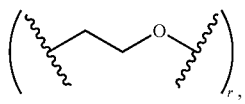

each of which is optionally substituted with 1-3 substituents independently selected from the group consisting of halo, —$NO_2$, amine, amide, hydroxyl, O-lower alkyl, and —COOH; and r is 1, 2, 3, 4, 5, 6, 7, 8, 9, or 10, provided that there be no covalent bonds between oxygen atoms.

In some embodiments, $L^1$ is an alkyl, alkyl-O-alkyl, alkaryl, or aryl, wherein the alkyl, alkyl-O-alkyl, alkaryl, or aryl is optionally substituted with 1-3 substituents independently selected from the group consisting of halo, —$NO_2$, amine, amide, hydroxyl, O-lower alkyl, and —COOH. In some embodiments, $L^1$ is an alkyl, optionally substituted with 1-3 substituents independently selected from the group consisting of halo, amine, amide, hydroxyl, O-lower alkyl, and —COOH. In some embodiments, $L^1$ is an alkyl, optionally substituted with 1-3 substituents independently selected from the group consisting of halo and O-lower alkyl. In some embodiments, $L^1$ is a $C_{1-6}$ alkyl. For example, $L^1$ can be —$CH_2$—$CH_2$—.

In some embodiments, $L^2$ is an alkyl, alkyl-O-alkyl, alkaryl, or aryl, wherein the alkyl, alkaryl, or aryl is optionally substituted with 1-3 substituents independently selected from the group consisting of halo, —$NO_2$, amine, amide, hydroxyl, O-lower alkyl and —COOH. In some embodiments, $L^2$ is an alkyl, optionally substituted with 1-3 substituents independently selected from the group consisting of halo, amine, amide, hydroxyl, O-lower alkyl and —COOH. In some embodiments, $L^2$ is an alkyl, optionally substituted with 1-3 substituents independently selected from the group consisting of halo and O-lower alkyl. In some embodiments, $L^2$ is a $C_{1-6}$ alkyl. For example, $L^2$ can be —$CH_2$—$CH_2$—.

In some embodiments, $L^1$ is an alkyl or aryl, wherein the alkyl or aryl is optionally substituted with 1-3 substituents independently selected from the group consisting of halo, —$NO_2$, amine, amide, hydroxyl, O-lower alkyl, and —COOH; and $L^2$ is an alkyl or aryl, wherein the alkyl or aryl is optionally substituted with 1-3 substituents independently selected from the group consisting of halo, —$NO_2$, amine, amide, hydroxyl, O-lower alkyl and —COOH.

In some embodiments, $L^1$ is an alkyl, optionally substituted with 1-3 substituents independently selected from the group consisting of halo, amine, amide, hydroxyl, O-lower alkyl and —COOH; and $L^2$ is an alkyl, optionally substituted with 1-3 substituents independently selected from the group consisting of halo, amine, amide, hydroxyl, O-lower alkyl and —COOH.

In some embodiments, W is

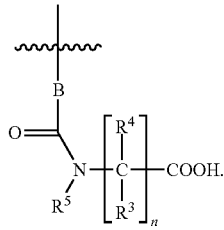

In some embodiments, W is

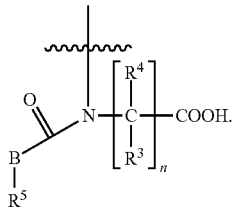

In some embodiments, W is

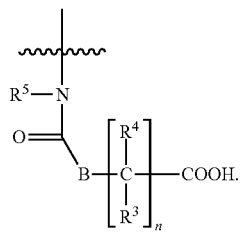

In some embodiments, W is

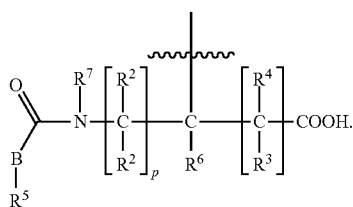

In some embodiments, W is

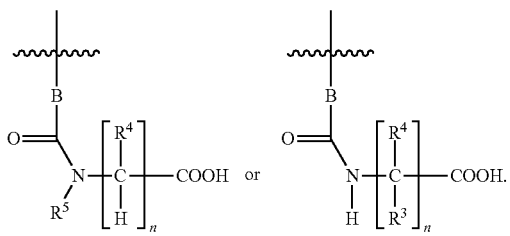

In some embodiments, W is

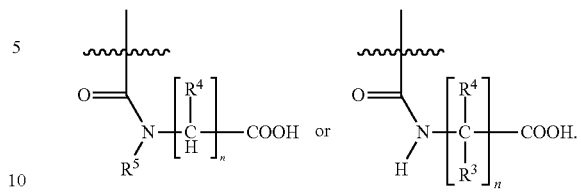

In some embodiments, W is COOH.

In some embodiments, $R^1$ is H or lower alkyl, optionally substituted with 1-3 substituents independently selected from the group consisting of: halo, $NO_2$, amine, amide, hydroxyl, O-lower alkyl, and —COOH. In some embodiments, $R^1$ is alkaryl, optionally substituted with 1-3 substituents independently selected from the group consisting of: halo, $NO_2$, amine, amide, hydroxyl, O-lower alkyl and —COOH.

In some embodiments, $R^1$ is benzyl.

In some embodiments, $R^1$ is H or lower alkyl.

In some embodiments, $R^1$ is H.

In some embodiments, $R^2$ is independently in each instance H, OH, $NO_2$, $NH_2$, $NH_3^+$, SH, or a branched or unbranched $C_{1-8}$ alkyl, $C_{2-8}$ alkenyl, or $C_{2-8}$ alkynyl, wherein the $C_{1-8}$ alkyl, $C_{2-8}$ alkenyl, or $C_{2-8}$ alkynyl is optionally substituted with 1-2 substituents independently selected from the group consisting of halo, OH, $NO_2$, $NH_2$, $NH_3^+$, SH, and =O.

In some embodiments, $R^2$ is H.

In some embodiments, $R^3$ is independently in each instance H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl.

In some embodiments, $R^3$ is independently in each instance H, $C_{1-8}$ alkyl, or ($C_{1-3}$ alkyl)aryl, wherein the $C_{1-8}$ alkyl or ($C_{1-3}$ alkyl)aryl is optionally substituted with 1-3 substituents independently selected from the group consisting of: halo, —$CF_3$, amido, sulfonamide, aryl, —OH, alkyl, —O-lower alkyl, —O-alkaryl, and —O-aryl.

In some embodiments, $R^3$ is independently in each instance $C_{1-6}$ alkyl or ($C_{1-3}$ alkyl)aryl optionally substituted with 1-3 substituents independently selected from the group consisting of: halo, —$CF_3$, aryl, —OH, alkyl, —O-lower alkyl, —O-alkaryl, and —O-aryl.

In some embodiments, $R^3$ is ($C_{1-3}$ alkyl)aryl.

In some embodiments, $R^3$ is benzyl.

In some embodiments, $R^4$ is independently in each instance H, OH, $NO_2$, $NH_2$, $NH_3^+$, SH or a branched or unbranched $C_{1-8}$ alkyl, $C_{2-8}$ alkenyl or $C_{2-8}$ alkynyl, wherein the $C_{1-8}$ alkyl, $C_{2-8}$ alkenyl or $C_{2-8}$ alkynyl is optionally substituted with 1-2 substituents independently selected from the group consisting of halo, OH, $NO_2$, $NH_2$, $NH_3^+$, SH, and =O. For example, $R^4$ can be H.

In some embodiments, $R^4$ is H or lower alkyl.

In some embodiments, $R^5$ is H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl.

In some embodiments, $R^5$ is H, $C_{1-8}$ alkyl, or ($C_{1-3}$ alkyl)aryl, wherein the $C_{1-8}$ alkyl or ($C_{1-3}$ alkyl)aryl is optionally substituted with 1-3 substituents independently selected from the group consisting of: halo, —$CF_3$, amido, sulfonamide, aryl, —OH, alkyl, —O-lower alkyl, —O-alkaryl, and —O-aryl.

In some embodiments, $R^5$ is $C_{1-6}$ alkyl or ($C_{1-3}$ alkyl)aryl optionally substituted with 1-3 substituents independently selected from the group consisting of: halo, —$CF_3$, aryl, alkyl, —O-lower alkyl, —O-alkaryl, and —O-aryl.

In some embodiments, $R^5$ is ($C_{1-3}$ alkyl)aryl. In some embodiments, $R^5$ is benzyl.

In some embodiments, $R^6$ is H or lower alkyl. For example, $R^6$ can be H.

In some embodiments, $R^7$ is H or lower alkyl. For example, $R^7$ can be H.

In some embodiments, B is a covalent bond. In some embodiments, B is O. In some embodiments, B is $NR^1$.

In some embodiments, n is 1, 2, 3, 4, 5, or 6. In some embodiments, n is 1, 2, 3, or 4. In some embodiments, n is 1, or 2. In some embodiments, n is 1. In some embodiments, n is 2.

In some embodiments, r is 1, 2, 3, 4, 5, 6, 7, 8, 9, or 10.

In some embodiments, the compound of Formula (I) and/or Formula (II) has the structure:

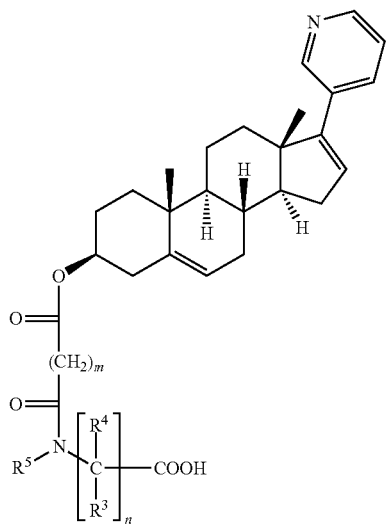

wherein
m is 1, 2, 3, 4, 5, 6, 7, or 8.

In some embodiments, m is 1, 2, 3, or 4. In some embodiments, m is 2. In some embodiments, m is 3.

In some embodiments, the compound of Formula (I) and/or Formula (II) has the structure:

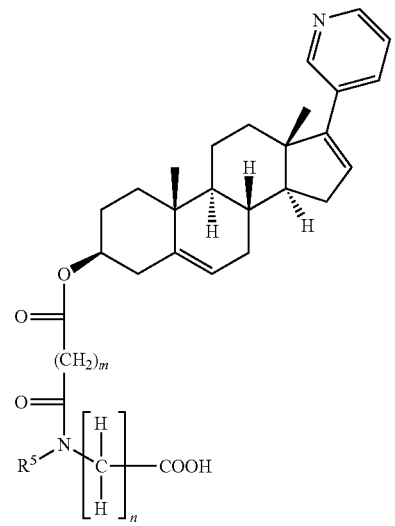

wherein m is 1, 2, 3, 4, 5, 6, 7, or 8.

In some embodiments, the compound of Formula (I) and/or Formula (II) has the structure:

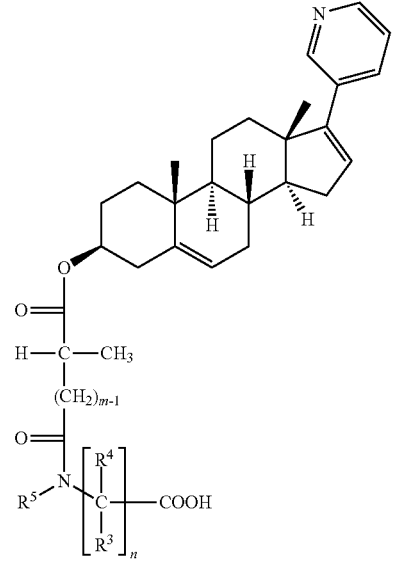

wherein m is 1, 2, 3, 4, 5, 6, 7, or 8.

In some embodiments, m is 1, 2, 3, or 4. In some embodiments, m is 2. In some embodiments, m is 3.

In some embodiments, the compound of Formula (I) and/or Formula (II) has the structure:

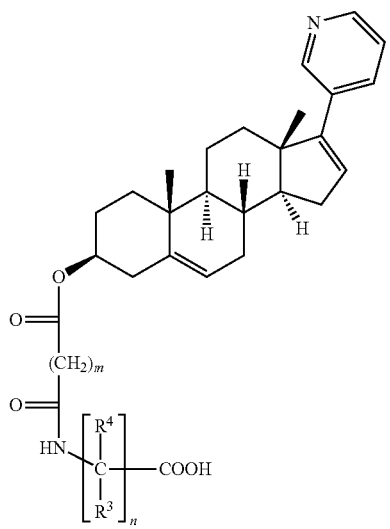

wherein m is 1, 2, 3, 4, 5, 6, 7, or 8.

In some embodiments, m is 1, 2, 3, or 4. In some embodiments, m is 2. In some embodiments, m is 3. In some embodiments, m is 2 or 3. For example, m can be 2.

In some embodiments, n is 1, 2, 3, 4, 5, or 6. In some embodiments, n is 2 or 3. For example, n can be 2. In some embodiments, n is 1.

In some embodiments, m is 2 or 3; and n is 1, 2, or 3. In some embodiments, m is 2 or 3; and n is 2 or 3. In some embodiments, m is 2 or 3; and n is 1 or 2. In some embodiments, m is 2; and n is 1.

In some embodiments, the compound of Formula (I) and/or Formula (II), or a pharmaceutically acceptable salt thereof, has a structure selected from:

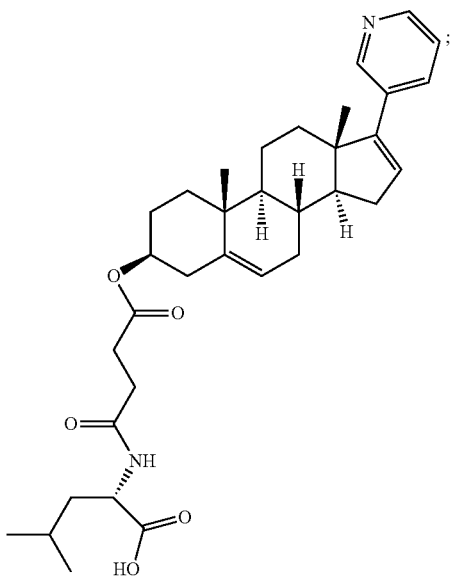

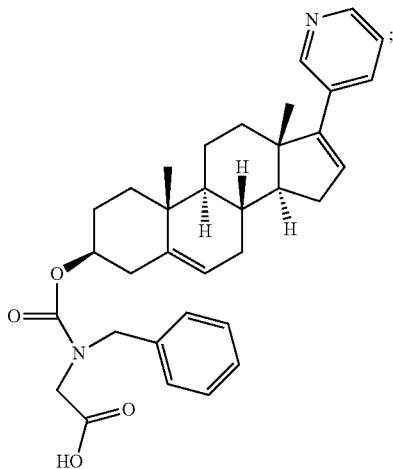

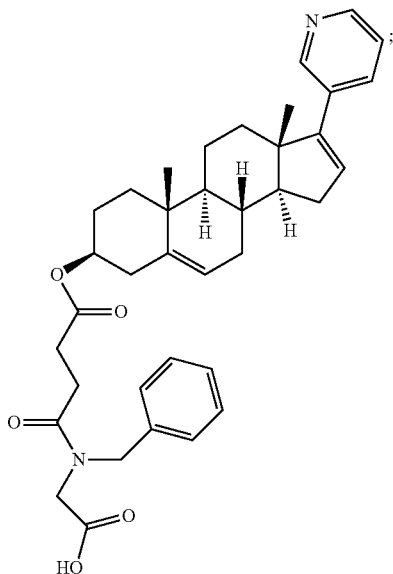

25
-continued
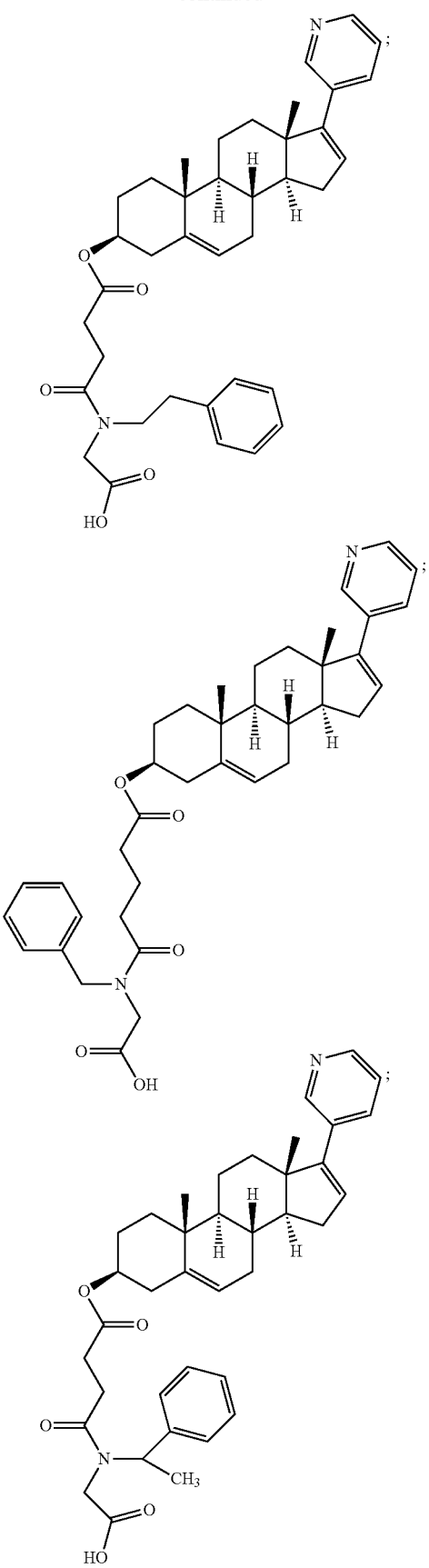
26
-continued
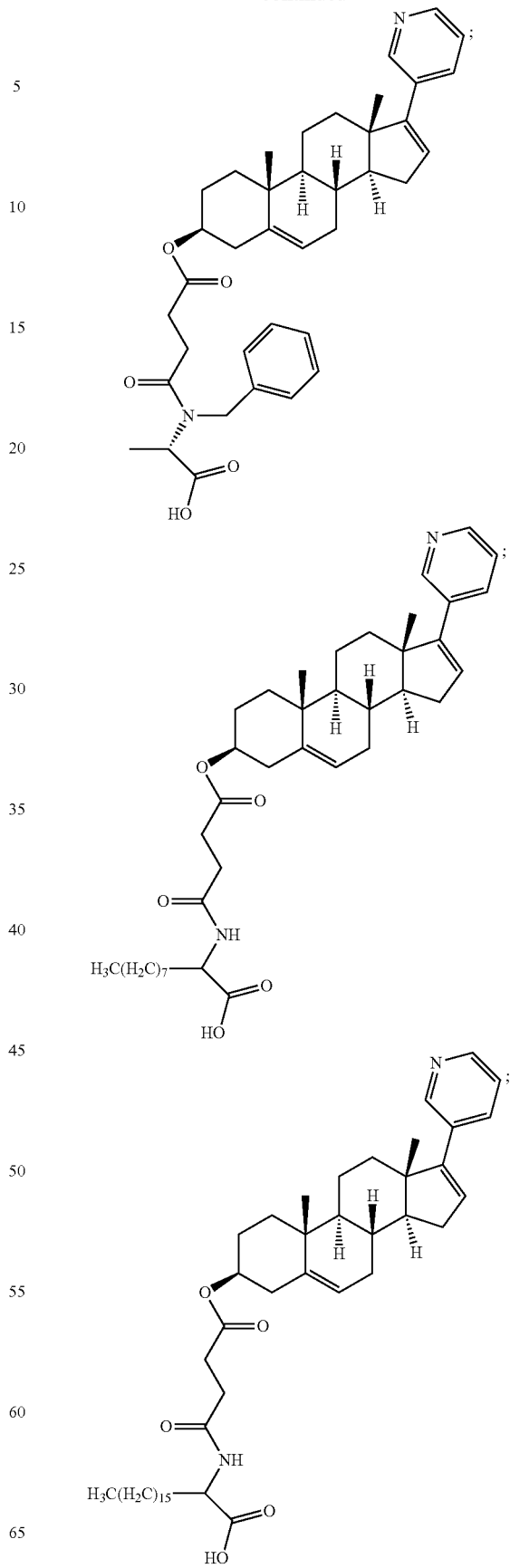

27
-continued
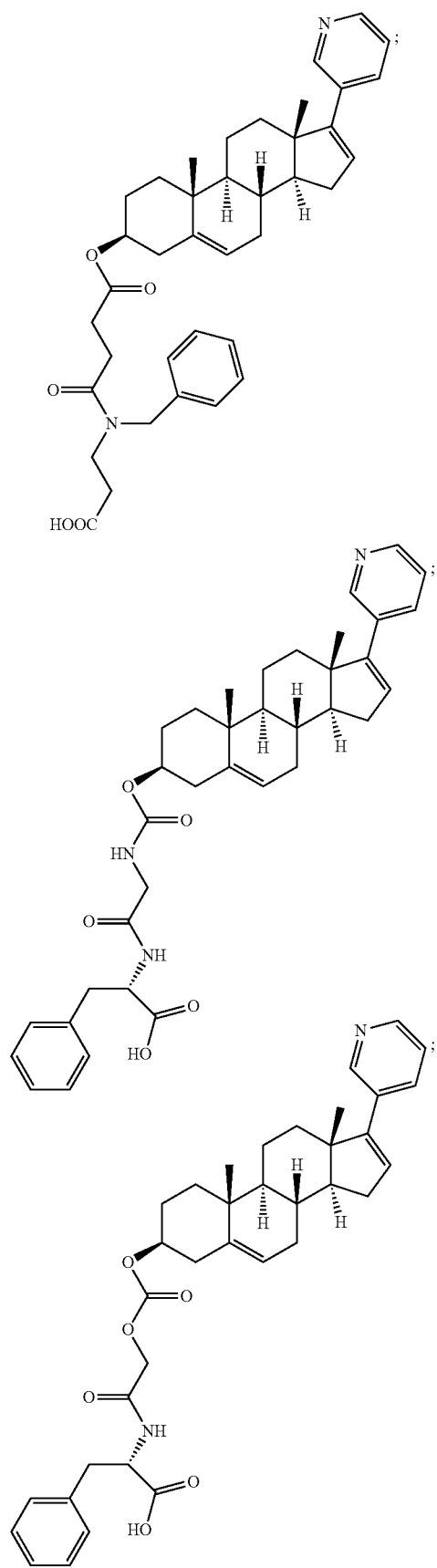
28
-continued
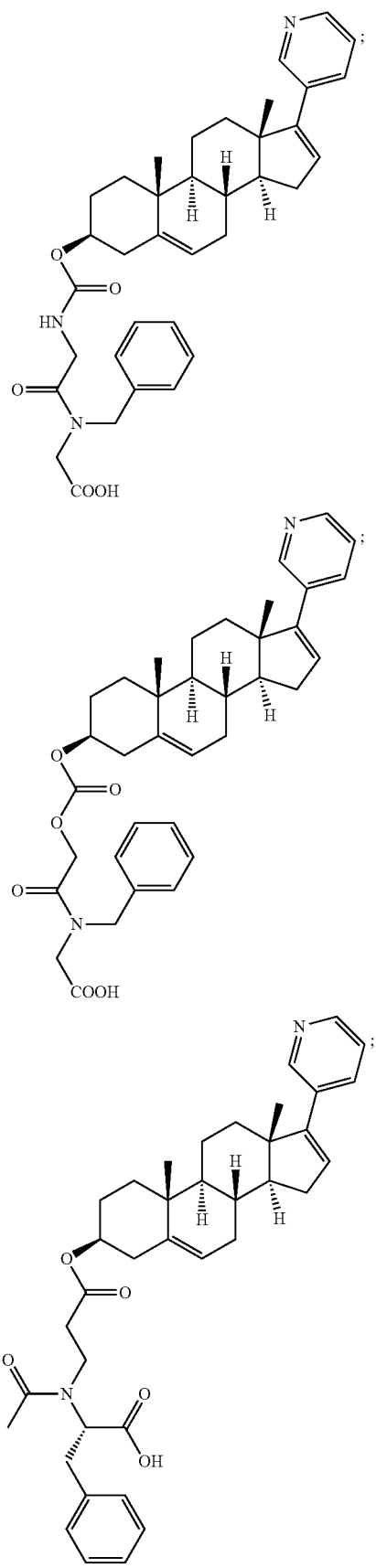

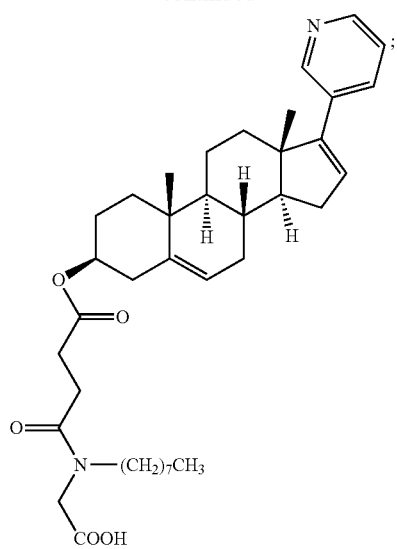
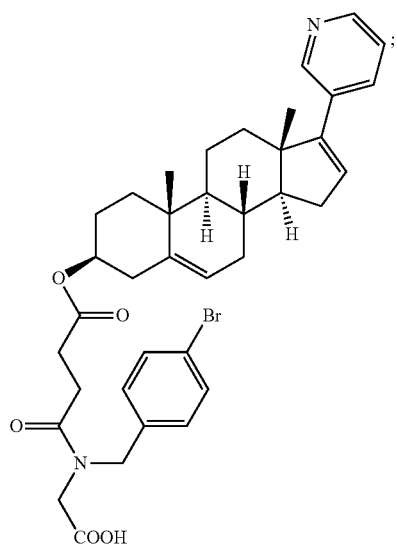
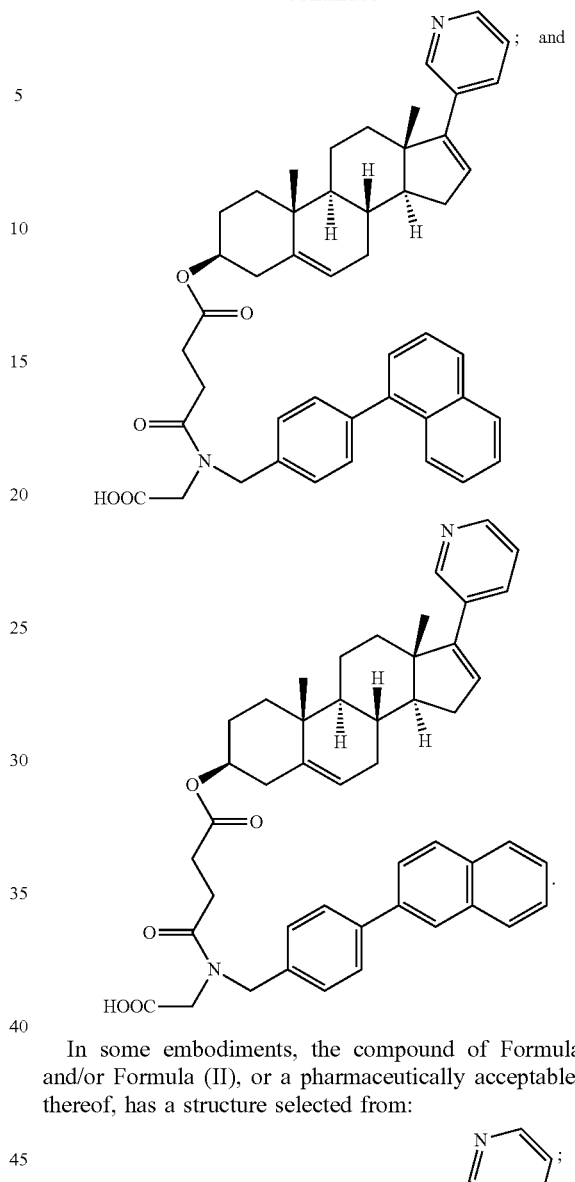
In some embodiments, the compound of Formula (I) and/or Formula (II), or a pharmaceutically acceptable salt thereof, has a structure selected from:

31
-continued
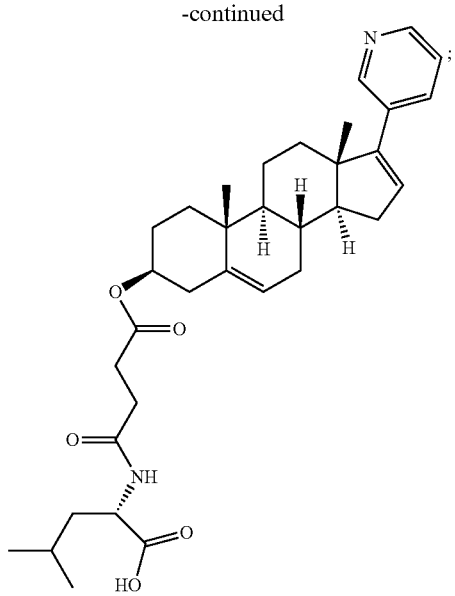
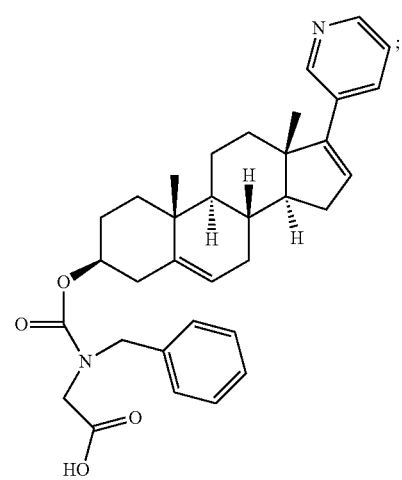
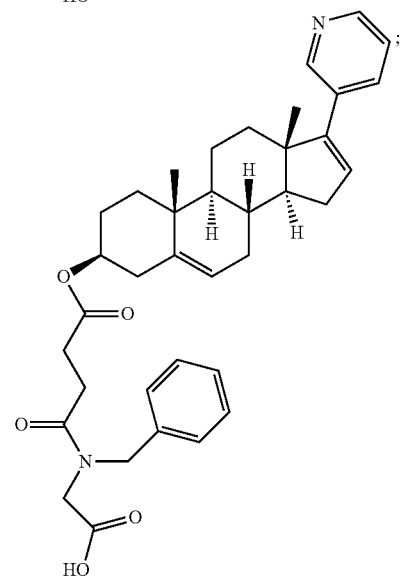
32
-continued
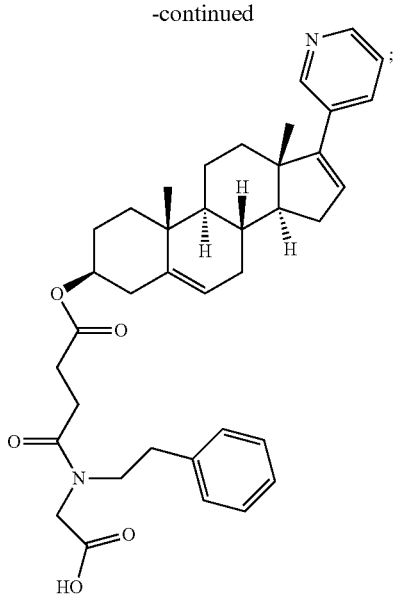
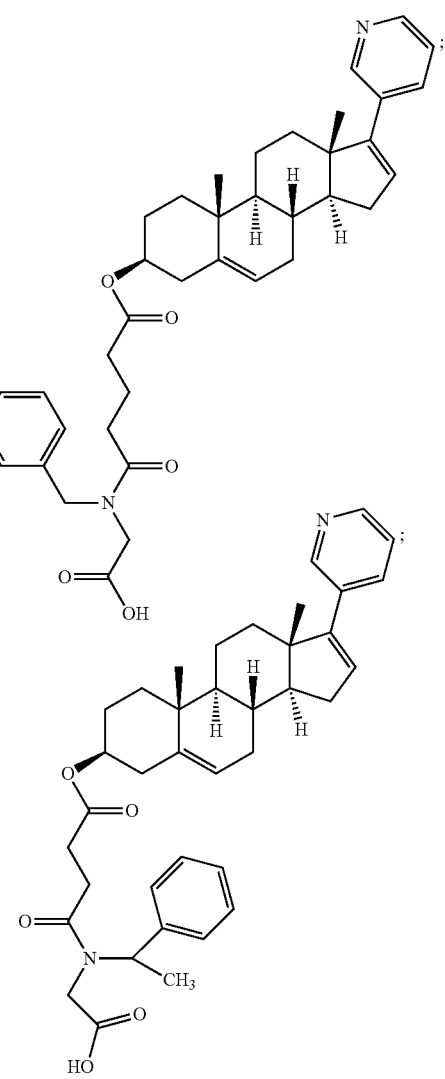

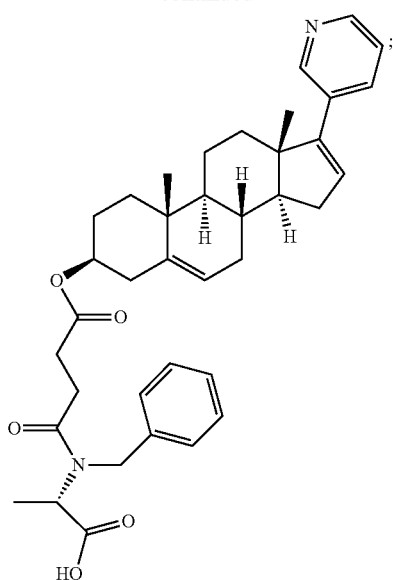
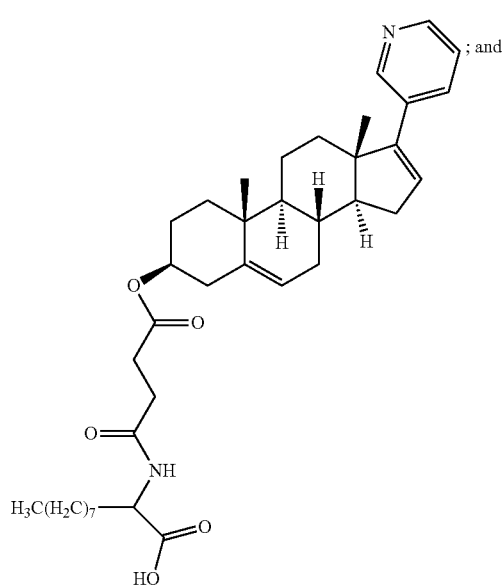
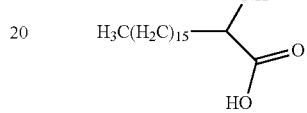
In some embodiments, the compound of Formula (I) and/or Formula (III) has the structure:
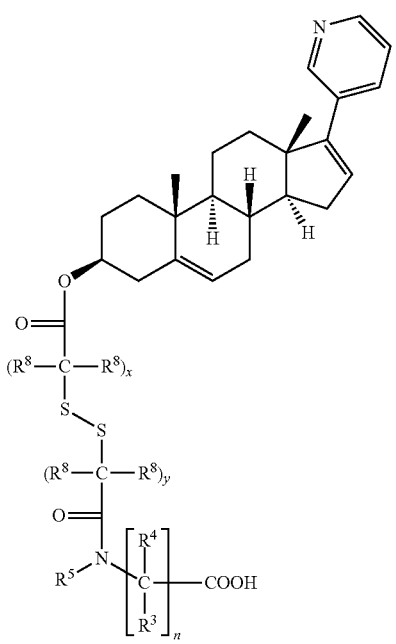
wherein
$R^8$ is each independently H or lower alkyl;
x is 1, 2, 3, 4, 5, 6, 7, or 8; and
y is 1, 2, 3, 4, 5, 6, 7, or 8.

In some embodiments, the compound of Formula (I) and/or Formula (III) has the structure:

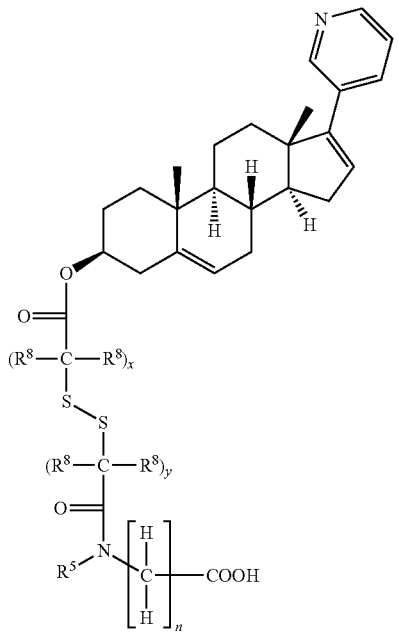

wherein x is 1, 2, 3, 4, 5, 6, 7, or 8; and y is 1, 2, 3, 4, 5, 6, 7, or 8.

In some embodiments, the compound of Formula (I) and/or Formula (III) has the structure:

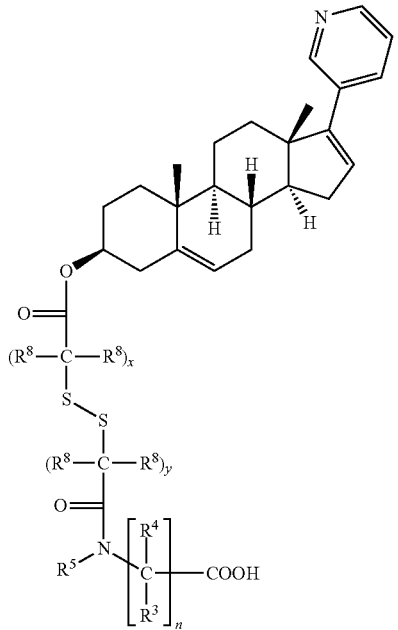

wherein x is 1, 2, 3, 4, 5, 6, 7, or 8; and y is 1, 2, 3, 4, 5, 6, 7, or 8.

In some embodiments, x is 1, 2, 3, 4, or 5. In some embodiments, x is 1, 2, or 3. In some embodiments, x is 2.

In some embodiments, y is 1, 2, 3, 4, or 5. In some embodiments, y is 1, 2, or 3. In some embodiments, y is 2.

In some embodiments, n is 1 or 2. For example, n can be 1.

In some embodiments, x is 1, 2, or 3; y is 1, 2, or 3; and n is 1 or 2.

In some embodiments, the compound of Formula (I) and/or Formula (III), or pharmaceutically acceptable salt thereof, has a structure selected from:

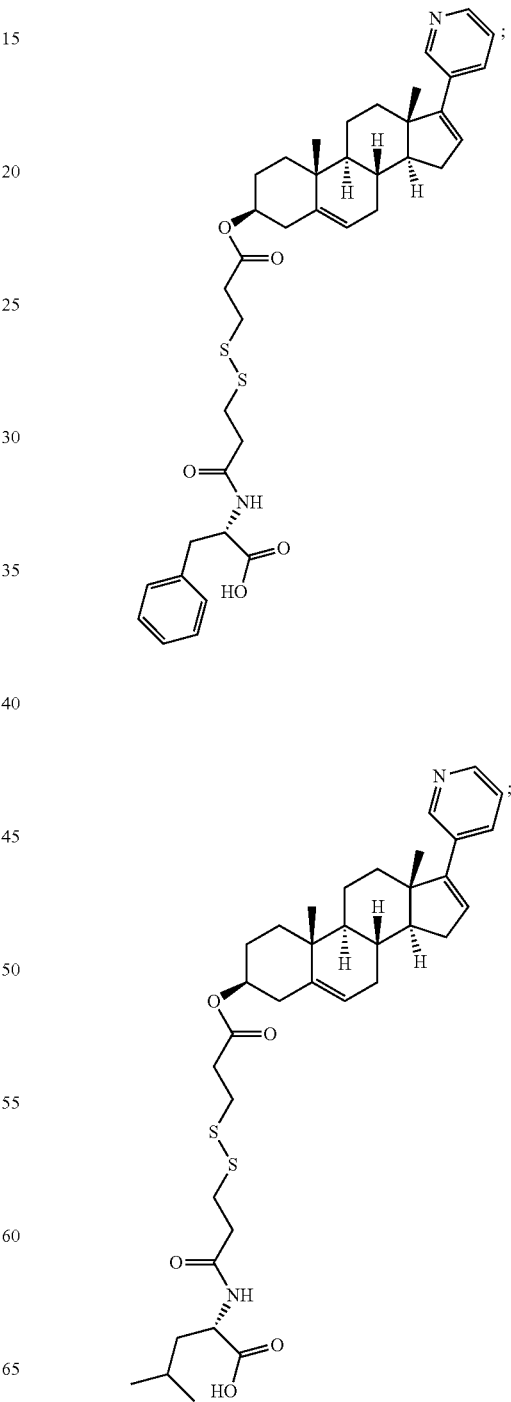

37
-continued
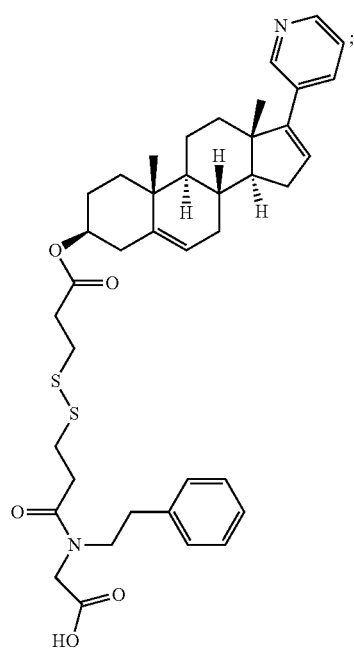
38
-continued
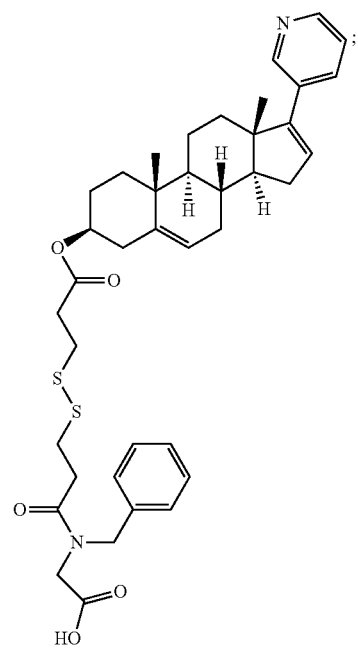
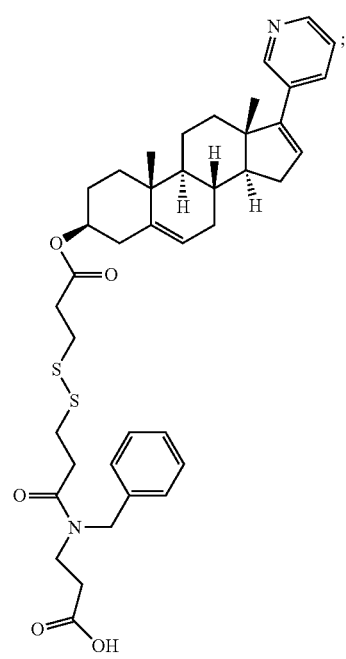
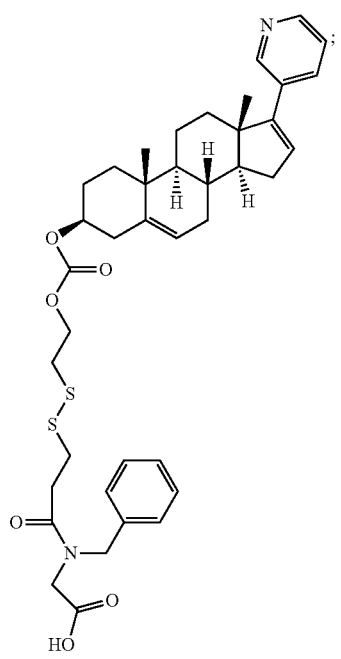

39
-continued
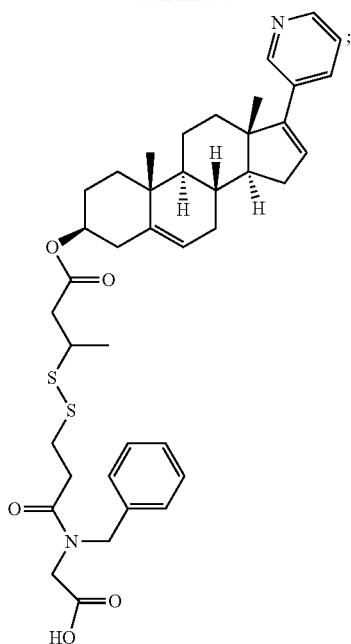
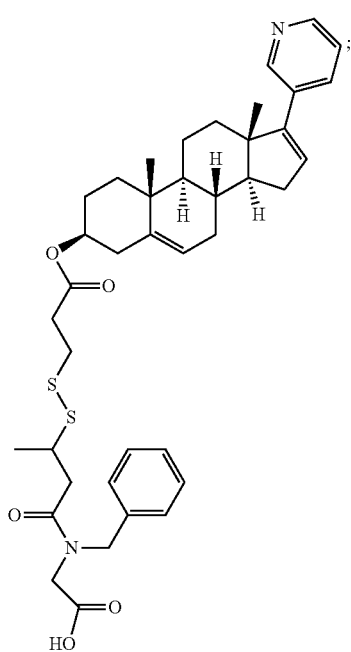
40
-continued
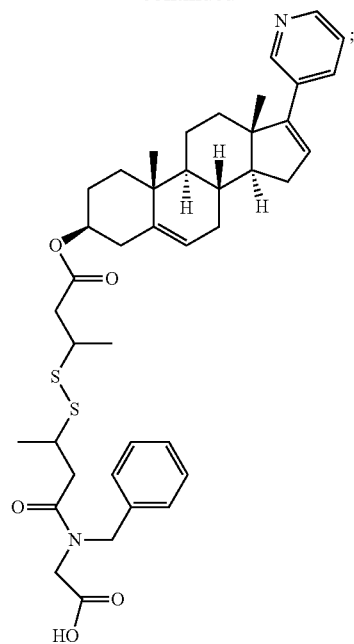
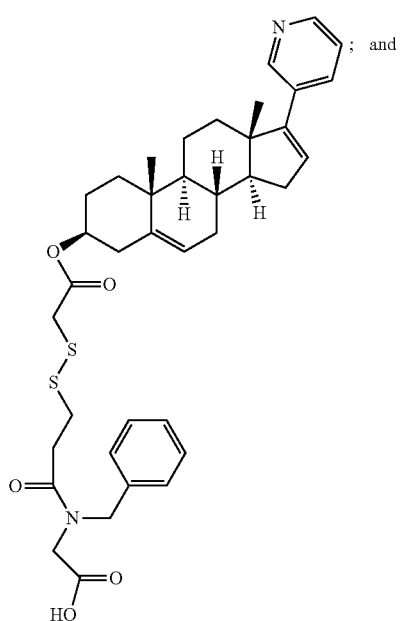; and 41
-continued
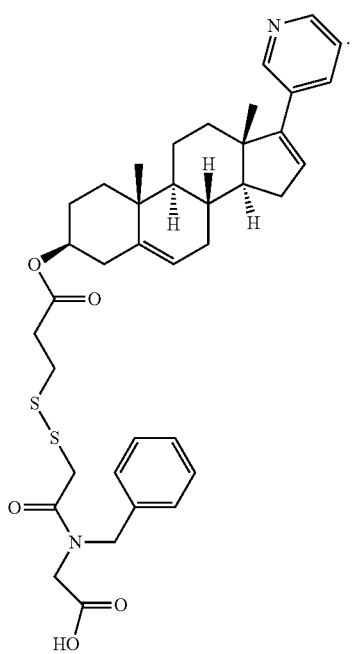
42
-continued
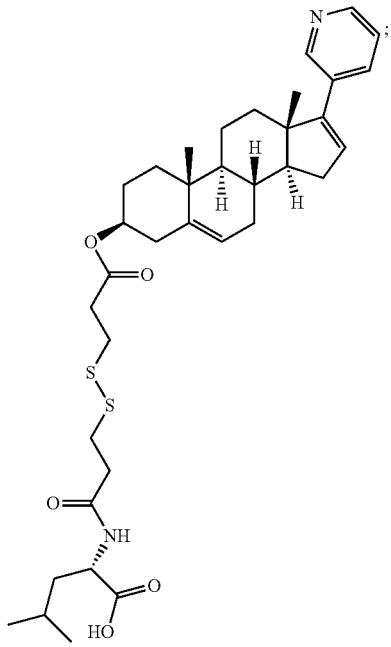
In some embodiments, the compound of Formula (I) and/or Formula (III), or pharmaceutically acceptable salt thereof, has a structure selected from:

43
-continued
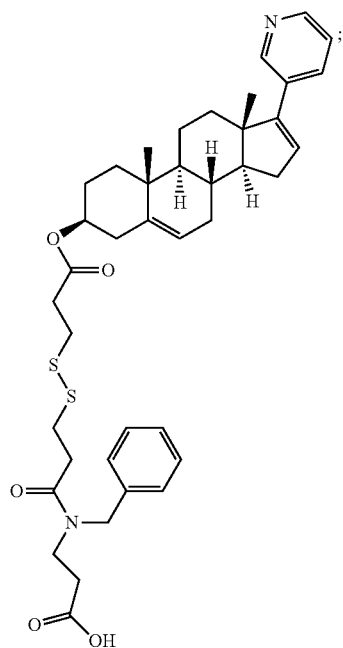
44
-continued
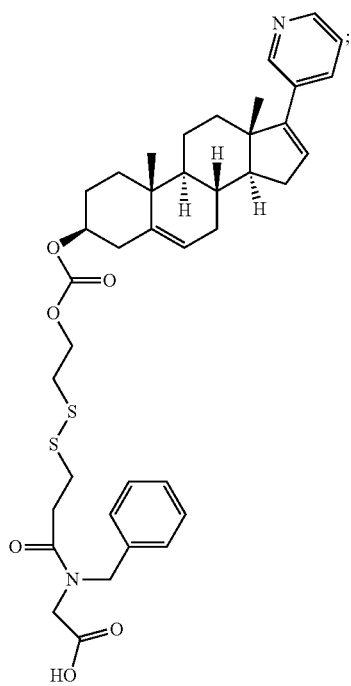

45
-continued
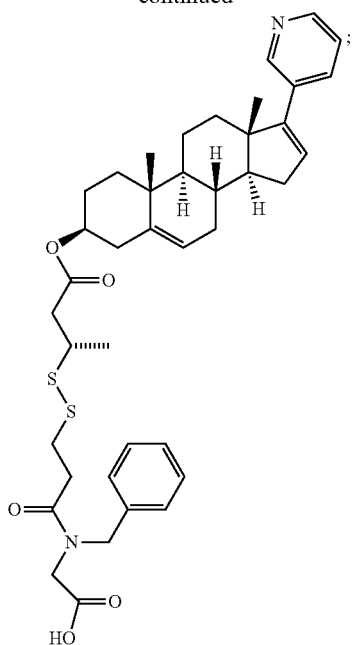
46
-continued
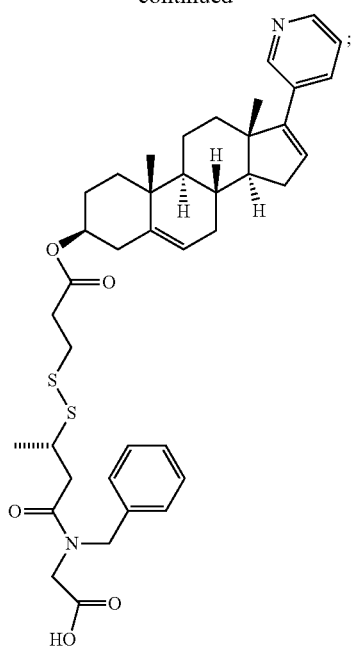
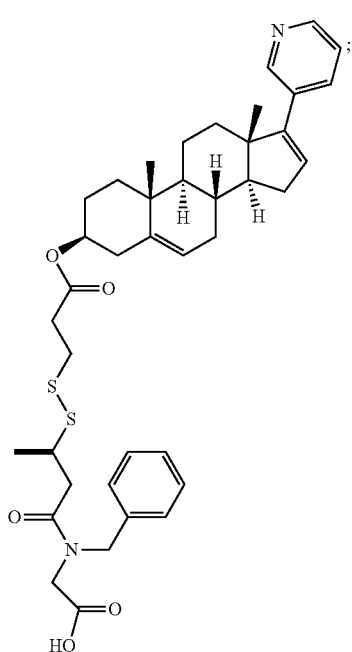
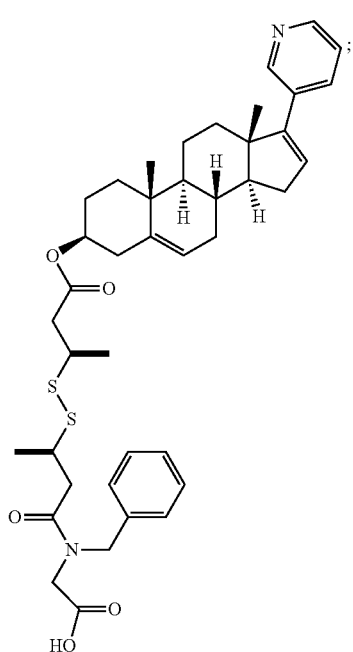

47
-continued
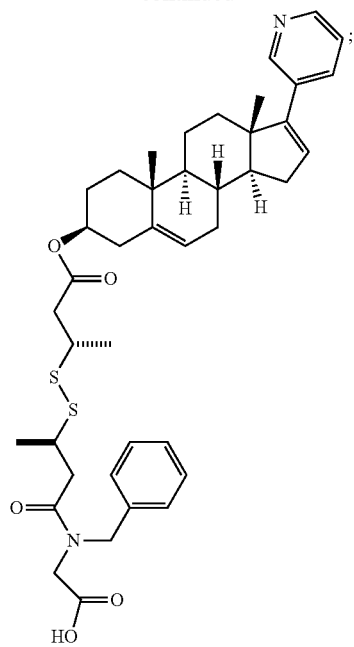
48
-continued
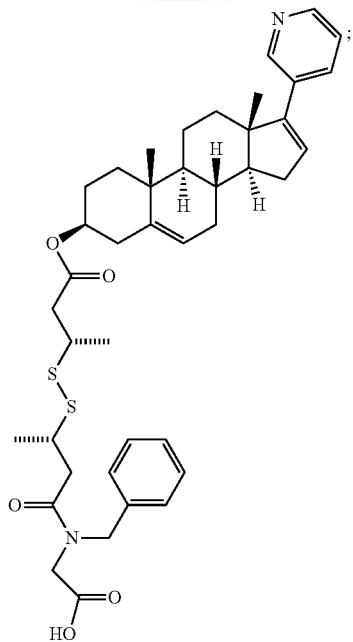
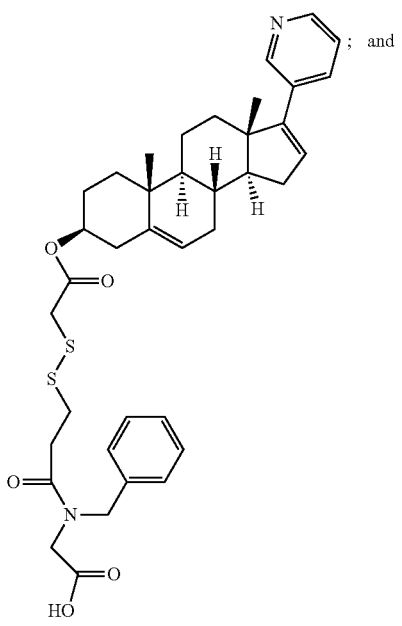

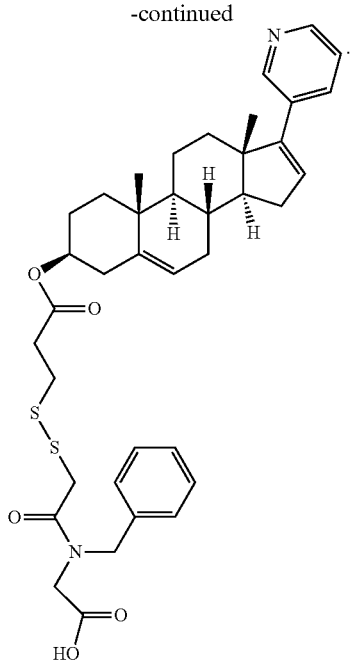

Non-Covalent Complexes

An aspect of the present disclosure is directed toward non-covalently bound complexes of a compound as described herein, or a pharmaceutically acceptable salt thereof, and serum albumin. In some embodiments, a non-covalently bound complex can dissociate upon administration to reveal an abiraterone derivative as described herein, which in turn can be cleaved by in vivo enzymes to produce the pharmaceutically active substance abiraterone. In some embodiments, the compound has a structure according to Formula (I) as described anywhere herein. In some embodiments, the compound has a structure according to Formula (II) as described anywhere herein. In some embodiments, the compound has a structure according to Formula (III) as described anywhere herein.

In some embodiments, the serum albumin is human serum albumin (HSA).

In some embodiments, the non-covalently bound complex of a compound as described herein and serum albumin has a molar ratio of compound to serum albumin of from about 1:1 to about 10:1. In some embodiments, the molar ratio has a range of from about 1:1 to about 4:1, from about 2:1 to about 4:1, from about 3:1 to about 4:1, about 1:1 to about 5:1, from about 2:1 to about 5:1, from about 3:1 to about 5:1, from about 4:1 to about 5:1, from about 1:1 to about 6:1, from about 2:1 to about 6:1, from about 3:1 to about 6:1, from about 4:1 to about 6:1, from about 5:1 to about 6:1, from about 1:1 to about 7:1, from about 2:1 to about 7:1, from about 3:1 to about 7:1, from about 4:1 to about 7:1, from about 5:1 to about 7:1, from about 6:1 to about 7:1, from about 1:1 to about 8:1, from about 2:1 to about 8:1, from about 3:1 to about 8:1, from about 4:1 to about 8:1, from about 5:1 to about 8:1, from about 6:1 to about 8:1, from about 7:1 to about 8:1, from about 1:1 to about 9:1, from about 2:1 to about 9:1, from about 3:1 to about 9:1, from about 4:1 to about 9:1, from about 5:1 to about 9:1, from about 6:1 to about 9:1, from about 7:1 to about 9:1, from about 8:1 to about 9:1, from about 2:1 to about 10:1, from about 3:1 to about 10:1, from about 4:1 to about 10:1, from about 5:1 to about 10:1, from about 6:1 to about 10:1, from about 7:1 to about 10:1, from about 8:1 to about 10:1, or from about 9:1 to about 10:1. In some embodiments, the molar ratio is greater than about 2:1, 3:1, 4:1, 5:1, 6:1, 7:1, 8:1, or 9:1.

In some embodiments, the non-covalently bound complex of a compound as described herein and serum albumin has a molar ratio of compound to serum albumin of from about 2:1 to about 7:1.

In some embodiments, the non-covalently bound complex of a compound as described herein and serum albumin has a molar ratio of compound to serum albumin of from about 3:1 to about 7:1.

In some embodiments, the non-covalently bound complex of a compound as described herein and serum albumin has a molar ratio of compound to serum albumin of from about 4:1 to about 6:1.

In some embodiments, the non-covalently bound complex of a compound described herein and serum albumin is in a solid formulation. The solid formulation typically has been produced in a uniform manner by lyophilization. A skilled artisan would recognize other methods, such as rotary evaporation, that can also produce solid formulations.

In some embodiments, the non-covalently bound complex of a compound described herein and serum albumin is in an aqueous formulation. In some embodiments, the non-covalently bound complex of the compound and serum albumin is in an aqueous formulation substantially free of solvents other than water. In some embodiments, the non-covalently bound complex of the compound and serum albumin is in an aqueous solution that contains less than about 0.5%, 0.3%, 0.2%, 0.1%, 0.075%, 0.05%, 0.03%, 0.02%, 0.01%, 0.0075%, 0.005%, 0.003%, 0.002%, or 0.001% by weight, of any non-water solvent. In some embodiments, the non-covalently bound complex of the compound and serum albumin is in an aqueous formulation free of solvents other than water.

The non-covalently bound complex of a compound described herein and serum albumin has greatly enhanced solubility compared with abiraterone. The non-covalently bound complex can have solubility in aqueous solution of about 5, 8, 10, 12, 14, 16, 18, 20, 22, 24, 26, 28, 30, 32, 34, 36, 38, 40, 42, 44, 46, 48, or greater than about 50 mg/mL. In some embodiments, the non-covalently bound complex has solubility in aqueous solution of at least 5 mg/mL. In some embodiments, the non-covalently bound complex has solubility in aqueous solution of at least 10 mg/mL. In some embodiments, the non-covalently bound complex has solubility in aqueous solution of at least 20 mg/mL. In some embodiments, the non-covalently bound complex has solubility in aqueous solution of at least 30 mg/mL. In some embodiments, the non-covalently bound complex has solubility in aqueous solution of greater than about 50 mg/mL.

In some embodiments, the non-covalently bound complex is a non-covalently bound complex of an abiraterone derivative and human serum albumin in a molar ratio from about 1:1 to about 10:1, wherein the non-covalently bound complex has a solubility in aqueous solution of at least 5 mg/mL, and the abiraterone derivative includes a compound of Formula (I), Formula (II), and/or Formula (III). In some embodiments, the non-covalently bound complex is a non-covalently bound complex of an abiraterone derivative and human serum albumin in a molar ratio from about 1:1 to about 10:1, wherein the non-covalently bound complex has a solubility in aqueous solution of at least 5 mg/mL, and the abiraterone derivative consists essentially of a compound of Formula (I), Formula (II), and/or Formula (III). In some embodiments, the non-covalently bound complex is a non-covalently bound complex of an abiraterone derivative and human serum albumin in a molar ratio from about 1:1 to about 10:1, wherein the non-covalently bound complex has a solubility in aqueous solution of at least 5 mg/mL, and the abiraterone derivative consists of a compound of Formula (I), Formula (II), and/or Formula (III), or a pharmaceutically acceptable salt thereof.

General Method for Preparing a Non-Covalently Bound Complex of the Abiraterone Derivative with HSA Step 1: The abiraterone derivative is dissolved in a polar organic solvent, such as an alcohol, THF, $CH_3CN$, etc., or mixtures thereof.

In some embodiments, the polar organic solvent is an alcohol. In some embodiments, the polar organic solvent is ethanol or methanol, or mixtures thereof. For example, the polar organic solvent can be methanol. In some embodiments, the polar organic solvent is ethanol.

In some embodiments, the amount of polar organic solvent is from about 0.005 mL to about 10 mL per mg abiraterone derivative. In some embodiments, the amount of polar organic solvent is from about 0.05 mL to about 5 mL per mg abiraterone derivative. In some embodiments, the amount of polar organic solvent is from about 0.1 mL to about 2.0 mL per mg abiraterone derivative. In some embodiments, the amount of polar organic solvent is about 0.1 mL per mg abiraterone derivative. In some embodiments, the amount of polar organic solvent is about 0.2 mL per mg abiraterone derivative. In some embodiments, the amount of polar organic solvent is about 0.3 mL per mg abiraterone derivative. In some embodiments, the amount of polar organic solvent is about 0.4 mL per mg abiraterone derivative. In some embodiments, the amount of polar organic solvent is about 0.5 mL per mg abiraterone derivative.

Step 2: An amount of water is added to the solution.

In some embodiments, the amount of water is from about 0.010 mL to about 30 mL per mg abiraterone derivative. In some embodiments, the amount of water is from about 0.10 mL to about 15 mL per mg abiraterone derivative. In some embodiments, the amount of water is from about 0.2 mL to about 6 mL per mg abiraterone derivative. In some embodiments, the amount of water is from about 0.3 mL to about 2.0 mL per mg abiraterone derivative. In some embodiments, the amount of water is about 0.3 mL per mg abiraterone derivative. In some embodiments, the amount of water is about 0.4 mL per mg abiraterone derivative. In some embodiments, the amount of water is about 0.5 mL per mg abiraterone derivative. In some embodiments, the amount of water is about 1.0 mL per mg abiraterone derivative. In some embodiments, the amount of water is about 1.5 mL per mg abiraterone derivative.

In some embodiments, the water has pH of from about 1 to about 7. In some embodiments, the water has pH of from about 2 to about 7. In some embodiments, the water has pH of from about 3 to about 7. In some embodiments, the water has pH from about 4 to about 6.

In some embodiments, the water has pH of about 5.

In some embodiments, the water having pH of from about 1 to about 7 is prepared by adding an acid into water. In some embodiments, the water having pH of from about 1 to about 7 is prepared by adding hydrochloric acid into water. In some embodiments, the water having pH of from about 1 to about 7 is prepared by adding 2 N aqueous hydrochloric acid [HCl (aq)] into water. In some embodiments, the water having pH of from about 1 to about 7 is prepared by adding a 1 N HCl (aq) into water.

Step 3: A defined amount of serum albumin is then added to the solution.

In some embodiments, the serum albumin is human serum albumin. The resulting non-covalently bound complex can have any molar ratio of the abiraterone derivative to serum albumin as defined herein.

In some embodiments, the serum albumin is added to the water solution in step 2 first, and then the water solution of the serum albumin is added to the polar organic solution from step 1.

Step 4: The mixture is agitated at a temperature and time until reaction is deemed complete.

In some embodiments, the mixture is stirred. In some embodiments, the mixture is shaken.

In some embodiments, the temperature is from about 0° C. to about 40° C. In some embodiments, the temperature is at about room temperature. In some embodiments, the temperature is at about 25° C.

In some embodiments, the time is from about 0.1 min to about 24 hours. In some embodiments, the time is from about 0.5 min to about 1 hour. In some embodiments, the time is from about 1 min to about 10 min.

Step 5: The polar organic solvent is removed.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a clear solution.

Step 6: The water from the mixture is removed to provide a solid.

In some embodiments, the water is removed under a vacuum. In some embodiments, the water is removed using rotary evaporation. In some embodiments, the water is removed by lyophilization.

Step 7: Optionally, the solid is reconstituted by adding water.

In some embodiments, the addition of water for reconstitution yields a clear solution.

Pharmaceutical Compositions and Administration

The methods provided herein include the manufacture and use of pharmaceutical compositions, which include one or more of the compounds provided herein. Also included are the pharmaceutical compositions themselves.

Pharmaceutical compositions typically include a pharmaceutically acceptable carrier. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In some embodiments, the composition is sterile and is fluid to the extent that easy syringability exists. Proper fluidity can be maintained, for example, by the use of coating materials, such as lecithin, by the maintenance of the required particle size in the case of dispersions, and by the use of surfactants.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation is freeze-drying (lyophilization), which yields a powder of the active ingredient plus any additional desired ingredient from a previously sterile-filtered solution thereof.

Methods of Use

The endoplasmic reticular cytochrome P450, 17α hydroxylase, 17-20 lyase in humans (CYP17) plays a key role in the biosynthesis of steroid hormones (Akhtar, M. K. et al. *Journal of Endocrinology* 2005, 187, 267-274). Accordingly, its dysfunction has been correlated with a number of diseases, including polycystic ovary syndrome, Cushing's syndrome, congenital adrenal hyperplasia, and prostate cancer.

An aspect of the current application is directed to a compound provided herein, a non-covalent complex of serum albumin with the compound, or a pharmaceutical composition including the same, that can be administered to treat a disease or condition that would benefit from inhibition of CYP17.

Also provided in the present disclosure is a method of treating a disease associated with the activity of CYP17, the method including administering to a mammalian patient a pharmaceutical composition as described herein. In some embodiments, the disease is cancer. In some embodiments, the cancer is breast cancer, ovarian cancer, or prostate cancer.

Also provided in the present disclosure is a compound as described herein, a non-covalent complex of serum albumin with the compound, or a pharmaceutical composition including the same, which can be administered to treat cancer in a patient. Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. In some embodiments, the cancer is selected from a breast cancer, a colon cancer, a leukemia, a bone cancer, a lung cancer, a bladder cancer, a brain cancer, a bronchial cancer, a cervical cancer, a colorectal cancer, an endometrial cancer, an ependymoma cancer, a retinoblastoma cancer, a gallbladder cancer, a gastric cancer, a gastrointestinal cancer, a glioma cancer, a head and neck cancer, a heart cancer, a liver cancer, a pancreatic cancer, a melanoma cancer, a kidney cancer, a laryngeal cancer, a lip or oral cancer, a lymphoma cancer, a mesothioma cancer, a mouth cancer, a myeloma cancer, a nasopharyngeal cancer, a neuroblastoma cancer, an oropharyngeal cancer, an ovarian cancer, a thyroid cancer, a penile cancer, a pituitary cancer, a prostate cancer, a rectal cancer, a renal cancer, a salivary gland cancer, a sarcoma cancer, a skin cancer, a stomach cancer, a testicular cancer, a throat cancer, a uterine cancer, a vaginal cancer, and a vulvar cancer.

In some embodiments, the cancer is breast cancer.

In some embodiments, the cancer is prostate cancer. In some embodiments, prostate cancer is selected from hormone refractory prostate cancer; prostate cancer with a rising PSA (prostate-specific antigen); prostate cancer with a rising PSA and nodal disease following definitive radical prostatectomy; progressive chemotherapy-naïve castration-resistant prostate cancer; prostate cancer in patients who have failed hormone therapy; prostate cancer in patients who have failed androgen deprivation and docetaxel-based chemotherapy; metastatic hormone-resistant prostate cancer; high-risk, metastatic hormone-naïve prostate cancer; and metastatic castration-resistant prostate cancer. For example, prostate cancer can include metastatic castration-resistant prostate cancer. In some embodiments, the prostate cancer is responsive to androgen-deprivation therapy.

EXAMPLES

Syntheses of abiraterone and related compounds have been reported by others. For example, U.S. Pat. Nos. 8,338, 588; 8,076,474; and 5,604,213 describe methods for the synthesis of abiraterone and are hereby incorporated by reference in its entirety.

Synthesis:

A compound of Formula (I) is an ester, a carbonate, or a carbamate analog, when A is a covalent bond, O or NR$^1$ respectively. The methods to prepare an ester, a carbonate, or a carbamate analog are well documented in the field of organic chemistry. It is well within the ability of a skilled organic chemist to prepare these compounds.

The following Schemes 1-4 are general synthetic methods for making compounds of Formula (II) from abiraterone. For conciseness, the Schemes are depicted for compounds of Formula (II), wherein A is a covalent bond. It is well within the ability of a skilled artisan to adapt these Schemes for synthesis of compounds of Formula (II) wherein A is O or NR$^1$.

Scheme 1

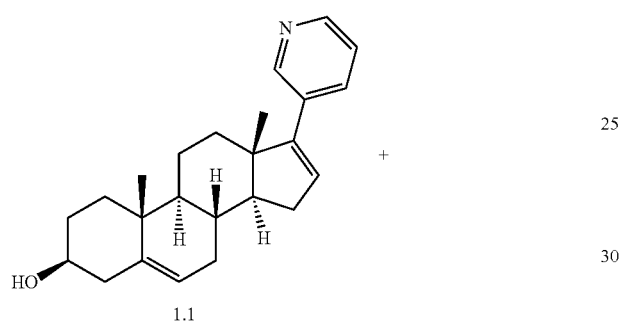

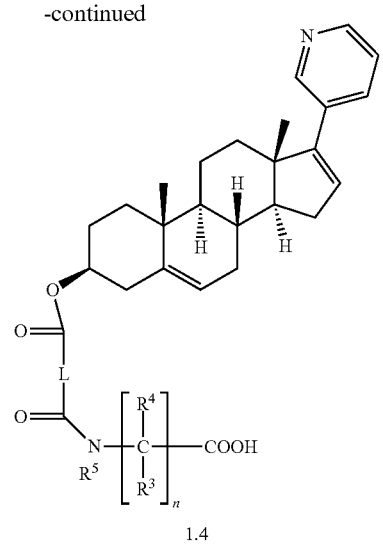

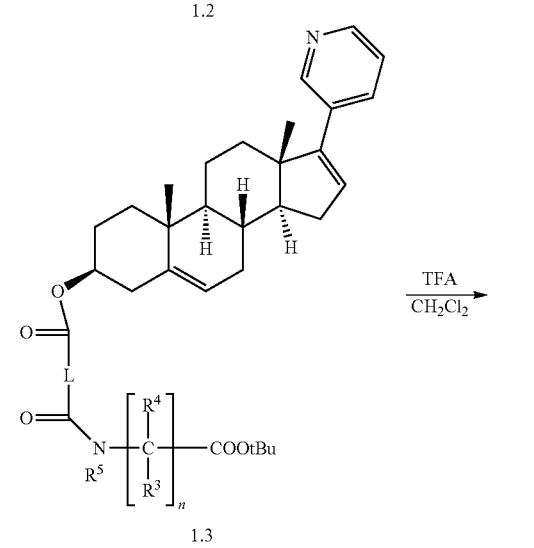

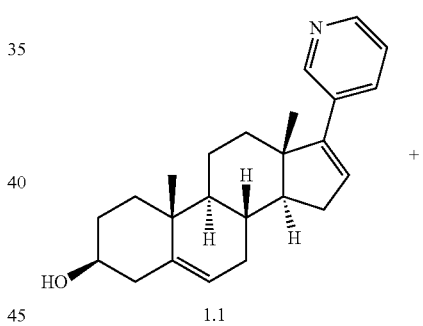

Scheme 2

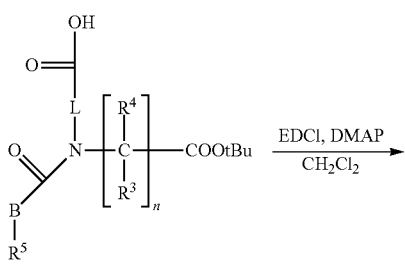

-continued
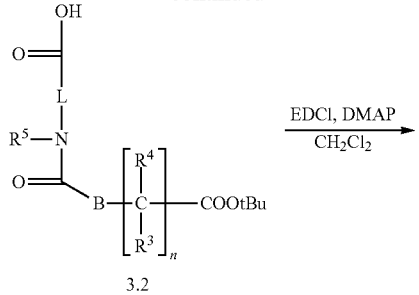
3.2
TFA / CH₂Cl₂ →
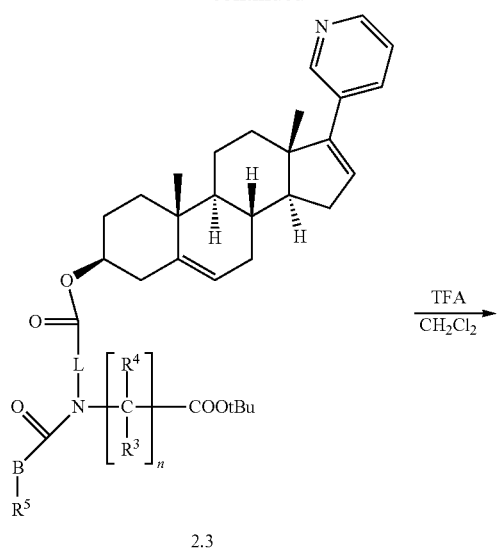
2.3
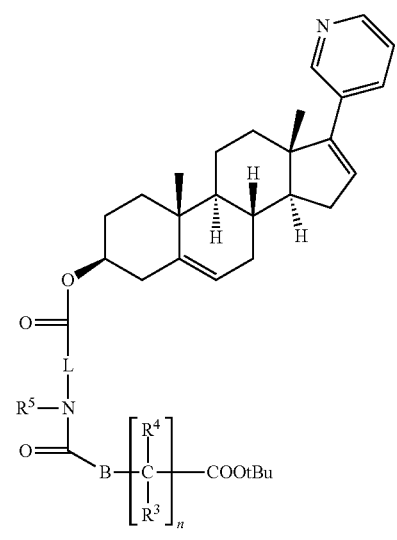
3.3
TFA/CH₂Cl₂ →
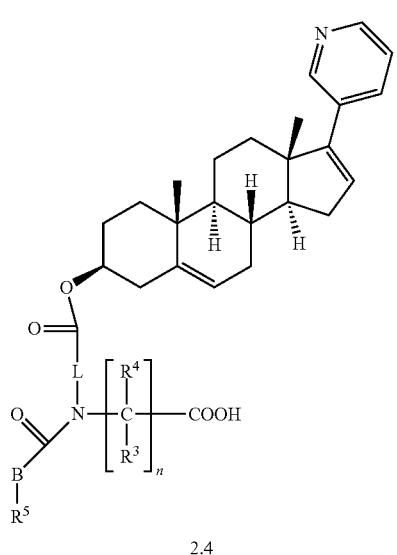
2.4
Scheme 3
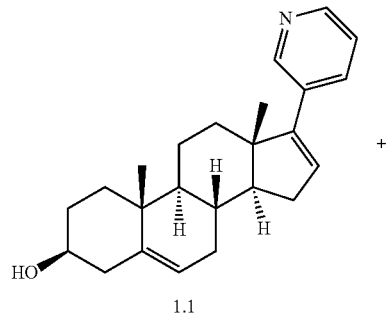
1.1
+
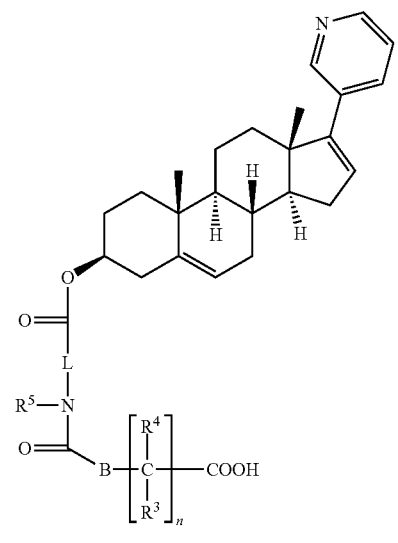
3.4

Scheme 4
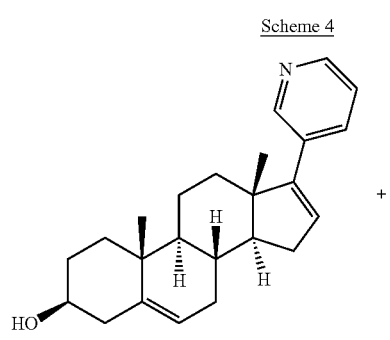
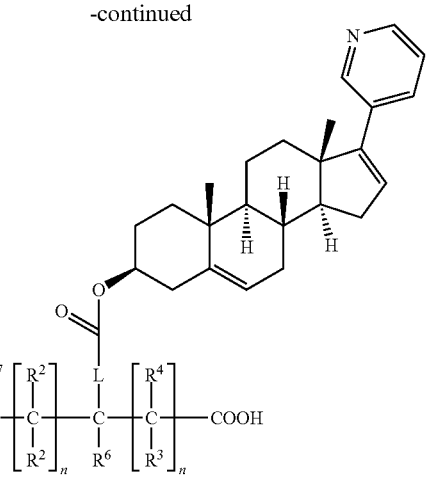
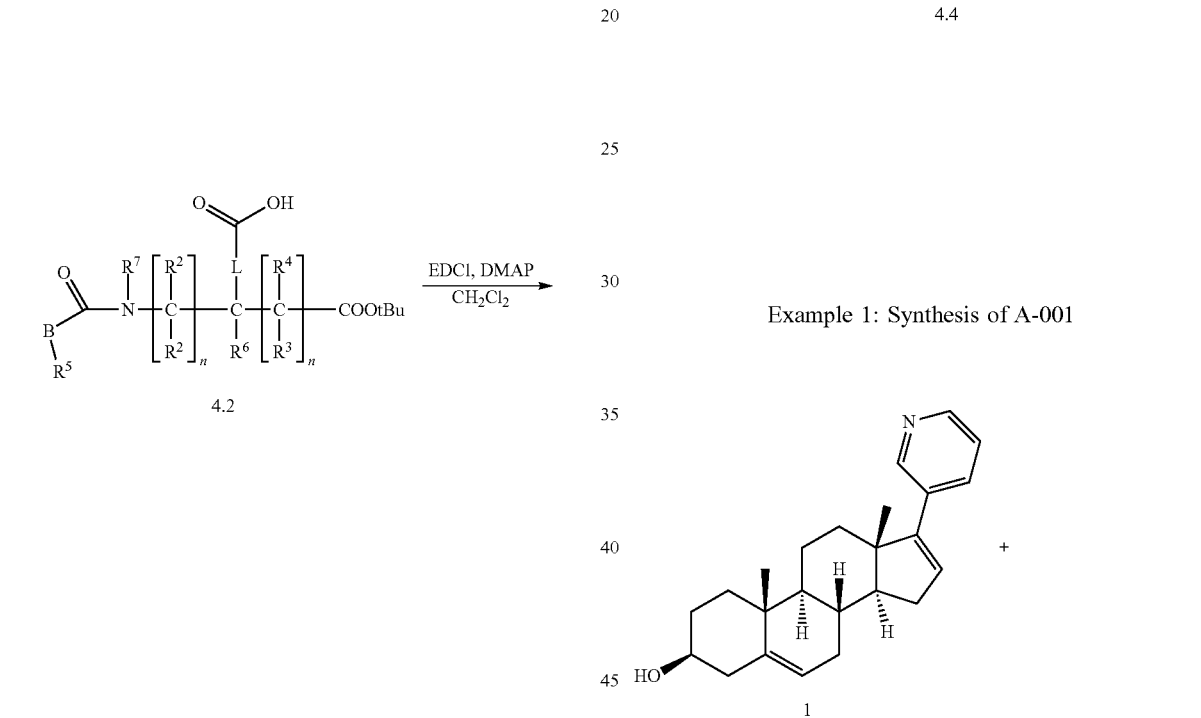
Example 1: Synthesis of A-001
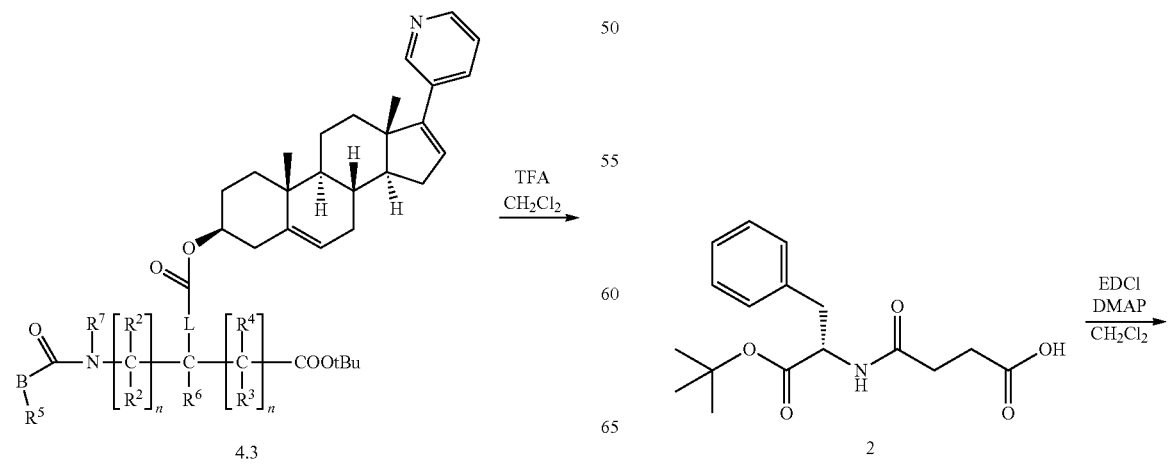

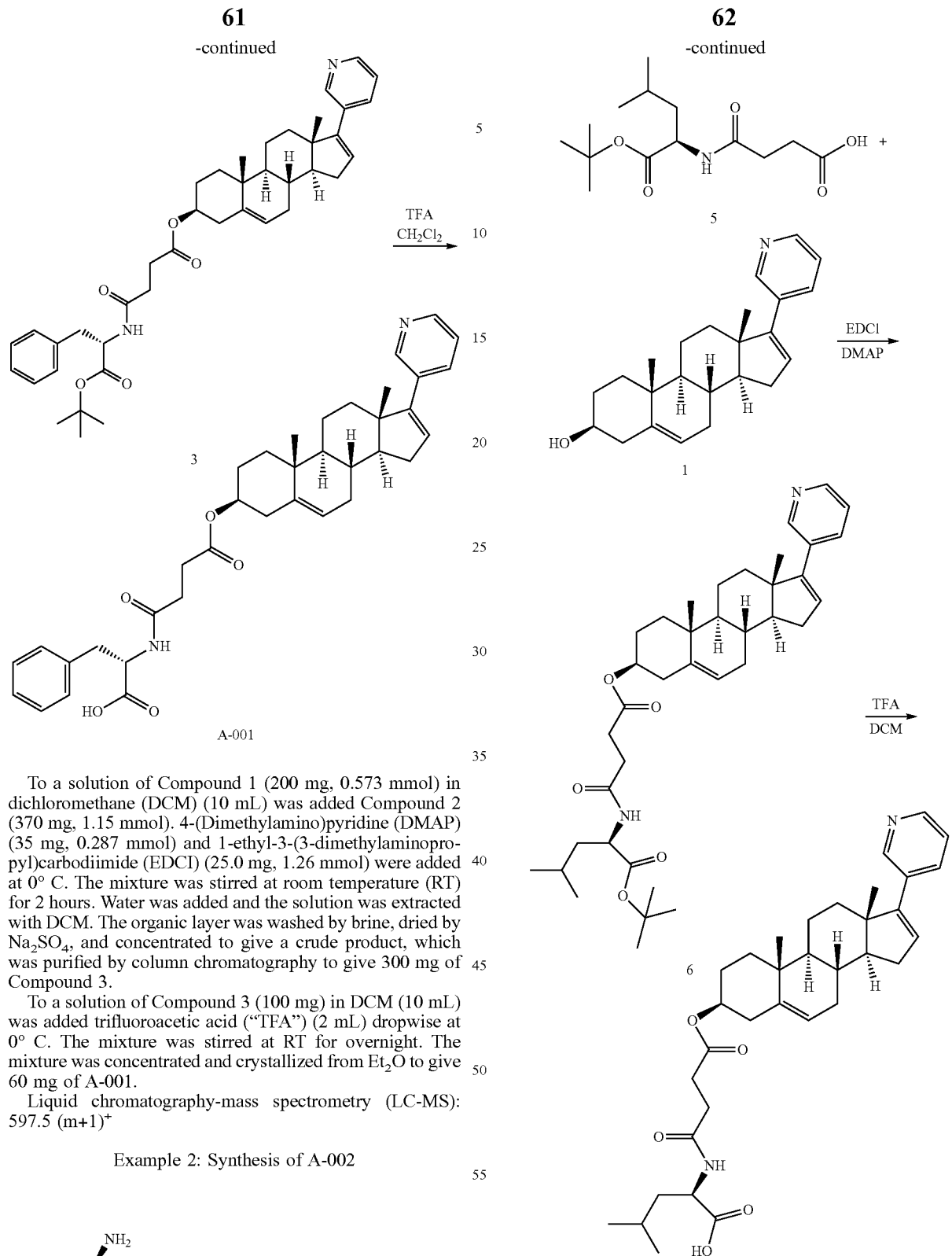

To a solution of Compound 1 (200 mg, 0.573 mmol) in dichloromethane (DCM) (10 mL) was added Compound 2 (370 mg, 1.15 mmol). 4-(Dimethylamino)pyridine (DMAP) (35 mg, 0.287 mmol) and 1-ethyl-3-(3-dimethylaminopropyl)carbodiimide (EDCI) (25.0 mg, 1.26 mmol) were added at 0° C. The mixture was stirred at room temperature (RT) for 2 hours. Water was added and the solution was extracted with DCM. The organic layer was washed by brine, dried by $Na_2SO_4$, and concentrated to give a crude product, which was purified by column chromatography to give 300 mg of Compound 3.

To a solution of Compound 3 (100 mg) in DCM (10 mL) was added trifluoroacetic acid ("TFA") (2 mL) dropwise at 0° C. The mixture was stirred at RT for overnight. The mixture was concentrated and crystallized from $Et_2O$ to give 60 mg of A-001.

Liquid chromatography-mass spectrometry (LC-MS): 597.5 $(m+1)^+$

Example 2: Synthesis of A-002

To a solution of Compound 4 (2 g, 10.7 mmol) in pyridine (20 mL) was added dihydrofuran-2,5-dione (1.4 g, 14 mmol), and the mixture was stirred at RT overnight. The mixture was concentrated, then treated with water and extracted with ethyl acetate ("EA"). The organic layer was washed with brine, dried over anhydrous $Na_2SO_4$, filtered, and concentrated. The crude product was purified by recrystallization to give Compound 5 (2 g, 66.7%).

To a solution of Compound 1 (200 mg, 0.573 mmol) in DCM (10 mL) was added Compound 5 (330 mg, 1.15 mmol). Then DMAP (35 mg, 0.287 mmol) and EDO (250 mg, 1.26 mmol) were added at 0° C. The mixture was stirred at RT overnight. The residue was treated with water and extracted with DCM. The organic layer was washed with brine, dried over anhydrous Na$_2$SO$_4$, filtered and concentrated to give 350 mg crude product. Then it was purified by column to afford Compound 6 (100 mg, 28.2%).

To a solution of Compound 6 (100 mg, 0.16 mmol) in DCM (10 mL) was added TFA (5 mL) dropwise at 0° C. The mixture was stirred at RT for overnight. The mixture was concentrated and purified by column to give A-002 (10 mg, 11%).

LC-MS: 563.5 (m+1)$^+$

Example 3: Synthesis of A-003

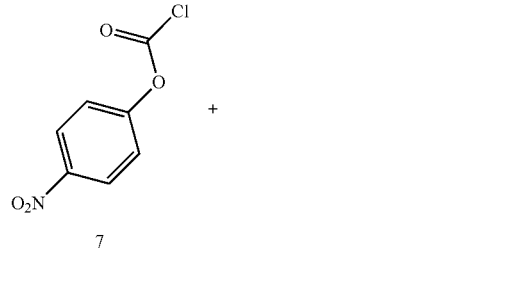

7

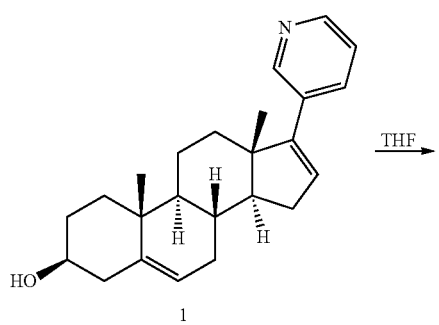

1

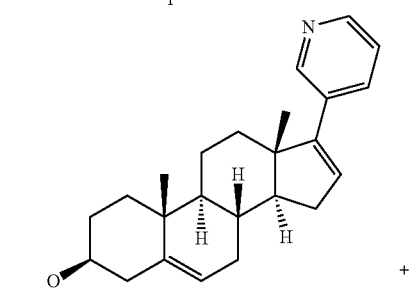

8

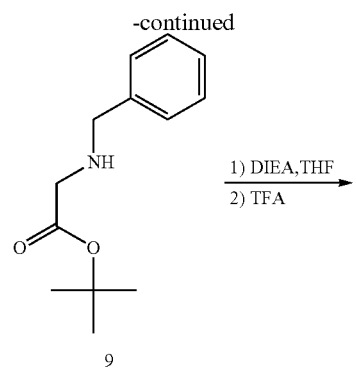

9

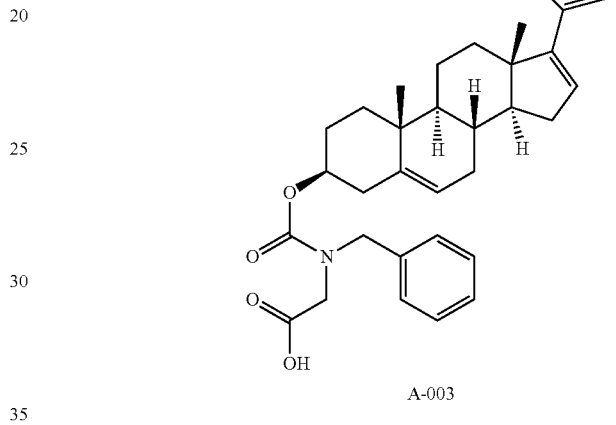

A-003

To a solution of Compound 1 (200 mg, 0.573 mmol) in tetrahydrofuran (THF) (5 mL) was added Compound 7 (150 mg, 0.744 mmol) dropwise at 0° C. The mixture was stirred at reflux for 3 hours. After cooling to RT, petroleum ether (PE) (10 mL) was added. The precipitate was filtered washed with PE and dried in vacuo to afford Compound 8 (200 mg, 69%).

To a solution of Compound 8 (200 mg, 0.39 mmol) in THF (2 mL) was added Compound 9 (344 mg, 1.56 mmol) and NN-diisopropylethylamine (DIEA) (550 uL, 3.11 mmol). The mixture was stirred at reflux for overnight. The mixture was concentrated and purified by column to give 40 mg the intermediate. A mixture of the intermediate (40 mg) in DCM/TFA (3 mL, 2:1) was stirred at RT overnight. The residue was concentrated and purified by column to afford A-003 (20 mg).

LC-MS: 541.5 (m+1)$^+$

Example 4: Synthesis of A-004

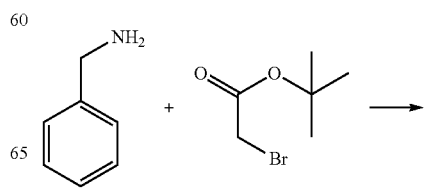

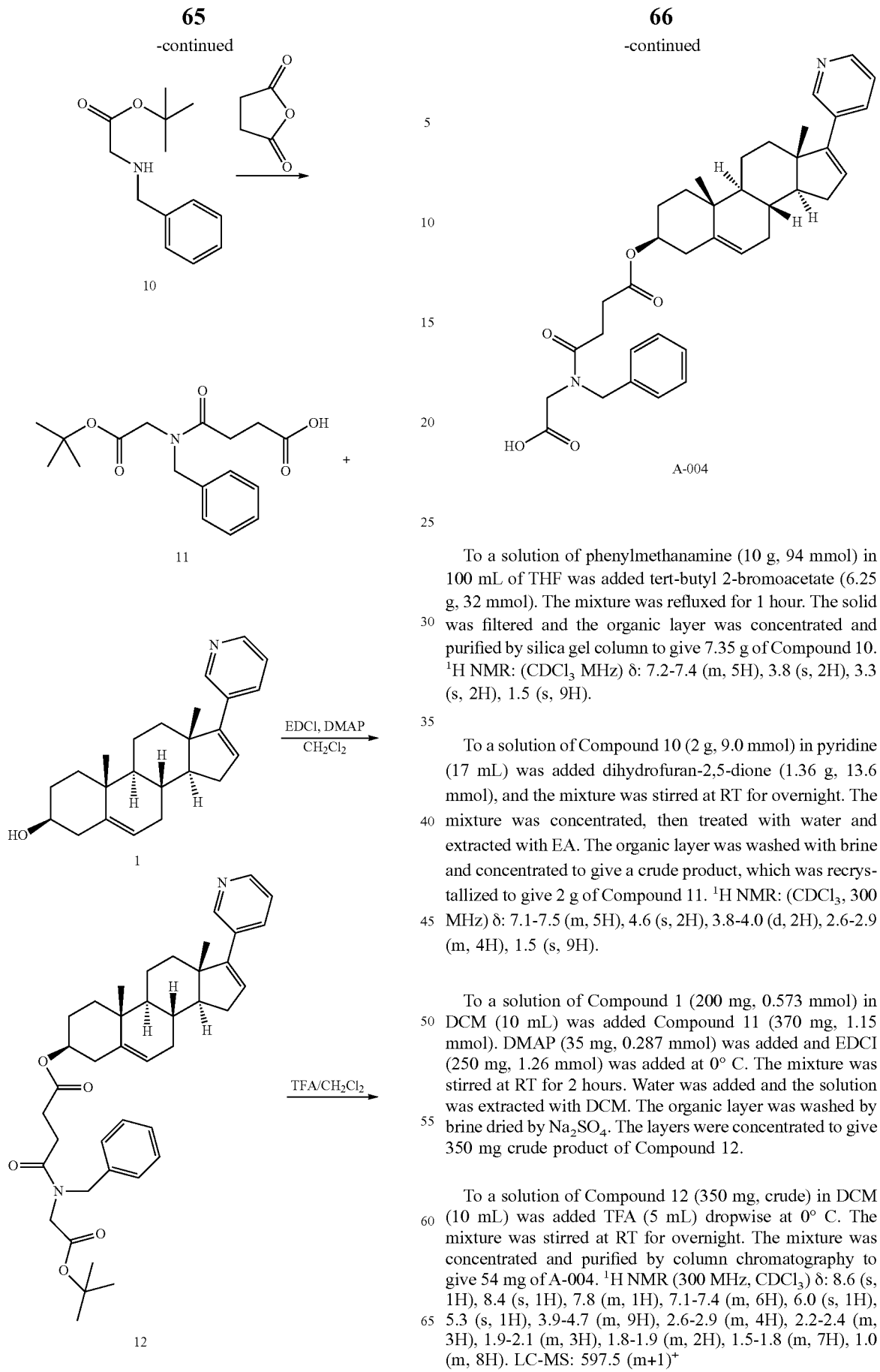

To a solution of phenylmethanamine (10 g, 94 mmol) in 100 mL of THF was added tert-butyl 2-bromoacetate (6.25 g, 32 mmol). The mixture was refluxed for 1 hour. The solid was filtered and the organic layer was concentrated and purified by silica gel column to give 7.35 g of Compound 10. $^1$H NMR: (CDCl$_3$ MHz) δ: 7.2-7.4 (m, 5H), 3.8 (s, 2H), 3.3 (s, 2H), 1.5 (s, 9H).

To a solution of Compound 10 (2 g, 9.0 mmol) in pyridine (17 mL) was added dihydrofuran-2,5-dione (1.36 g, 13.6 mmol), and the mixture was stirred at RT for overnight. The mixture was concentrated, then treated with water and extracted with EA. The organic layer was washed with brine and concentrated to give a crude product, which was recrystallized to give 2 g of Compound 11. $^1$H NMR: (CDCl$_3$, 300 MHz) δ: 7.1-7.5 (m, 5H), 4.6 (s, 2H), 3.8-4.0 (d, 2H), 2.6-2.9 (m, 4H), 1.5 (s, 9H).

To a solution of Compound 1 (200 mg, 0.573 mmol) in DCM (10 mL) was added Compound 11 (370 mg, 1.15 mmol). DMAP (35 mg, 0.287 mmol) was added and EDCI (250 mg, 1.26 mmol) was added at 0° C. The mixture was stirred at RT for 2 hours. Water was added and the solution was extracted with DCM. The organic layer was washed by brine dried by Na$_2$SO$_4$. The layers were concentrated to give 350 mg crude product of Compound 12.

To a solution of Compound 12 (350 mg, crude) in DCM (10 mL) was added TFA (5 mL) dropwise at 0° C. The mixture was stirred at RT for overnight. The mixture was concentrated and purified by column chromatography to give 54 mg of A-004. $^1$H NMR (300 MHz, CDCl$_3$) δ: 8.6 (s, 1H), 8.4 (s, 1H), 7.8 (m, 1H), 7.1-7.4 (m, 6H), 6.0 (s, 1H), 5.3 (s, 1H), 3.9-4.7 (m, 9H), 2.6-2.9 (m, 4H), 2.2-2.4 (m, 3H), 1.9-2.1 (m, 3H), 1.8-1.9 (m, 2H), 1.5-1.8 (m, 7H), 1.0 (m, 8H). LC-MS: 597.5 (m+1)$^+$

Example 5: Synthesis of A-005

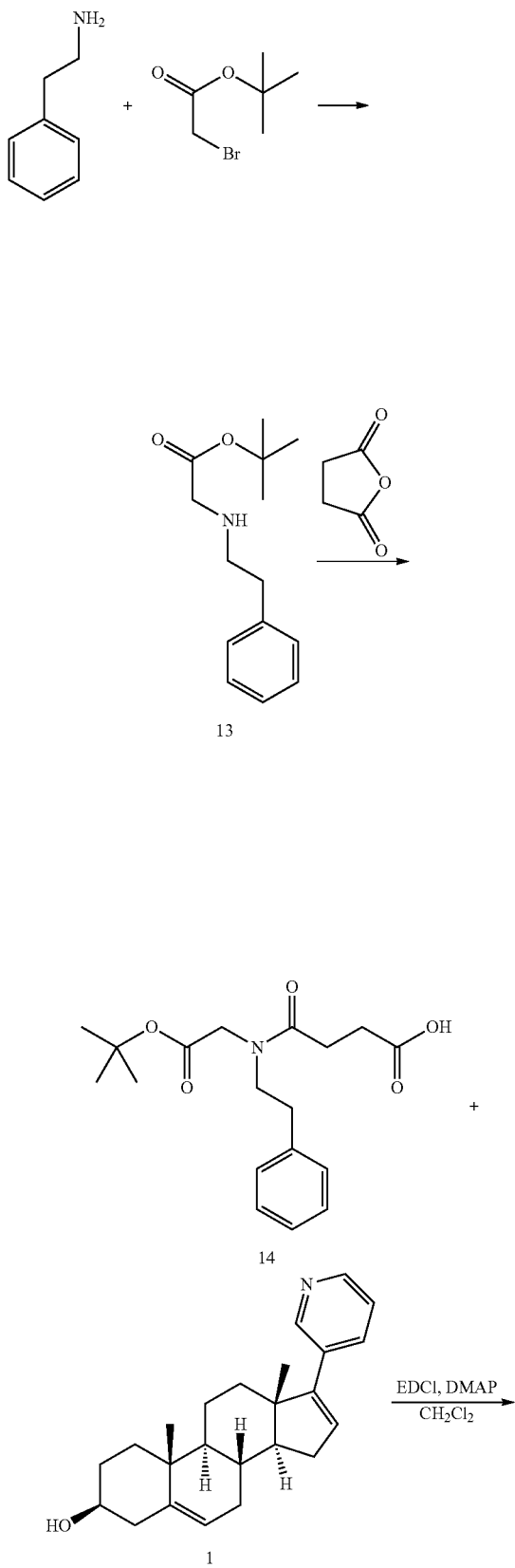

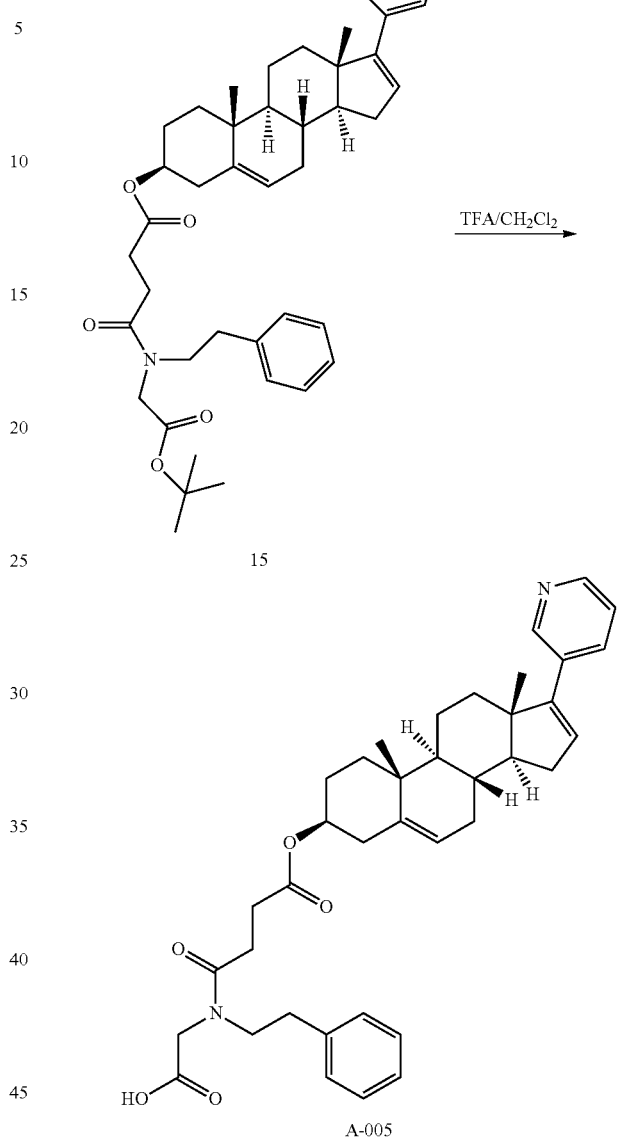

To a solution of phenylmethanamine (10 g, 82 mmol) in 100 mL THF was added tert-butyl 2-bromoacetate (6.25 g, 27 mmol). The mixture was refluxed for 1 hour. The solid was filtered and the organic layer was concentrated. The crude product was purified by silica gel column to give 5.4 g of Compound 13.

To a solution of Compound 13 (1 g, 4.2 mmol) in pyridine (9 mL) was added dihydrofuran-2,5-dione (1.28 g, 12.8 mmol), and the mixture was stirred at RT for overnight. The mixture was concentrated, then treated with water and extracted with EA. The organic layer was washed with brine and concentrated. The crude product was recrystallized to give 1.2 g of Compound 14.

To a solution of Compound 1 (200 mg, 0.573 mmol) in DCM (10 mL) was added Compound 14 (384 mg, 1.14 mmol). DMAP (35 mg, 0.287 mmol) was added and EDCI (391 mg, 2.0 mmol) was added at 0° C. The mixture was stirred at RT for 2 hours. Water was added and the solution was extracted with DCM. The organic layer was washed by brine dried by Na₂SO₄ and concentrated to give 350 mg crude product of Compound 15.

To a solution of Compound 15 (350 mg, crude) in DCM (10 mL) was added TFA (5 mL) dropwise at 0° C. The mixture was stirred at RT for overnight. The mixture was concentrated and purified by column chromatography to give 180 mg of A-005.

LC-MS: 611.6 (m+1)⁺

Example 6: Synthesis of A-006

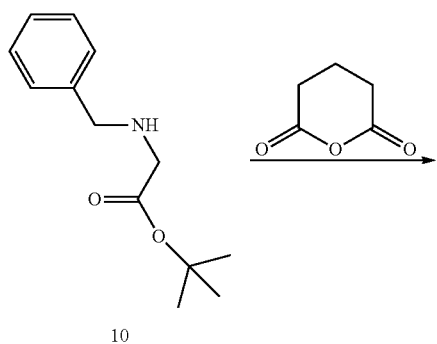

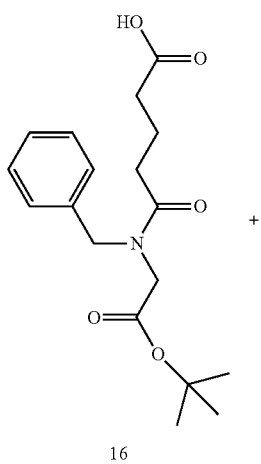

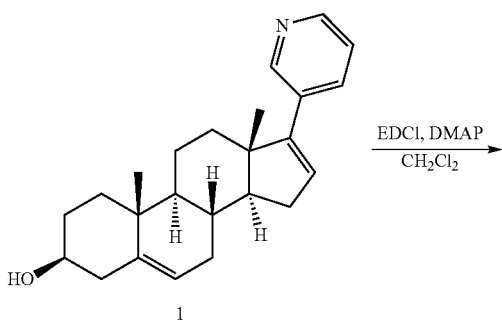

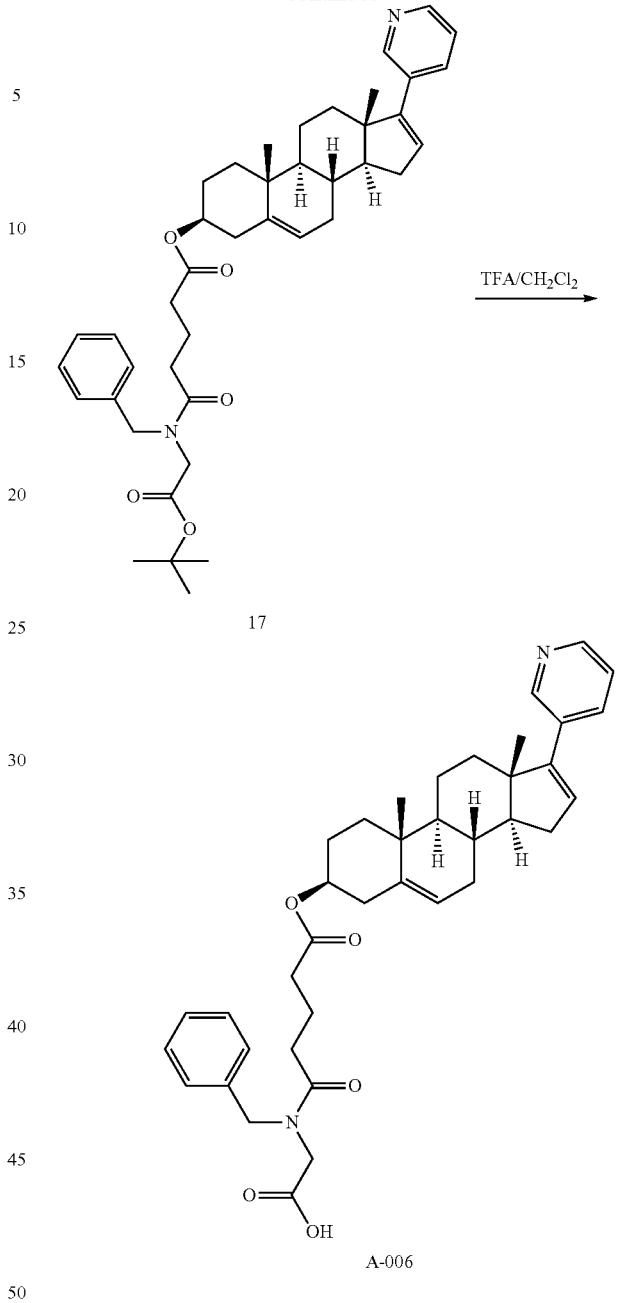

To a solution of Compound 10 (2 g, 9.0 mmol) in pyridine (17 mL) was added dihydro-2H-pyran-2,6(3H)-dione (1.54 g, 13.5 mmol), and the mixture was stirred at RT for overnight. The mixture was concentrated, then treated with water and extracted with EA. The organic layer was washed with brine and dried by Na₂SO₄ and concentrated to give a crude product, which was purified by silica gel column to give 2 g of Compound 16.

To a solution of compound 1 (200 mg, 0.573 mmol) in DCM (10 mL) was added Compound 16 (370 mg, 1.15 mmol). DMAP (35 mg, 0.287 mmol) and EDCI (250 mg, 1.26 mmol) were added at 0° C. The mixture was stirred at RT for overnight. Water was added and the solution was extracted with DCM. The organic layer was dried by Na₂SO₄ and concentrated to give a crude product, which was purified by silica gel column to give 150 mg of Compound 17.

To a solution of Compound 17 (150 mg, 0.225 mol) in DCM (10 mL) was added TFA (5 mL) drop-wise at 0° C. The mixture was stirred at RT for overnight. The mixture was concentrated and extracted with DCM. The organic layer was dried by Na$_2$SO$_4$ and concentrated to give a crude product, which was purified by silica gel column to give 80 mg of A-006.

LC-MS: 611.5 (m+1)$^+$

Example 7: Synthesis of A-007

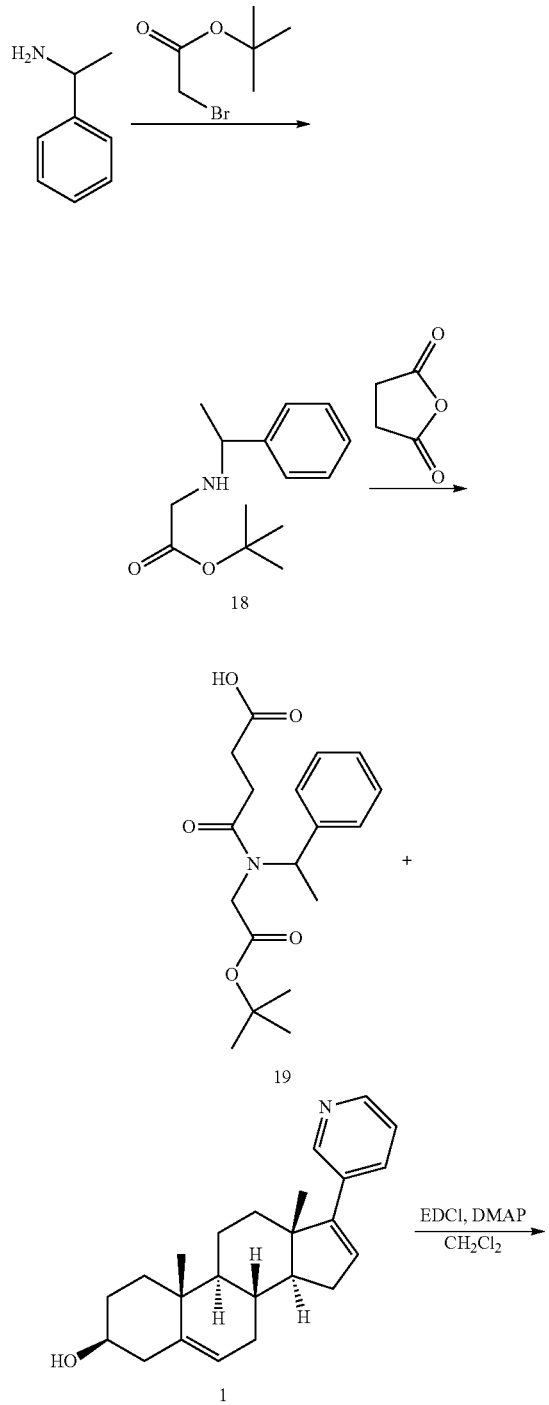

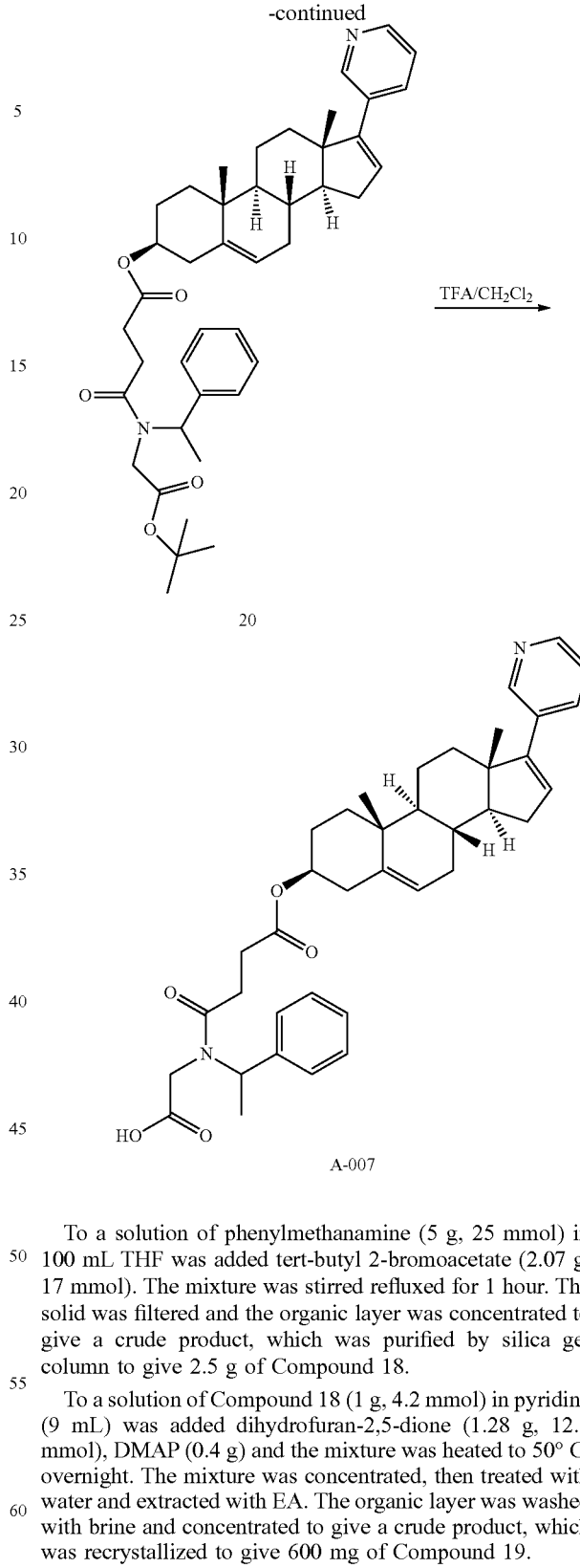

To a solution of phenylmethanamine (5 g, 25 mmol) in 100 mL THF was added tert-butyl 2-bromoacetate (2.07 g, 17 mmol). The mixture was stirred refluxed for 1 hour. The solid was filtered and the organic layer was concentrated to give a crude product, which was purified by silica gel column to give 2.5 g of Compound 18.

To a solution of Compound 18 (1 g, 4.2 mmol) in pyridine (9 mL) was added dihydrofuran-2,5-dione (1.28 g, 12.8 mmol), DMAP (0.4 g) and the mixture was heated to 50° C. overnight. The mixture was concentrated, then treated with water and extracted with EA. The organic layer was washed with brine and concentrated to give a crude product, which was recrystallized to give 600 mg of Compound 19.

To a solution of Compound 1 (200 mg, 0.573 mmol) in DCM (10 mL) was added Compound 19 (384 mg, 1.14 mmol). DMAP (35 mg, 0.287 mmol) was added and EDCI (391 mg, 1.3 mmol) was added at 0° C. The mixture was stirred at RT for 2 hours. Water was added and the solution was extracted with DCM. The organic layer was washed by brine dried by Na$_2$SO$_4$ and concentrated to give 40 mg crude product of Compound 20.

To a solution of Compound 20 (40 mg, crude) in DCM (10 mL) was added TFA (5 mL) dropwise at 0° C. The mixture was stirred at RT for overnight. The mixture was concentrated and purified by column chromatography to give 18 mg of A-007.

LC-MS: 611.6 (m+1)$^+$

Example 8: Synthesis of A-008

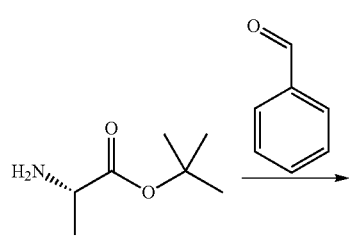

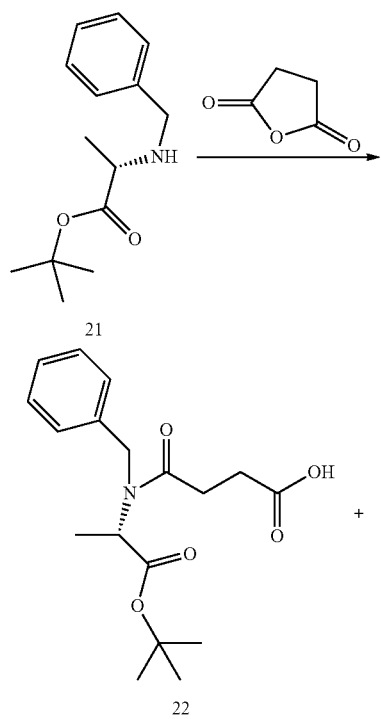

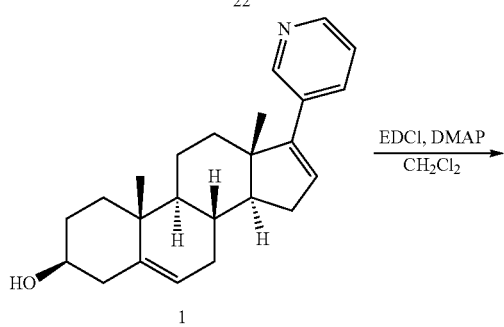

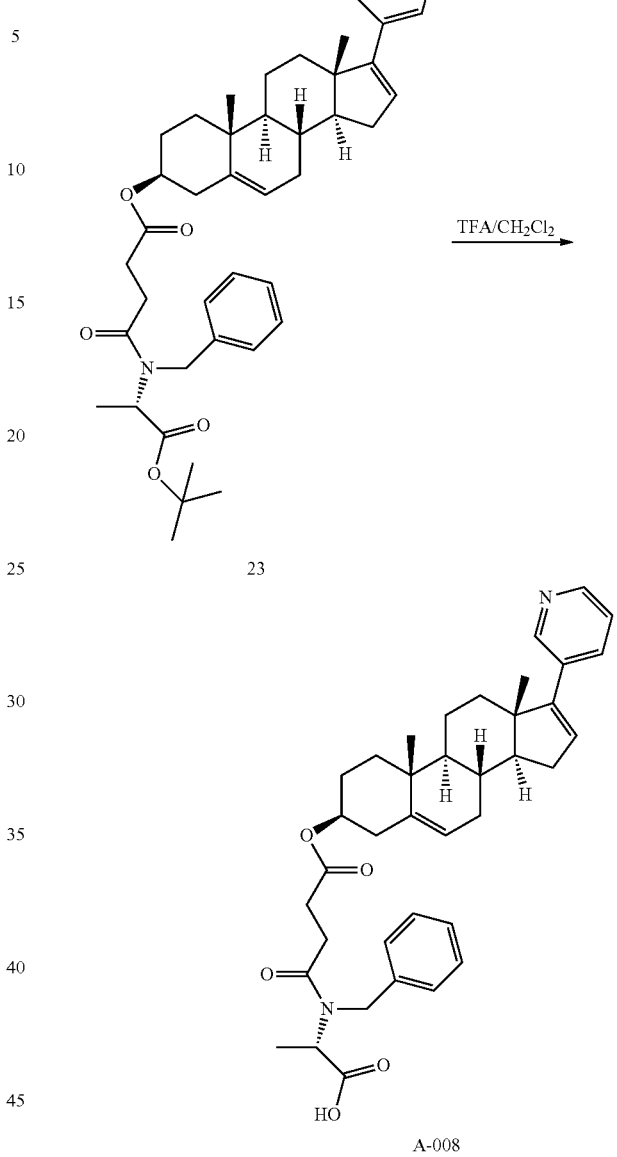

To a solution of (S)-tert-butyl 2-aminopropanoate (1.7 g, 11.8 mmol) in 30 mL MeOH was added benzaldehyde (1.4 g, 12.4 mmol) portionwise at RT. After 1 h, the mixture was added NaCNBH$_3$ (0.75 g, 11.8 mmol) and acetic acid ("AcOH") (1.42 g, 23.6 mmol). The mixture was stirred at RT for overnight. The mixture was concentrated, then added water and pH was adjusted to between 8-9 with NaHCO$_3$. The mixture was then extracted with EA. The organic layer was washed with water, brine and dried by Na$_2$SO$_4$, and then concentrated to give 2.4 g of Compound 21.

To a solution of Compound 21 (500 mg, 2.2 mmol) in pyridine (5 mL) was added dihydrofuran-2,5-dione (330 mg, 3.3 mmol), and the mixture was stirred at RT for overnight. The mixture was concentrated, then treated with water and extracted with EA. The organic layer was washed with brine and dried by Na$_2$SO$_4$ and concentrated to give a crude product, which was purified by silica gel column to give 400 mg of Compound 22.

To a solution of Compound 1 (94 mg, 0.27 mmol) in DCM (6 mL) was added Compound 22 (180 mg, 0.54 mmol). DMAP (17 mg, 0.14 mmol) was added and EDCI (186 mg, 0.945 mmol) was added at 0° C. The mixture was stirred at RT for overnight. Water was added and the solution was extracted with DCM. The organic layer was dried by Na₂SO₄ and concentrated to give a crude product, which was purified by silica gel column to give 150 mg of Compound 23.

To a solution of Compound 23 (150 mg, 0.225 mol) in DCM (8 mL) was added TFA (4 mL) dropwise at 0° C. The mixture was stirred at RT for overnight. The mixture was concentrated and extracted with DCM. The organic layer was dried by Na₂SO₄ and concentrated to give a crude product, which was purified by silica gel column to give 30 mg of A-008.

LC-MS: 611.6 (m+1)⁺

Example 9: Synthesis of A-009

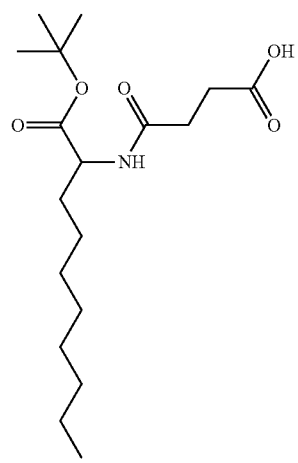

24

+

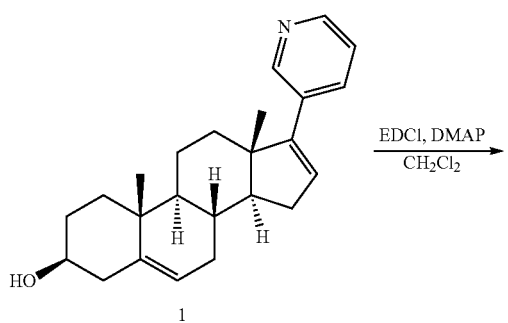

1

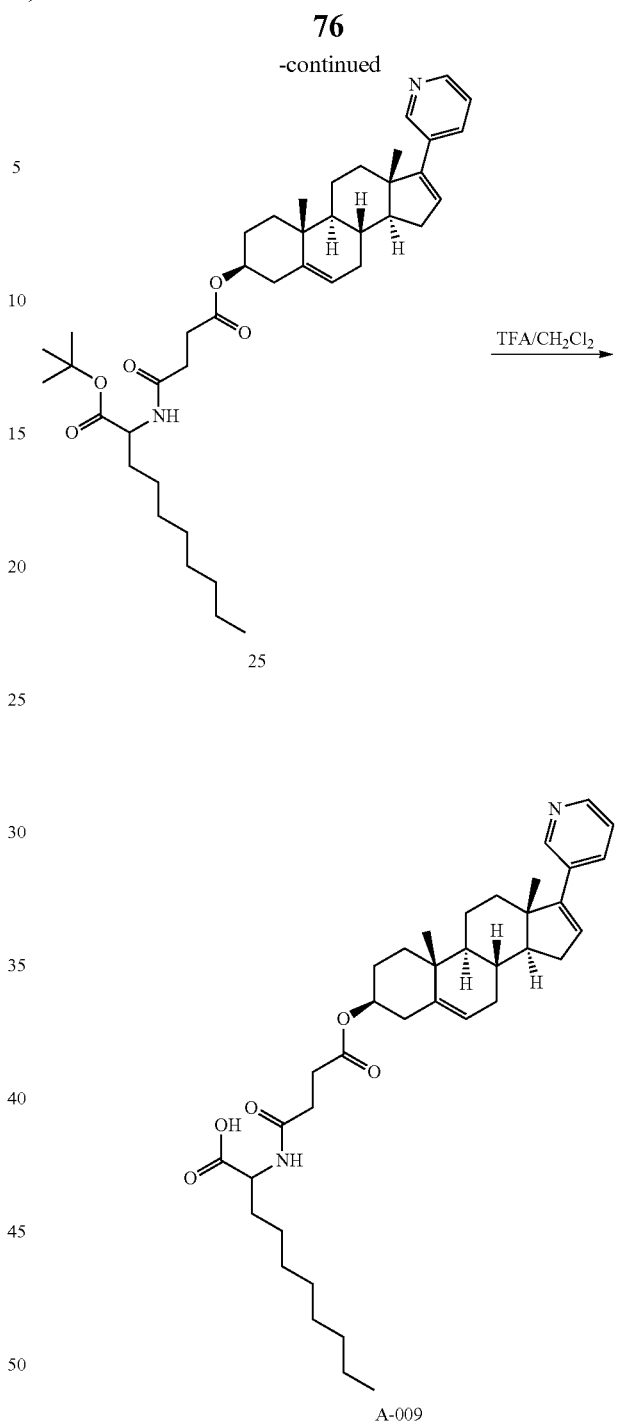

A-009

To a solution of Compound 1 (200 mg, 0.573 mmol) in DCM (10 mL) was added Compound 24 (390 mg, 1.15 mmol). DMAP (35 mg, 0.287 mmol) was added and EDCI (260 mg, 1.26 mmol) was added at 0° C. The mixture was stirred at RT for 2 hours. Water was added and the solution was extracted with DCM. The organic layer was washed by brine dried by Na₂SO₄ and concentrated to give a crude product, which was purified by column chromatography to give 200 mg of Compound 25.

To a solution of Compound 25 (200 mg) in DCM (10 mL) was added TFA (2 mL) dropwise at 0° C. The mixture was stirred at RT for overnight. The mixture was concentrated and crystallized from Et₂O to give 105 mg of A-009.

LC-MS: 619.6 (m+1)⁺

Example 10: Synthesis of A-010

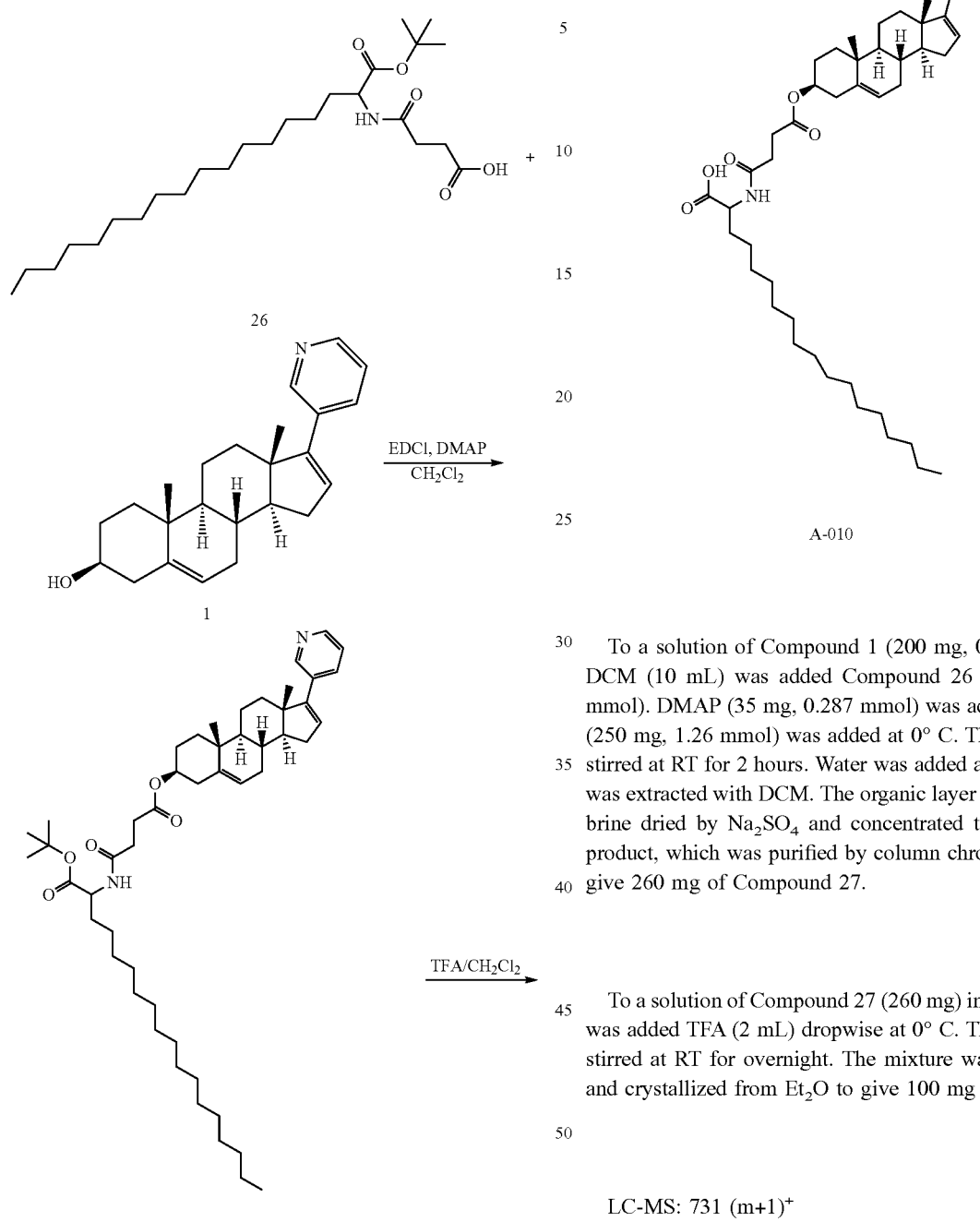
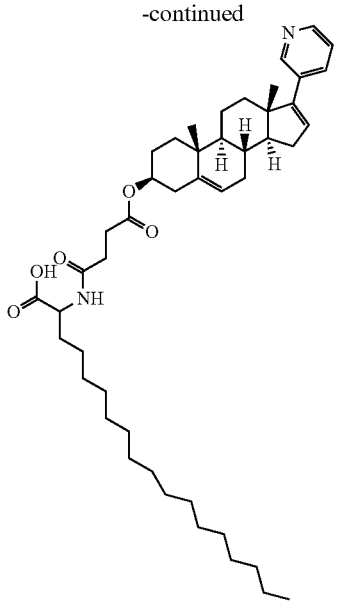

To a solution of Compound 1 (200 mg, 0.573 mmol) in DCM (10 mL) was added Compound 26 (520 mg, 1.15 mmol). DMAP (35 mg, 0.287 mmol) was added and EDCI (250 mg, 1.26 mmol) was added at 0° C. The mixture was stirred at RT for 2 hours. Water was added and the solution was extracted with DCM. The organic layer was washed by brine dried by Na$_2$SO$_4$ and concentrated to give a crude product, which was purified by column chromatography to give 260 mg of Compound 27.

To a solution of Compound 27 (260 mg) in DCM (10 mL) was added TFA (2 mL) dropwise at 0° C. The mixture was stirred at RT for overnight. The mixture was concentrated and crystallized from Et$_2$O to give 100 mg of A-010.

LC-MS: 731 (m+1)$^+$

Example 11: Synthesis of B-001

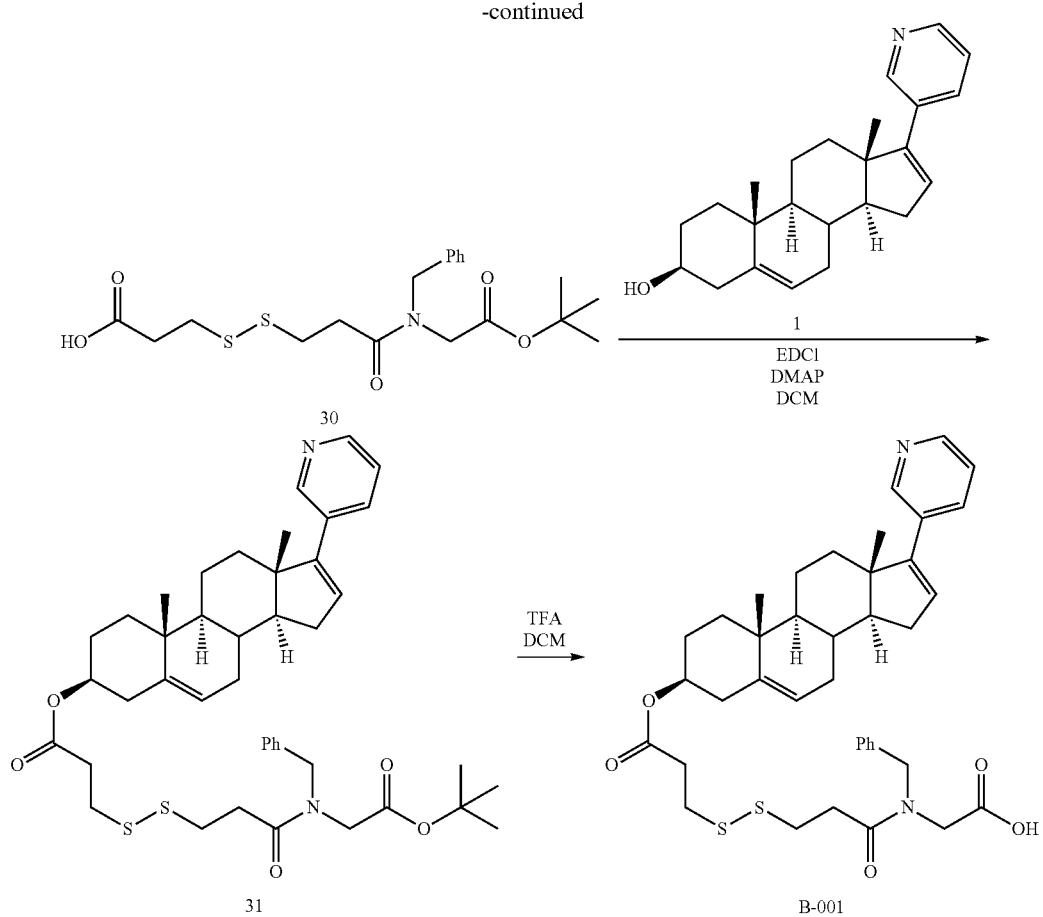

To a solution of compound 28 (5.7 g, 27.15 mmol) and compound 29 (3 g, 13.6 mmol) in 50 mL of dimethylformamide (DMF) at 0° C., EDCI (5.2 g, 27.15 mmol) and DMAP (828 mg, 6.8 mmol) were added. Then the reaction was stirred at RT for overnight. Water was added and extracted with EA. The organic layer was washed with water and brine, dried over $Na_2SO_4$, and concentrated to give a crude product, which was purified by column chromatography to give 3 g of compound 30. $^1$H NMR ($CDCl_3$, 300 MHz) δ: 1.4 (s, 9H), 2.7-3.1 (m, 8H), 3.9-4.2 (s, 2H), 4.6-4.7 (s, 2H), 7.2-7.5 (m, 5H)

LC-MS: m/z=436 (M+23)$^+$

To a solution of compound 30 (533 mg, 1.29 mmol), EDCI (247 mg, 1.29 mmol) and DMAP (42 mg, 0.344 mmol) in 30 mL of DCM at 0° C., compound 1 (300 mg, 0.86 mmol) was added into the solution. Then the reaction was stirred at RT for overnight. Water was added and extracted with DCM. The organic layer was washed with brine, dried over $Na_2SO_4$, concentrated to give a crude product, which was purified by column chromatography to give 250 mg of compound 31.

LC-MS: m/z=745 (M+1)

To a solution of compound 31 (250 mg) in 15 mL of DCM at 0° C., TFA (2 mL) was added. Then the reaction was stirred at RT for 1.5 h. The mixture was concentrated and purified by column chromatography to give 100 mg of B-001. $^1$HNMR ($CDCl_3$, 300 MHz) δ: 1.0-1.1 (d, 6H), 1.5-2.4 (m, 16H), 2.7-3.1 (m, 8H), 4.0-4.2 (m, 2H), 4.6-4.8 (m, 3H), 5.4-5.5 (d, 1H), 6.0-6.1 (d, 1H), 7.2-7.4 (m, 6H), 7.7-7.8 (m, 1H), 8.4-8.5 (d, 1H), 8.7 (s, 1H).

LC-MS: m/z=689 (M+1)$^-$

Example 11: Synthesis of B-002

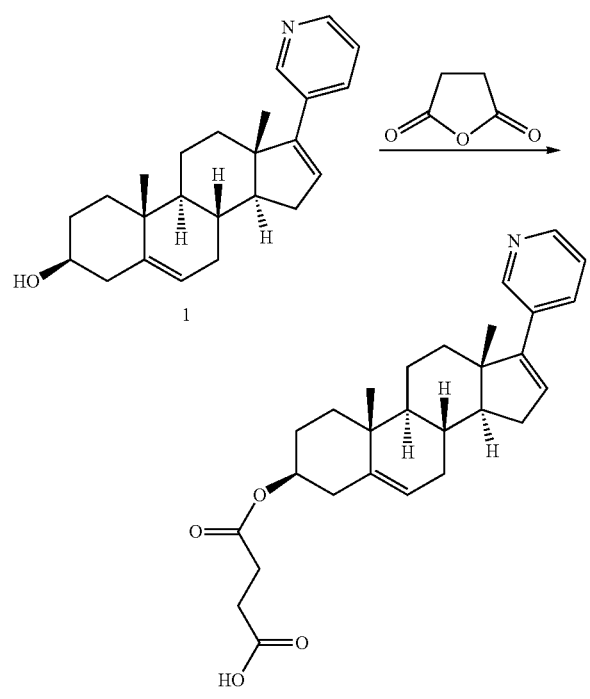

To a solution of abiraterone (500 mg, 1.43 mmol) in DMF/1,4-dioxane (7.5 mL/7.5 mL) was added succinic anhydride (700 mg, 7 mmol). DMAP (525 mg, 4.3 mmol) was added and the mixture was stirred at RT for overnight. Water was added and the mixture was extracted with EA twice. The organic layer was dried and concentrated. The crude product was purified by silica gel column to give 217 mg of B-002.

LC-MS: m/z=450.5 (M+1)$^+$

Example 12: Synthesis of B-003

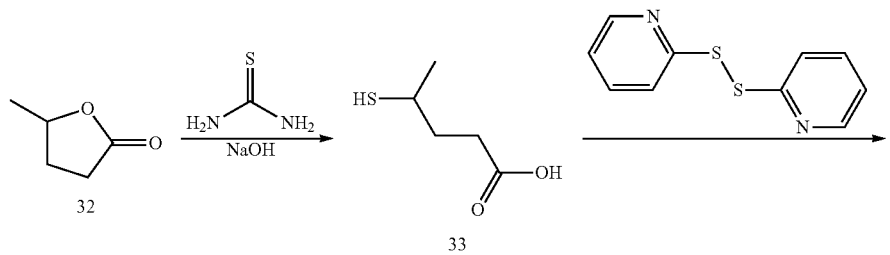

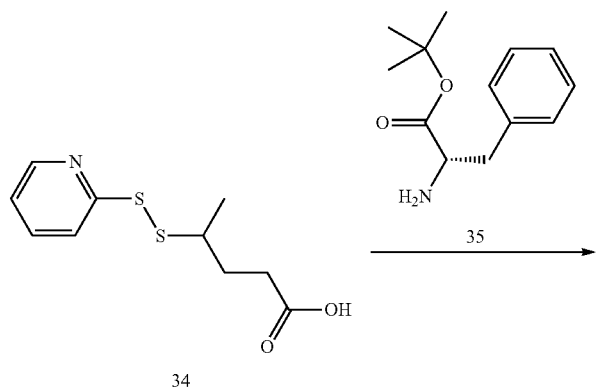

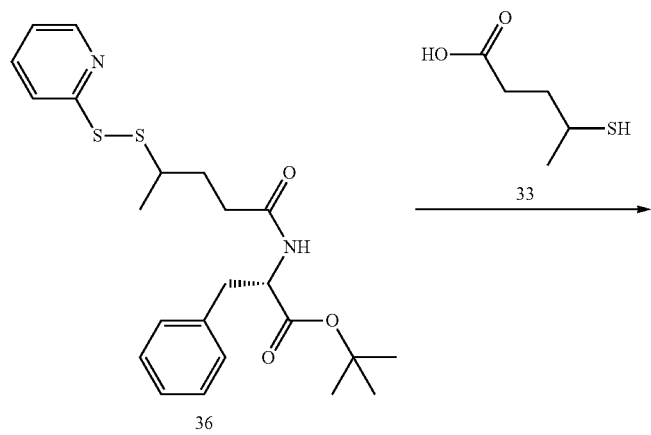

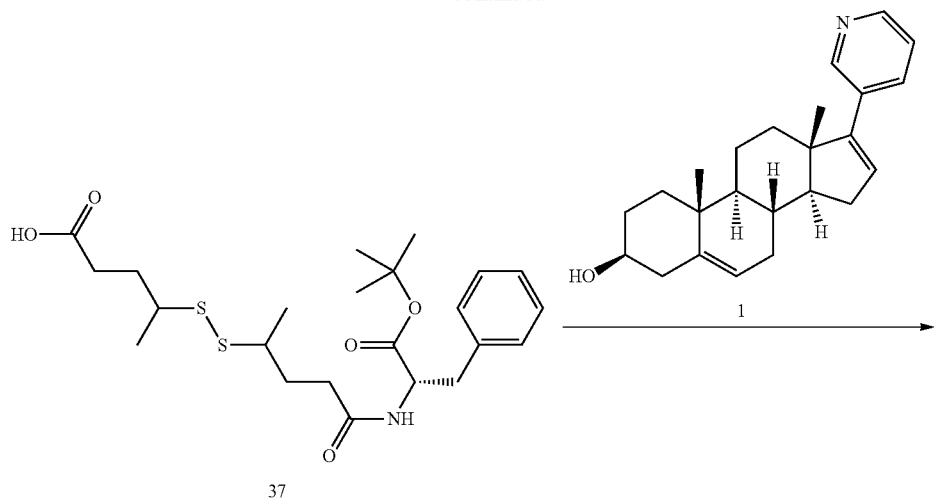

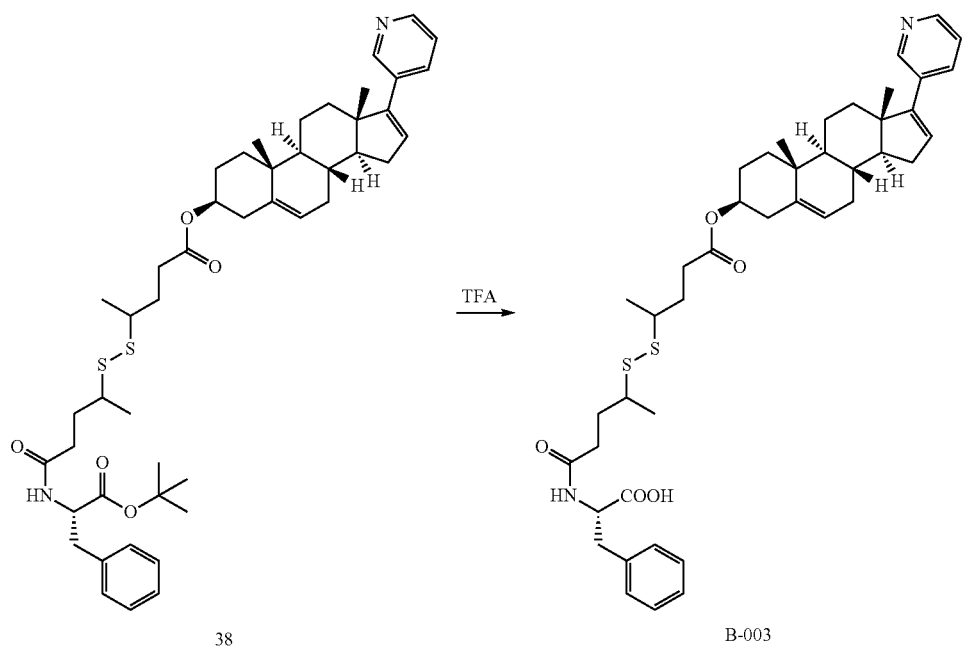 [SMILES: CC(CCC(=O)N[C@@H](Cc1ccccc1)C(=O)OC(C)(C)C)SSC(C)CCC(=O)O[C@H]1CC[C@@]2(C)C(=CC[C@@H]3[C@@H]2CC[C@]2(C)C(c4cccnc4)=CC[C@@H]32)C1 ; CC(CCC(=O)N[C@@H](Cc1ccccc1)C(=O)O)SSC(C)CCC(=O)O[C@H]1CC[C@@]2(C)C(=CC[C@@H]3[C@@H]2CC[C@]2(C)C(c4cccnc4)=CC[C@@H]32)C1 ; "B-003"]

To a solution of compound 32 (21 g, 210 mmol) in HBr (86.13 g, 425.8 mmol, 40%) was added thiourea (30.4 g, 399.5 mmol) under 70° C. The mixture was stirred at 100° C. overnight. Then the mixture was cooled and the pH was adjusted to 10, and stirred at 100° C. overnight. Then the reaction mixture was cooled and the pH was adjusted to 4-5. The mixture was extracted with ethyl acetate, washed with water and brine, dried over anhydrous $Na_2SO_4$, and concentrated to give a crude product, which was purified by a column chromatography to give compound 33 (7 g, 24.9%). $^1$HNMR (CDCl$_3$, 300 MHz) δ: 1.3-1.4 (d, 2H), 1.4-1.5 (d, 2H), 1.7-1.8 (m, 1H), 1.9-2.0 (m, 1H), 2.4-2.6 (m, 2H), 2.9-3.1 (m, 1H).

To a solution of compound 33 (5 g, 37.3 mmol) in MeOH (70 mL) was added 1,2-di(pyridin-2-yl)disulfane (12.3 g, 56 mmol). The mixture was stirred at room temperature overnight. The pH of the mixture was adjusted to 4-5. The mixture was extracted with ethyl acetate, washed with water and brine, dried over anhydrous $Na_2SO_4$, and concentrated to give a crude product, which purified by a column chromatography to give compound 34 (5.5 g, 60.7%). $^1$HNMR (CDCl$_3$, 300 MHz) δ: 1.3-1.4 (d, 2H), 1.8-2.05 (m, 2H), 2.5-2.6 (m, 2H), 3.0-3.1 (m, 1H), 7.0-7.2 (m, 1H), 7.6-7.7 (m, 1H), 7.7-7.8 (d, 1H), 8.4-8.5 (d, 1H).

To a solution of compound 34 (5.5 g, 22.6 mmol) and compound 35 (5.8 g, 22.6 mmol) in 50 mL of DMF at 0° C., EDCI (6.8 g, 35.3 mmol) and DMAP (828 mg, 6.8 mmol) were added. Then the reaction was stirred at room temperature overnight. Water was added and extracted with ethyl acetate. The organic layer was washed with water and brine, dried over anhydrous $Na_2SO_4$, and concentrated to give a crude product, which was purified by column chromatography to give 2.8 g of compound 36. $^1$HNMR (CDCl$_3$, 300 MHz) δ: 1.3-1.4 (m, 3H), 1.4-1.6 (s, 9H), 1.9-2.1 (m, 2H), 2.3-2.5 (m, 2H), 3.1-3.2.2 (m, 2H), 4.7-4.9 (m, 1H), 6.0-6.1 (m, 1H), 7.0-7.1 (m, 1H), 7.1-7.2 (m, 2H), 7.3-7.5 (m, 3H), 7.6-7.8 (m, 2H), 8.5 (m, 1H).

To a solution of compound 36 (1 g, 2.4 mmol) in dimethylformamide ("DMF") (5 mL), was added compound 33 (0.647 g, 4.8 mmol). The mixture was stirred at room temperature overnight. The mixture was extracted with EA. The organic layer was washed with water and brine, dried over anhydrous $Na_2SO_4$, and concentrated to give a crude product, which was purified by a column chromatography to give compound 37 (350 mg, 31%).

LC-MS: m/z=470 (M+1)⁻.

To a solution of compound 37 (350 mg, 0.74 mmol), EDCI (286 mg, 1.48 mmol) and DMAP (42 mg, 0.344 mmol) in 30 mL of DCM at 0° C., compound 1 (258 mg, 0.74 mmol) was added in the solution. Then the reaction mixture was stirred at room temperature for overnight. Water was added and extracted with ethyl acetate. The organic layer was washed with water and brine, dried over anhydrous $Na_2SO_4$, and concentrated to give a crude product, which was purified by column chromatography to give 300 mg of compound 38.

LC-MS: m/z=824 (M+23)⁺.

To a solution of compound 38 (300 mg) in 12 mL of $CH_2Cl_2$ at 0° C., TFA (2 mL) was added. Then the reaction mixture was stirred at room temperature for 2 hours. The mixture was concentrated and purified by column chromatography to give 66 mg of B-003. ¹HNMR (CDCl₃, 300 MHz) δ: 1.1-1.2 (s, 6H), 1.3-1.4 (m, 6H), 1.6-1.8 (m, 4H), 1.8-1.9 (m, 4H), 2.0-2.2 (m, 2H), 2.3-2.5 (m, 10H), 2.8-3.0 (m, 4H), 3.1-3.3 (m, 4H), 4.6-4.7 (m, 2H), 4.8-5.0 (m, 2H), 5.4-5.5 (m, 1H), 6.2-6.3 (m, 1H), 6.3-6.4 (m, 1H), 7.2-7.3 (m, 3H), 7.7-7.9 (m, 1H), 8.2-8.4 (m, 1H), 8.6-8.8 (m, 1H), 8.9-9.0 (m, 1H).

LC-MS: m/z=744 (M+1)⁺.

Example A: Non-Covalently Bound Complex of A-003 and HSA

In 2 vials, 1 mg of A-003 was dissolved in 0.5 mL methanol. Then 1.5 mL water at a pH of about 5 was added into each vial. The water with a pH of about 5 was prepared by adding 2 N HCl (aq.) into water. After shaking gently, a cloudy solution was obtained for both vials. 30.8 mg and 24.6 mg of HSA were then added, respectively, into the vials. After shaking gently, a slightly cloudy solution was obtained for both vials. Then methanol was removed under vacuum until the volume of the solution was about 1 mL. A clear water solution was obtained for the vial with 30.8 mg of HSA, and a slightly cloudy solution was obtained for the vial with 24.6 mg of HSA. The water solutions of the 2 vials were lyophilized overnight to give the white solids, which were reconstituted by adding 0.5 mL water into the vials. A clear water solution was obtained for the vial with 30.8 mg of HSA, and slightly cloudy solution was obtained for the vial with 24.6 mg of HSA.

TABLE 1

|  | HSA (mg) | |
| --- | --- | --- |
|  | 30.8 | 24.6 |
| Ratio of drug:HSA | 4 | 5 |

Example B: Non-Covalently Bound Complex of A-004 and HSA

In each of 3 vials, 1 mg of A-004 was dissolved in 0.5 mL of methanol. Then 1.5 mL of water with a pH about 5 was added into the vials. The water with a pH of about 5 was prepared by adding 2 N HCl (aq.) into water. After shaking gently, a clear solution was obtained for all 3 vials. 22.3 mg, 18.6 mg, and 15.9 mg of HSA were added, respectively, into the vials. After shaking gently, a cloudy solution was obtained for the vials with 18.6 mg and 15.9 mg of HSA, and a clear solution was obtained for the vial with 22.3 mg of HSA. Then methanol was removed under vacuum until the volume of the solution was about 1 mL. A clear water solution was obtained for the vials with 22.3 mg and 18.6 mg of HSA, and a cloudy solution was obtained for the vial with 15.9 mg of HSA. The water solutions of the 3 vials were lyophilized overnight to give the white solids, which were reconstituted by adding 0.5 mL of water into the vials. A clear water solution was obtained for the vials with 22.3 mg and 18.6 mg of HSA, and a cloudy solution was obtained for the vial with 15.9 mg of HSA.

TABLE 2

|  | HSA (mg) | | |
| --- | --- | --- | --- |
|  | 22.3 | 18.6 | 15.9 |
| Ratio of drug:HSA | 5 | 6 | 7 |

Example C: Non-Covalently Bound Complex of A-005 and HSA

In each of 3 vials, 1 mg of A-005 was dissolved in 0.5 mL of methanol. Then 1.5 mL of water with a pH about 5 was added into each vial. The water with a pH of about 5 was prepared by adding 2 N HCl (aq.) into water. After shaking gently, a clear solution was obtained for all 3 vials. 27.2 mg, 21.8 mg and 18.1 mg of HSA were added, respectively, into the vials. After shaking gently, a clear water solution was obtained for the vial with 27.2 mg of HSA, and a cloudy solution was obtained for the vials with 21.8 mg and 18.1 mg of HSA. Then methanol was removed under vacuum until the volume of the solution was about 1 mL. A clear water solution was obtained for the vial with 27.2 mg of HSA, and a cloudy solution was obtained for the vials with 21.8 mg and 18.1 mg of HSA. The water solutions of the 3 vials were lyophilized overnight to give the white solids, which were reconstituted by adding 0.5 mL water into the vials. A clear water solution was obtained for the vial with 27.2 mg of HSA, and a cloudy solution was obtained for the vials with 21.8 mg and 18.1 mg of HSA.

TABLE 3

|  | HSA (mg) | | |
| --- | --- | --- | --- |
|  | 27.2 | 21.8 | 18.1 |
| Ratio of drug:HSA | 4 | 5 | 6 |

Example D: Non-Covalently Bound Complex of A-006 and HSA

In each of 3 vials, 1 mg of A-006 was dissolved in 0.5 mL of methanol. Then 1.5 mL of water with a pH of about 5 was added into each vial. The water with a pH of about 5 was prepared by adding 2 N HCl (aq) into water. After shaking gently, a clear solution was obtained for all 3 vials. 27.2 mg, 21.8 mg and 18.1 mg of HSA were added, respectively, into the vials. After shaking gently, a clear solution was obtained for vials with 27.2 mg and 21.8 mg of HSA, a cloudy solution was obtained for the vial with 18.1 mg of HSA. Then methanol was removed under vacuum until the volume of the solution was about 1 mL. A clear water solution was obtained for the vials with 27.2 mg and 21.8 mg of HSA, and a cloudy solution was obtained for the vial with 18.1 mg of HSA. The water solutions of the 3 vials were lyophilized overnight to give the white solids, which were reconstituted by adding 0.5 mL water into the vials. A clear water solution was obtained for the vials with 27.2 mg and 21.8 mg of HSA, and a cloudy solution was obtained for the vial with 18.1 mg of HSA.

TABLE 4

|  | HSA (mg) | | |
|---|---|---|---|
|  | 27.2 | 21.8 | 18.1 |
| Ratio of drug:HSA | 4 | 5 | 6 |

Example E: Non-Covalently Bound Complex of A-008 and HSA

In each of 3 vials, 1 mg of A-008 was dissolved in 0.5 mL methanol. Then 1.5 mL of water with a pH of about 5 was added into each of 3 vials. The water with a pH of about 5 was prepared by adding 2 N HCl (aq.) into water. After shaking gently, a clear solution was obtained for all 3 vials. 27.2 mg, 21.8 mg and 18.1 mg of HSA were added, respectively, into the vials. After shaking gently, a clear solution was obtained for vials with 27.2 mg and 21.8 mg of HSA, a cloudy solution was obtained for the vial with 18.1 mg of HSA. Then methanol was removed under vacuum until the volume of the solution was about 1 ml. A clear water solution was obtained for the vials with 27.2 mg and 21.8 mg of HSA, and a cloudy solution was obtained for the vial with 18.1 mg of HSA. The water solutions of the 3 vials were lyophilized overnight to give the white solids, which were reconstituted by adding 0.5 mL water into the vials. A clear water solution was obtained for the vials with 27.2 mg and 21.8 mg of HSA, and a cloudy solution was obtained for the vial with 18.1 mg of HSA.

TABLE 5

|  | HSA | | |
|---|---|---|---|
|  | 27.2 mg | 21.8 mg | 18.1 mg |
| Ratio of drug:HSA | 4 | 5 | 6 |

Example F: Non-Covalently Bound Complex of B-001 and HSA

In each of 2 vials, 1 mg of B-001 was dissolved in 0.5 mL methanol/DMF (4:1). Then 1.0 mL of water with a pH of about 5 was added into each vial. The water with a pH of about 5 was prepared by adding 2 N HCl (aq.) into water. After shaking gently, a slightly cloudy solution was obtained for all 2 vials. 24.1 mg and 19.3 mg of HSA were added, respectively, into the vials. After shaking gently, then methanol was removed under vacuum until the volume of the solution was about 1 mL. A clear water solution was obtained for the vial with 24.1 mg of HSA, and a cloudy solution was obtained for the vial with 19.3 mg of HSA. The water solutions of the 2 vials were lyophilized overnight to give the white solids, which were reconstituted by adding 0.5 mL water into the vials. A clear water solution was obtained for the vial with 24.1 mg of HSA, and a cloudy solution was obtained for the vial with 19.3 mg of HSA.

TABLE 6

|  | HSA | |
|---|---|---|
|  | 24.1 mg | 19.3 mg |
| Ratio of drug:HSA | 4 | 5 |

Example G: Non-Covalently Bound Complex of B-002 and HSA

In each of 2 vials, 3 mg of B-002 was dissolved in 3 mL methanol/DMF (4:1). In another 2 vials, 111 mg and 148 mg of HSA were dissolved in 6 mL water, respectively. Then methanol solution of B-002 was added slowly into the vials of HSA with shaking, respectively. A clear solution was obtained in both vials. Then methanol was removed under vacuum until the volume of the solution was about 3-4 mL. A clear water solution was obtained for both vials. The water solutions of the 2 vials were lyophilized overnight to give white solids. 50 mg of the solids were reconstituted by adding 0.5 mL of water into the vials. A clear water solution was obtained for both vials.

TABLE 7

|  | HSA | |
|---|---|---|
|  | 148 mg | 111 mg |
| Ratio of drug:HSA | 3 | 4 |

Example H: Non-Covalently Bound Complex of B-003 and HSA 25 mg of B-003 was dissolved in 12.5 mL ethanol/DMF (4:1) in a flask. Then 557.5 mg of HSA was dissolved in 25 mL of water with a pH of about 5 in another flask. The water with a pH of about 5 was prepared by adding 2 N HCl (aq.) into water. The solution of B-003 was added slowly into the HSA water solution with stirring. After addition, a clear solution was obtained. Then ethanol was removed under vacuum until the volume of the solution was about 25-26 mL. A clear aqueous solution was obtained. The aqueous solution was lyophilized overnight to give a white solid, which was reconstituted by adding 0.5 mL water into the vial. A clear water solution was obtained.

Example AA: Persistence in Plasma

Test compounds and control (procaine) were incubated at a concentration of 10 µM with human plasma. The duplicate incubations, conducted in 96-well plates in a shaking water bath maintained at 37° C., were performed for 0 and 60 minutes and quenched by addition of acetonitrile. Ingredients for different incubations were added as shown in Table 8.

TABLE 8

Plasma Data

| Components | Add (μL) | | |
|---|---|---|---|
| | 0 min | 24 hr | 24 hr in PBS |
| Plasma | 100 | 100 | 0 |
| Phosphate-buffered saline (PBS) Buffer (pH 7.4) | 90 | 90 | 90 |
| 20 μM Test Compound or Control in Dimethyl sulfoxide (DMSO):PBS buffer (1:1) | 0 | 10 | 10 |
| Vortex | No | Yes | Yes |
| Incubated at 37° C. for 24 hr | Yes | Yes | Yes |
| Vortex | Yes | No | No |
| ACN (μL) | 500 | 500 | 500 |
| 20 μM Test Compound or Control in DMSO:PBS buffer (1:1) | 10 | 0 | 0 |
| Plasma | 0 | 0 | 100 |
| IS Solution (25 μg/mL) (μL) | 20 | 20 | 20 |
| Vortex | Yes | Yes | Yes |
| Centrifuge at 3500 rpm for 10 min | Yes | Yes | Yes |

After quenching by acetonitrile, the plates were capped, vortexed, and centrifuged at 3000 rpm for 10 minutes. The supernatant was injected into LC-MS/MS.

Peak area ratios of procaine and test compounds in incubation samples are listed in Table 9. Percent remaining values are calculated from peak area ratios from the equation shown below and are listed in Table 10.

$$\% \text{Remaining} = 100 * \frac{PeakArea\ 1\ hr}{(PeakArea\ 0\ h - \text{Replicate 1} + PeakArea\ 0\ h - \text{Replicate 2})/2}$$

TABLE 9

Procaine and Test Compound Peak Area Ratio in Incubation Samples

| | Peak Area Ratio (Analyte/IS) | | | | | |
|---|---|---|---|---|---|---|
| | Human Plasma | | | | PBS Buffer | |
| | 0 hr | | 24 hr | | 24 hr | |
| Compound | Replicate 1 | Replicate 2 | Replicate 1 | Replicate 2 | Replicate 1 | Replicate 2 |
| Procaine | 0.443 | 0.444 | 0.0 | 0.0 | 0.0916 | 0.357 |
| A004 and HSA Complex | 1.16 | 1.13 | 1.14 | 1.11 | 1.0 | 1.09 |
| B001 and HSA complex | 0.753 | 0.741 | 0.689 | 0.664 | 0.706 | 0.722 |

TABLE 10

Percent Remaining of Procaine and Test Compounds after 24-hr Incubation

| | % Remaining after 24-hr Incubation at 37° C. | | | | | |
|---|---|---|---|---|---|---|
| | Human Plasma | | | PBS buffer | | |
| Compound | Replicate 1 | Replicate 2 | Average | Replicate 1 | Replicate 2 | Average |
| Procaine | 0.0 | 0.0 | 0.0 | 20.65 | 80.5 | 51 |
| A-004 and HSA Complex | 100.0 | 97.0 | 98.5 | 87.3 | 95.2 | 91.3 |
| B001 and HSA Complex | 92.0 | 89.0 | 90.5 | 94.5 | 96.7 | 95.6 |

Example AB: Pharmacokinetics Study of Non-Covalently Bound Complex of B-001-HSA

Figure 2:
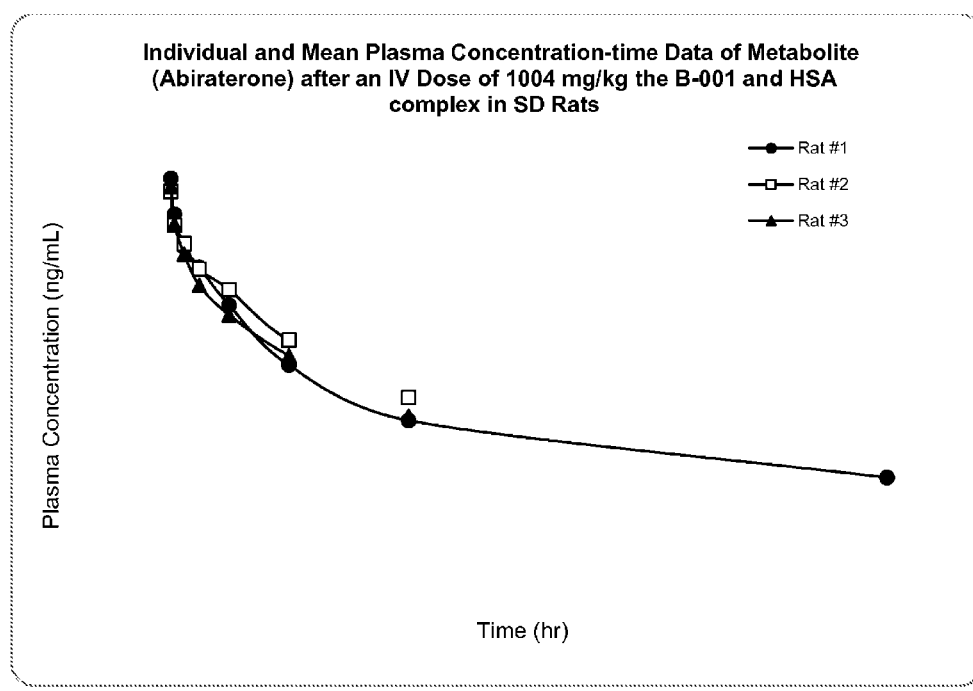
FIG. 2 shows individual and mean plasma concentration-time data for abiraterone after an IV dose of 1004 mg/kg of the Compound B-001-HSA complex in SD rats.

A group of 3 Sprague Dawley® ("SD") male rats were used in pharmacokinetics study. The dosing route of the study was IV. The dose for the PK study of non-covalently bound complex of B-001 and HSA was 1004 mg/kg (an equivalent of a dose of 40 mg/kg of B-001). The 10 time points for the study were 0.05, 0.167, 0.5, 1, 2, 4, 8, 24, 36 and 72 hr post dose. All blood samples were collected from cannula on the jugular vein. Blood samples were transferred into EDTA-K2 anti-coagulant tube and immediately placed on ice. After mixing on a rotator for 1 minute, the blood samples were centrifuged for 5 min at 3000× gravity ("g") and plasma was transferred to a microcentrifuge tube and kept in −80° C. freezer until processed for bio-analysis. An LC-MS/MS method was developed for compound B-001 and abiraterone in male SD rat plasma. Abiraterone can be formed in vivo after compound B-001 dissociates from HSA and is metabolized at the ester bond (e.g., undergoes hydrolysis). FIG. 1 shows individual and mean plasma concentration-time data for Compound B-001 after an IV dose of 1004 mg/kg of the Compound B-001-HSA complex in SD rats. FIG. 2 shows individual and mean plasma concentration-time data for abiraterone after an IV dose of 1004 mg/kg of the Compound B-001-HSA complex in SD rats.

TABLE 11

| Compound | Clearance ("CL") (mL/min/kg) | Volume of distribution ("Vss") (L/kg) | Terminal $T_{1/2}$ (hr) | Area Under the Curve ("$AUC_{last}$") (hr * ng/mL) |
|---|---|---|---|---|
| B-001 | 32.8 | 0.203 | 1.09 | 28145 |
| abiraterone | 61.1 | 2.92 | 1.93 | 5514 |

Figure 3:
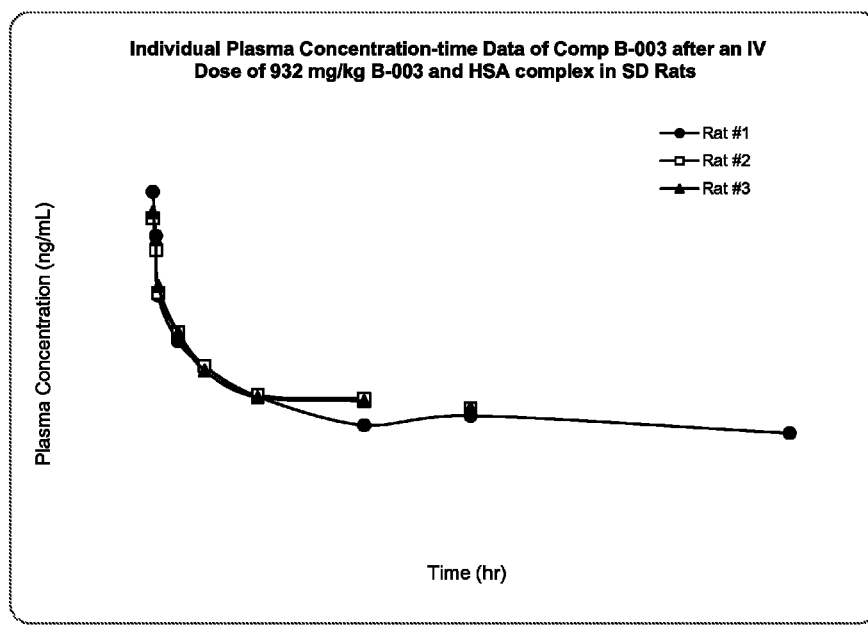
FIG. 3 shows individual plasma concentration-time data for Compound B-003 after an IV dose of 932 mg/kg of the Compound B-003-HSA complex in SD rats.
Figure 4:
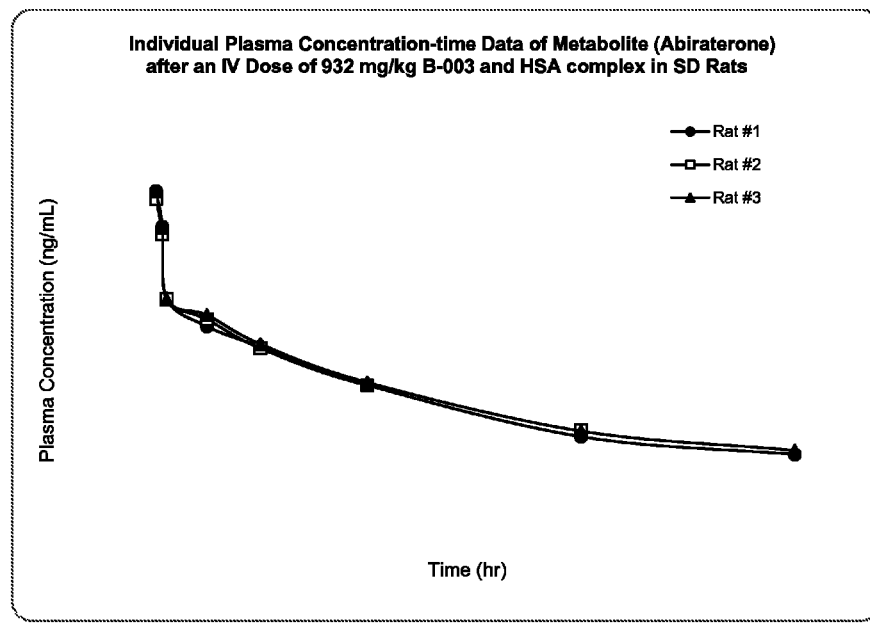
FIG. 4 shows the individual plasma concentration-time data for the B-003 metabolite (abiraterone) after an IV dose of 932 mg/kg of the B-003-HSA complex in SD rats

Example AC: Pharmacokinetics Study of Non-Covalently Bound Complex of B-003 and HSA A group of 3 SD male rats was used in pharmacokinetics study. The dosing route of the study was IV. The dose for the PK study of Non-covalently bound complex of B-003 and HSA was 1004 mg/kg (an equivalent of a dose of 40 mg/kg of B-003). The 10 time points for the study were 0.05, 0.167, 0.5, 1, 2, 4, 8, 24, 36 and 72 hr post dose. All blood samples were collected from the cannula on the jugular vein. Blood samples were transferred into an EDTA-K2 anti-coagulant tube and immediately placed on ice. After mixing on rotator for 1 min, the blood sample was centrifuged for 5 min at 3000×g and plasma was transferred to a microcentrifuge tube and kept in −80° C. freezer until processed for bioanalysis. An LC-MS/MS method was developed for compound B-003 and abiraterone in male SD rat plasma. Abiraterone can be formed in vivo after compound B-003 dissociates from HSA and is metabolized at the ester bond (e.g., undergoes hydrolysis). FIG. 3 shows individual plasma concentration-time data for Compound B-003 after an IV dose of 932 mg/kg of the Compound B-003-HSA complex in SD rats. FIG. 4 shows the individual plasma concentration-time data abiraterone after an IV dose of 932 mg/kg of the B-003-HSA complex in SD rats.

TABLE 12

| Compound | CL (mL/min/kg) | Vss (L/kg) | Terminal $T_{1/2}$ (hr) | $AUC_{last}$ (hr * ng/mL) |
|---|---|---|---|---|
| B-003 | 79.1 | 2.86 | 10.7 | 10174 |
| abiraterone | 50.8 | 0.598 | 1.79 | 5998 |

A number of embodiments have been described. Nevertheless, it will be understood that various modifications may be made without departing from the spirit and scope of the disclosure. Accordingly, other embodiments are within the scope of the following claims.

What is claimed is:

1. A non-covalently bound complex of an abiraterone derivative and human serum albumin in a molar ratio from about 1:1 to about 10:1, wherein:
   the non-covalently bound complex has a solubility in aqueous solution of at least 5 mg/mL, and the abiraterone derivative comprises a compound of Formula (I):

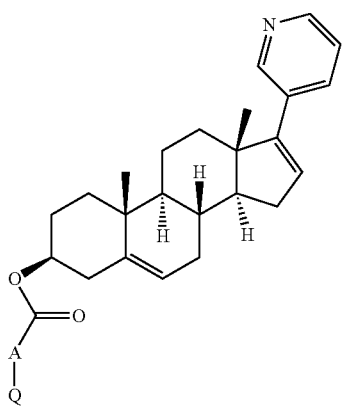

(I)

wherein
A is a covalent bond, O or NR$^1$;
R$^1$ is H, lower alkyl, or alkaryl, wherein the alkyl or alkaryl is optionally substituted with 1-3 substituents independently selected from the group consisting of: halo, nitro, amine, amide, hydroxyl, O-lower alkyl and carboxy; and
Q is a group that selectively binds to human serum albumin.

2. The non-covalently bound complex of claim 1, wherein Q comprises —COOH.

3. A compound, or a pharmaceutically acceptable salt thereof, according to Formula (II):

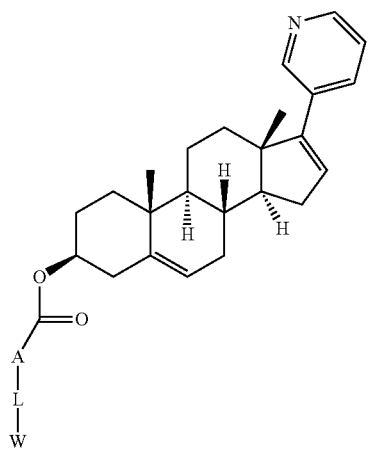

(II)

wherein
A is a covalent bond, O or NR$^1$;
L is alkyl, alkyl-O-alkyl, alkenyl, alkynyl, carbocyclyl, carbocyclylalkyl, aryl, alkaryl, or

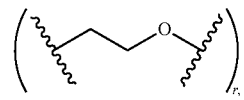

each of which is optionally substituted with 1-3 substituents independently selected from the group consisting of halo, —NO$_2$, amine, amide, hydroxyl, O-lower alkyl and —COOH, provided that there be no covalent bonds between oxygen atoms;
W is

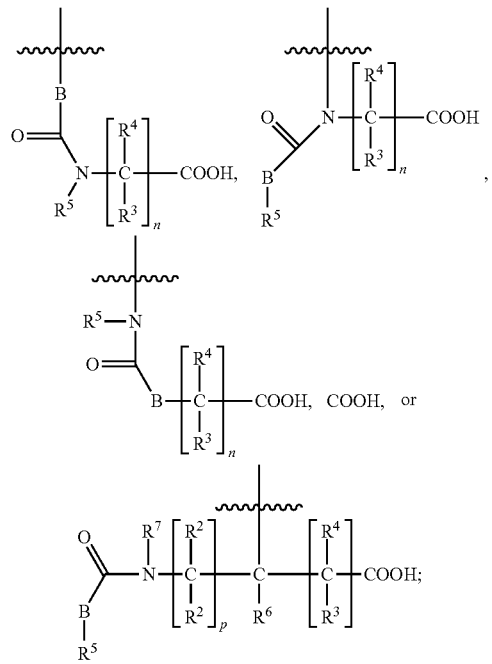

R$^1$ is H, lower alkyl, or alkaryl, wherein the alkyl or alkaryl is optionally substituted with 1-3 substituents independently selected from the group consisting of: halo, $NO_2$, amine, amide, hydroxyl, 0-lower alkyl and —COOH;

$R^2$ is independently in each instance H, OH, $NO_2$, $NH_2$, $NH_3^+$, SH or a branched or unbranched $C_{1-8}$ alkyl, $C_{2-8}$ alkenyl or $C_{2-8}$ alkynyl, wherein the $C_{1-8}$ alkyl, $C_{2-8}$ alkenyl or $C_{2-8}$ alkynyl is optionally substituted with 1-2 substituents independently selected from the group consisting of halo, OH, $NO_2$, $NH_2$, $NH_3^+$, SH and =O, and wherein the $C_{1-8}$ alkyl, $C_{2-8}$ alkenyl or $C_{2-8}$ alkynyl optionally has 1-2 heteroatoms independently selected from O, S and NH wherein each heteroatom replaces a $CH_2$, with the proviso that no O, S or N atom in the $C_{1-8}$ alkyl, $C_{2-8}$ alkenyl or $C_{2-8}$ alkynyl is covalently bonded to another O, S or N atom;

$R^3$ is independently in each instance H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl;

$R^4$ is independently in each instance H, OH, $NO_2$, $NH_2$, $NH_3^+$, SH or a branched or unbranched $C_{1-10}$ alkyl, $C_{2-10}$ alkenyl or $C_{2-10}$ alkynyl, wherein the $C_{1-10}$ alkyl, $C_{2-10}$ alkenyl or $C_{2-10}$ alkynyl is optionally substituted with 1-2 substituents independently selected from the group consisting of halo, OH, $NO_2$, $NH_2$, $NH_3^+$, SH and =O, and wherein the $C_{1-10}$ alkyl, $C_{2-10}$ alkenyl or $C_{2-10}$ alkynyl optionally has 1-2 heteroatoms independently selected from O, S and NH wherein each heteroatom replaces a $CH_2$, with the proviso that no O, S or N atom in the $C_{1-10}$ alkyl, $C_{2-10}$ alkenyl or $C_{2-10}$ alkynyl is covalently bonded to another O, S or N atom;

$R^5$ is H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl;

$R^6$ and $R^7$ is each independently H or lower alkyl, optionally substituted with 1-3 substituents independently selected from the group consisting of halo, nitro, amine, amide, hydroxyl, O-lower alkyl and carboxy;

B is a covalent bond, O or $NR_1$;

p is 1, 2, 3, 4, 5, or 6;

n is 1, 2, 3, 4, 5, or 6; and r is 1, 2, 3, 4, 5, 6, 7, 8, 9, or 10.

4. The compound of claim 3, or pharmaceutically acceptable salt thereof, wherein W is

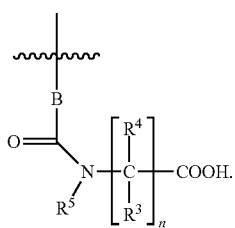

5. The compound of claim 3, or pharmaceutically acceptable salt thereof, wherein: L is an alkyl, an alkenyl or alkynyl, wherein the alkyl, alkenyl, or alkynyl is optionally substituted with 1-3 substituents independently selected from the group consisting of halo, —$NO_2$, amine, amide, hydroxyl, O-lower alkyl and —COOH.

6. The compound of claim 3, or pharmaceutically acceptable salt thereof, wherein the compound has the structure:

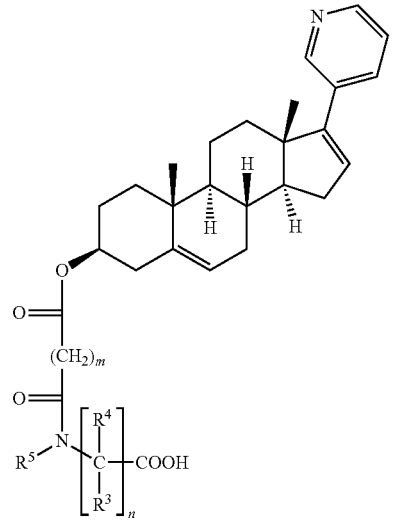

wherein m is 0, 1, 2, 3, 4, 5, 6, 7, or 8.

7. The compound of claim 3, or pharmaceutically acceptable salt thereof, wherein the compound has the structure:

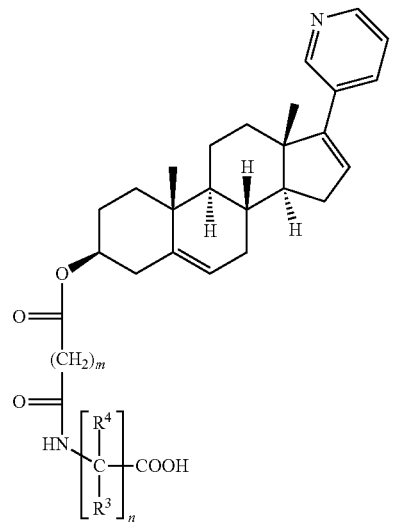

wherein m is 0, 1, 2, 3, 4, 5, 6, 7, or 8.

8. The compound of claim 3, or pharmaceutically acceptable salt thereof, wherein $R^3$ is independently in each instance H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, —O-aryl.

9. The compound of claim 3, or pharmaceutically acceptable salt thereof, wherein $R^5$ is H, alkyl, phenyl, or alkaryl, wherein the alkyl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl.

10. The compound of claim 3, or pharmaceutically acceptable salt thereof, wherein the compound is selected from the group consisting of:
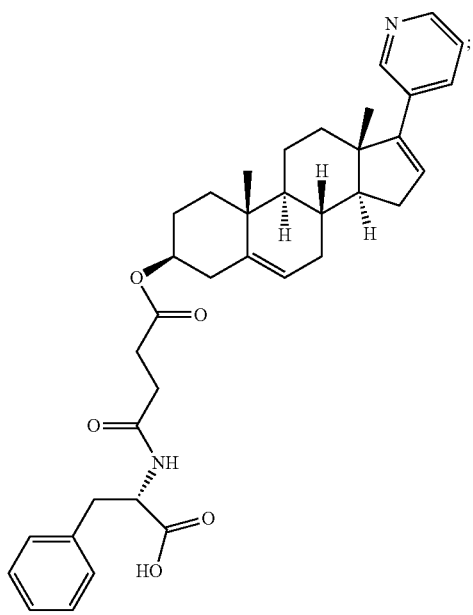
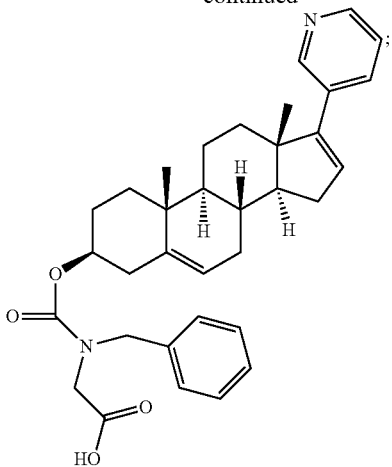
-continued
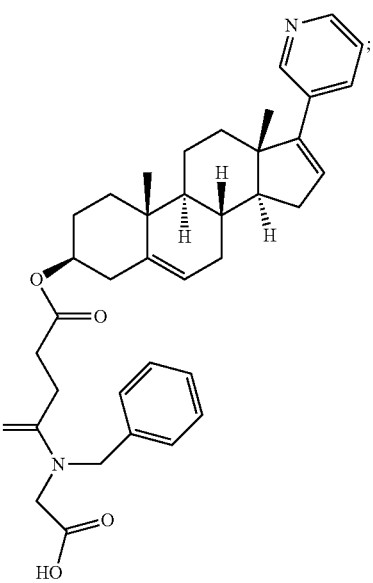
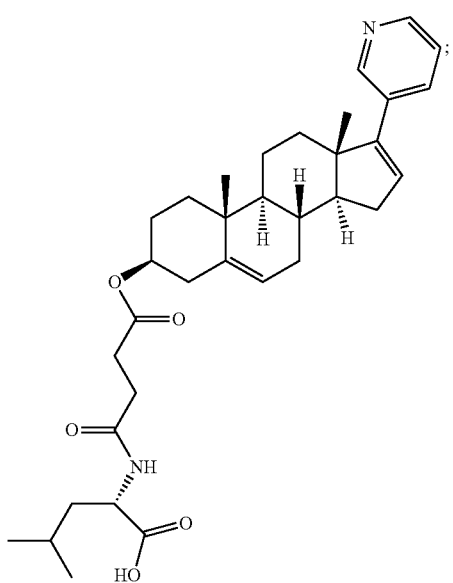
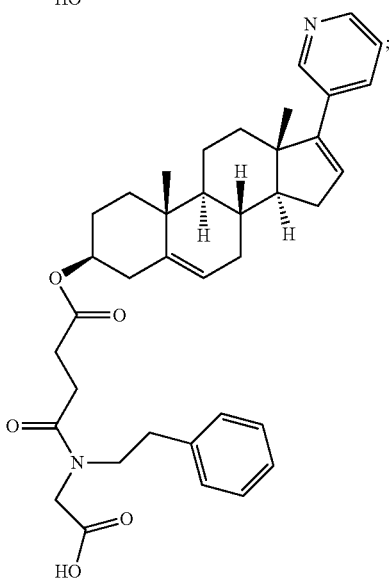

97
-continued
98
-continued
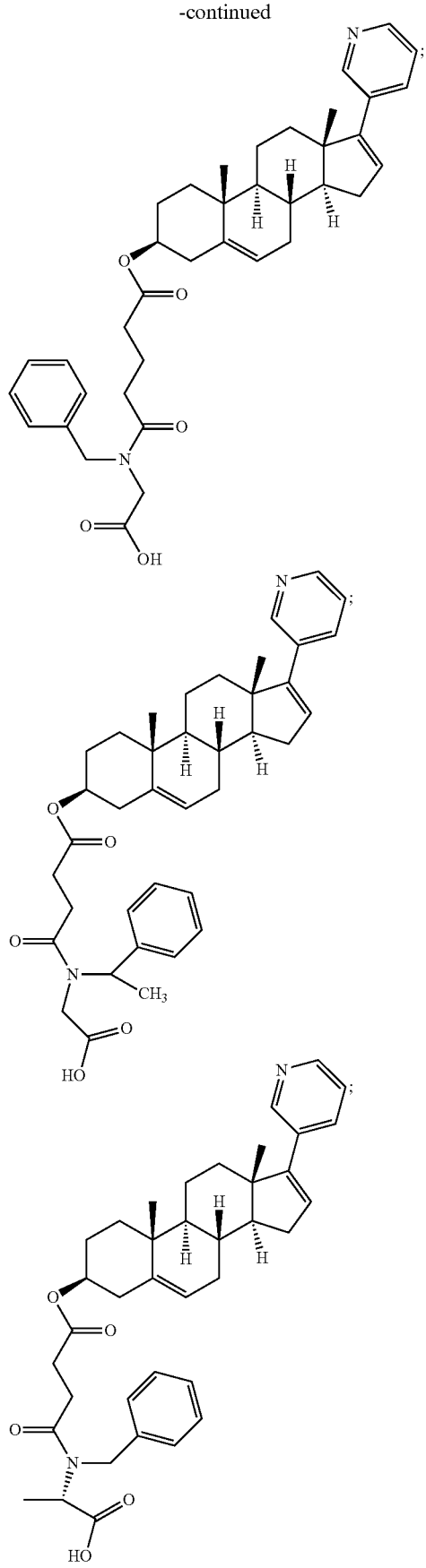
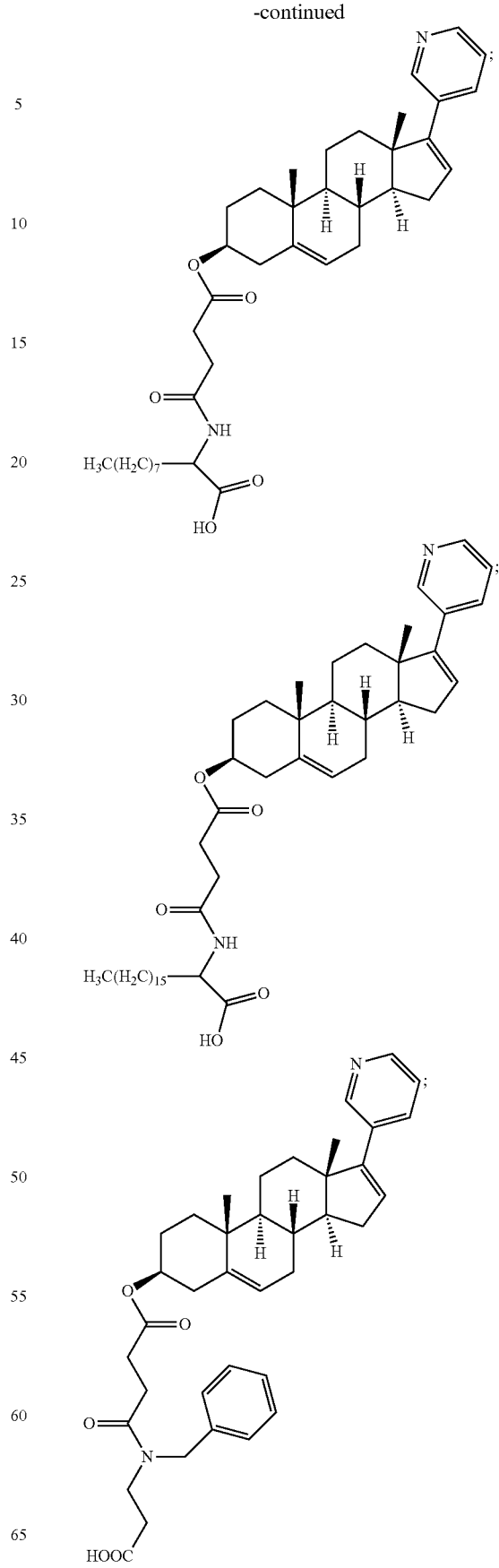

99
-continued
100
-continued
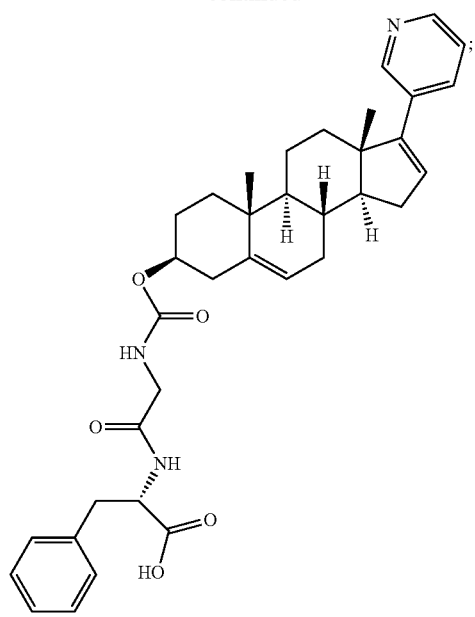
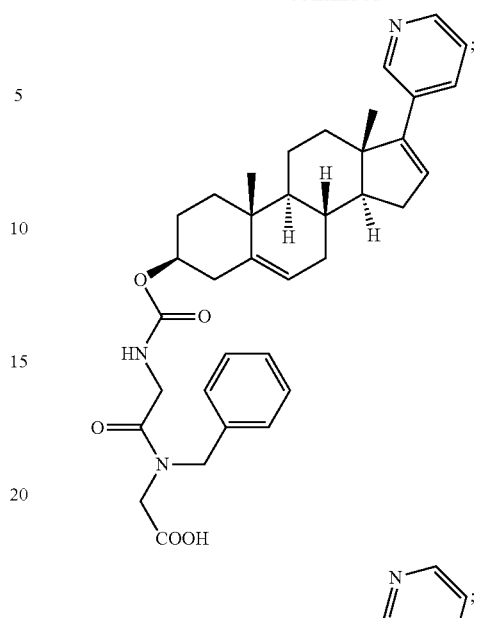
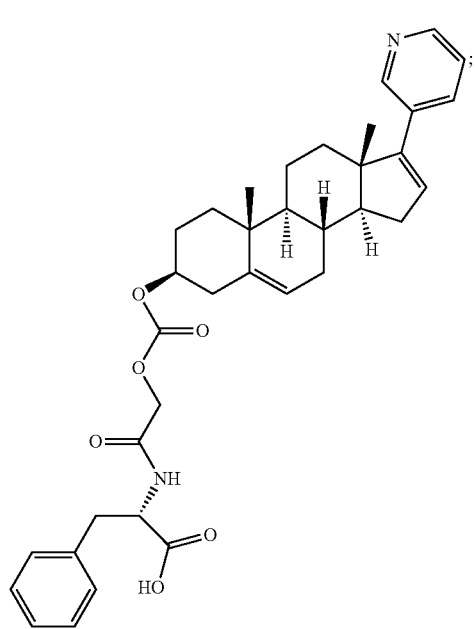

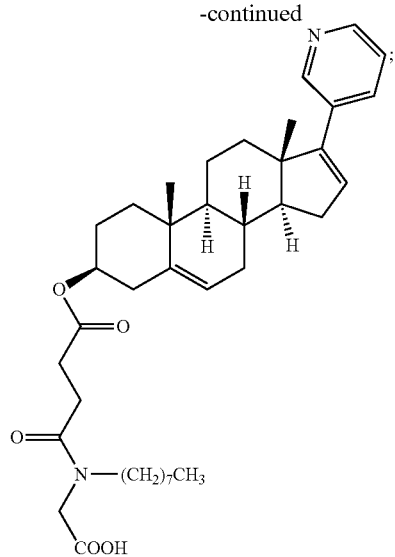
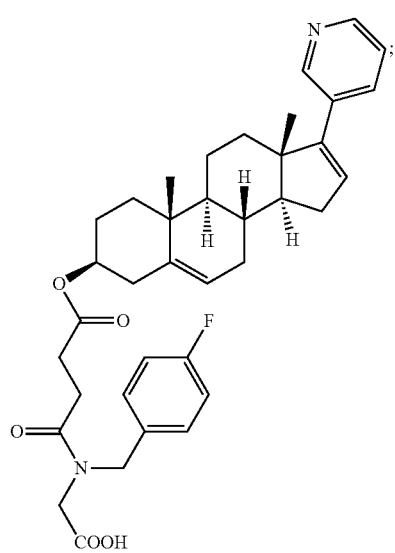
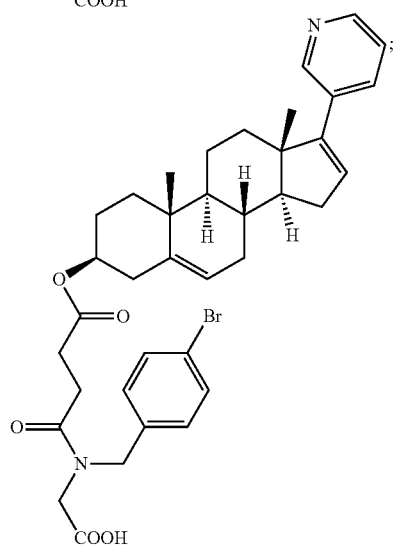
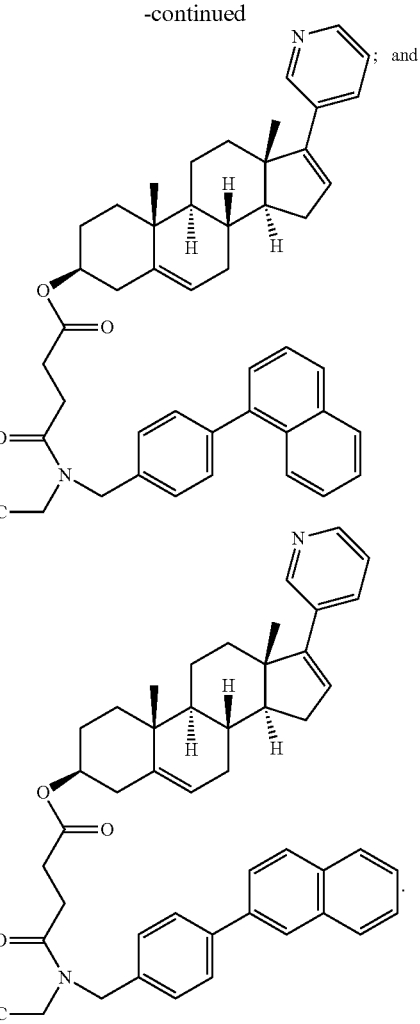
11. The compound of claim 3, or pharmaceutically acceptable salt thereof, wherein the compound is selected from the group consisting of:
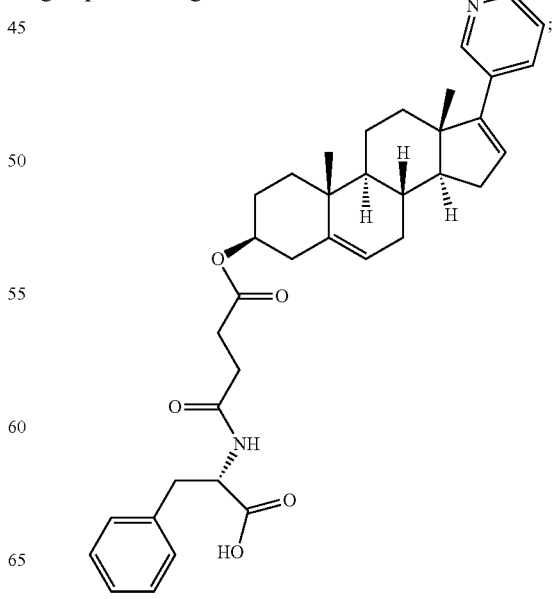

103
-continued
104
-continued
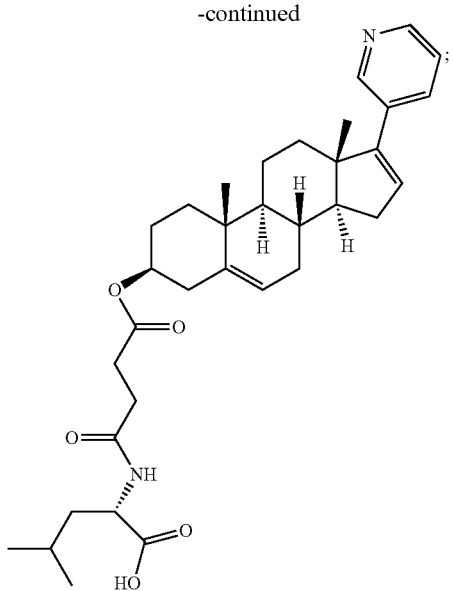
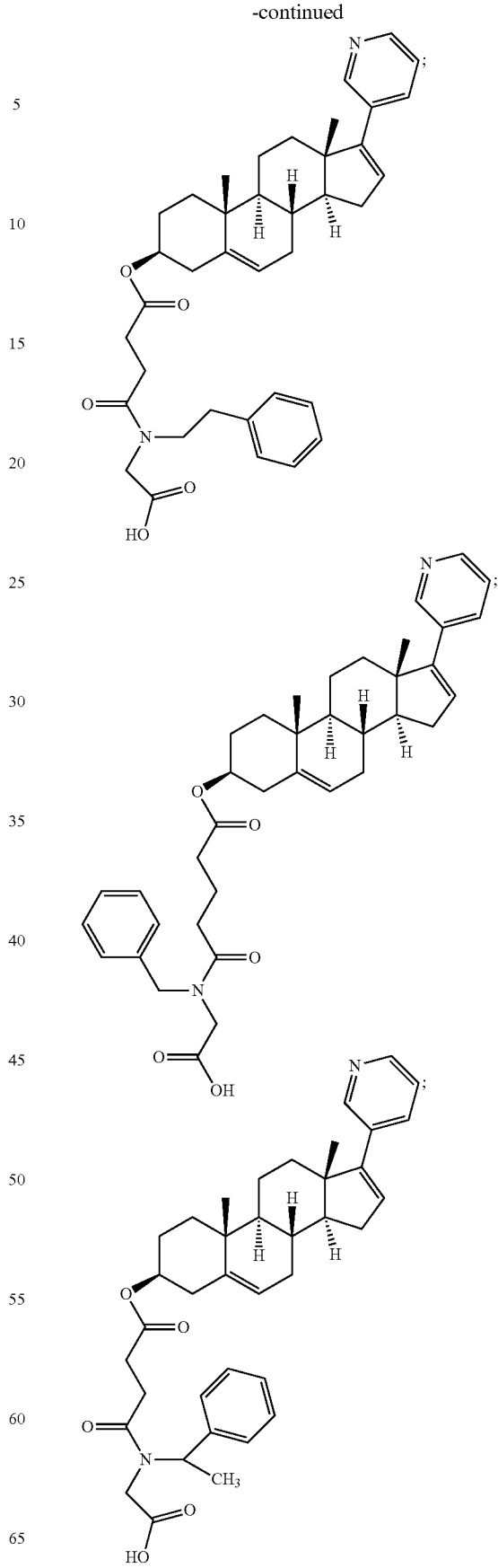

-continued

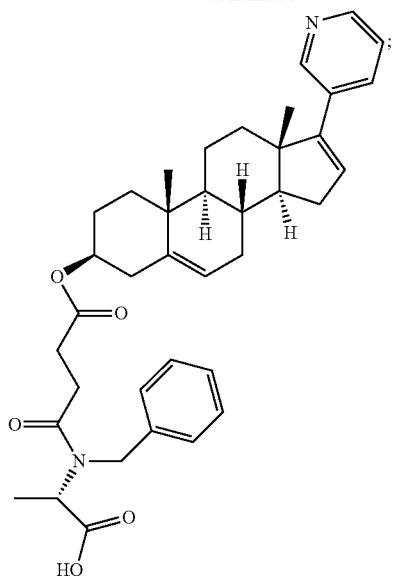

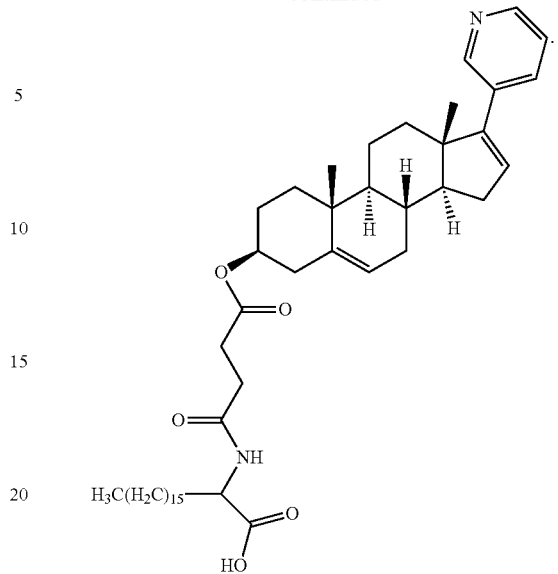

; and

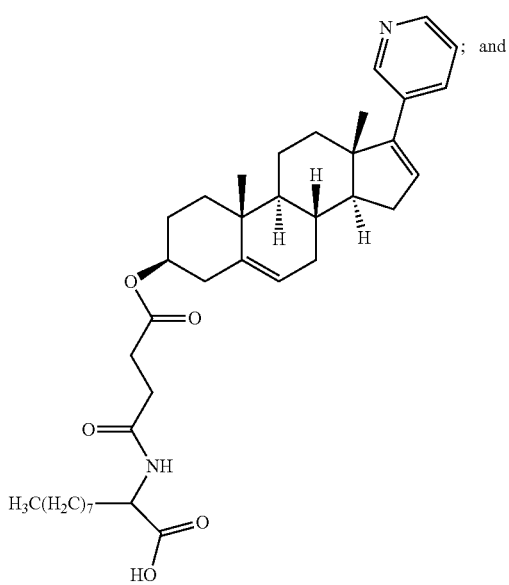

12. A non-covalently bound complex of the compound of claim 3, or pharmaceutically acceptable salt thereof, and human serum albumin in a molar ratio from about 1:1 to about 10:1, wherein the non-covalently bound complex has solubility in aqueous solution of at least 5 mg/mL.

13. The non-covalently bound complex of claim 12, wherein the non-covalently bound complex has solubility in aqueous solution of at least 20 mg/mL.

14. The non-covalently bound complex of claim 12, in a solid formulation.

15. The non-covalently bound complex of claim 12, in an aqueous formulation.

16. The non-covalently bound complex of claim 15, wherein the aqueous formulation is free of solvents other than water.

17. A pharmaceutical composition comprising a non-covalently bound complex of claim 1, and a pharmaceutically acceptable carrier.

18. A method of treating prostate cancer, the method comprising the step of administering to the subject in need thereof a therapeutically effective amount of a pharmaceutical composition of claim 17.

19. A method of treating a disease associated with dysregulated activity of CYP17, the method comprising administering to a mammalian patient a pharmaceutical composition according to claim 17 wherein the disease is prostate cancer.

* * * * *

UNITED STATES PATENT AND TRADEMARK OFFICE
CERTIFICATE OF CORRECTION

PATENT NO. : 9,937,259 B2
APPLICATION NO. : 15/320353
DATED : April 10, 2018
INVENTOR(S) : Qun Sun Page 1 of 2

It is certified that error appears in the above-identified patent and that said Letters Patent is hereby corrected as shown below:

On the Title Page

Column 2 (item (56) Other Publications), Line 8, delete "Relieved" and insert -- Retrieved --;

Column 2 (item (56) Other Publications), Line 16, delete "informations]," and insert -- information], --;

Column 2 (item (56) Other Publications), Line 29, delete "360," and insert -- 860, --;

In the Claims

Column 92, Lines 57-63 (approx.), Claim 3, delete

"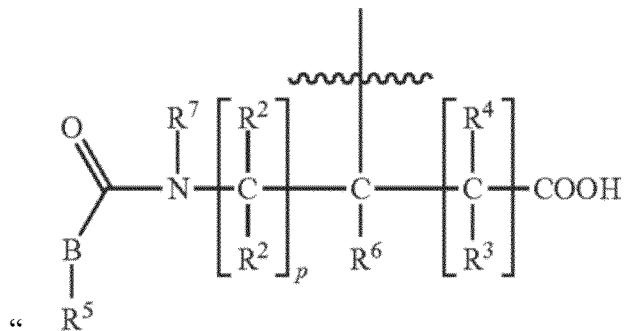" and insert

--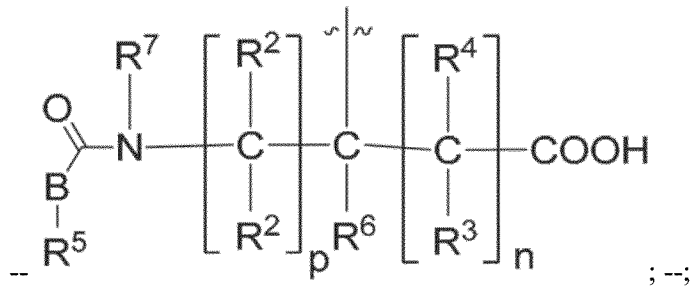; --;

Signed and Sealed this
Nineteenth Day of May, 2020

Andrei Iancu
*Director of the United States Patent and Trademark Office*

Column 93, Line 2, Claim 3, delete "0-lower" and insert -- O-lower --;

Column 93, Line 44, Claim 3, delete "$NR_1$;" and insert -- $NR^1$; --.